United States Patent
White et al.

(10) Patent No.: US 9,850,271 B2
(45) Date of Patent: *Dec. 26, 2017

(54) CRYSTALLINE SOLVATE FORMS OF A PHARMACEUTICAL

(71) Applicant: NeurMedix, Inc., San Diego, CA (US)

(72) Inventors: Steven K White, San Diego, CA (US); Igor Ivanisevic, West Lafayette, IN (US); Kyle Stephens, West Lafayette, IN (US); Mark Andres, West Lafayette, IN (US); Brenton Skylar Wolfe, West Lafayette, IN (US)

(73) Assignee: NeurMedix, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/348,107

(22) Filed: Nov. 10, 2016

(65) Prior Publication Data

US 2017/0152281 A1 Jun. 1, 2017

Related U.S. Application Data

(63) Continuation of application No. 14/459,528, filed on Aug. 14, 2014, now Pat. No. 9,555,046, which is a continuation of application No. 13/563,982, filed on Aug. 1, 2012, now abandoned, which is a continuation of application No. 12/418,559, filed on Apr. 3, 2009, now Pat. No. 8,252,947.

(60) Provisional application No. 61/042,240, filed on Apr. 3, 2008.

(51) Int. Cl.
C07J 1/00 (2006.01)

(52) U.S. Cl.
CPC .............. *C07J 1/00* (2013.01); *C07B 2200/13* (2013.01)

(58) Field of Classification Search
CPC ................ C07J 5/00; C07J 7/00; A61K 31/57
See application file for complete search history.

(56) References Cited

U.S. PATENT DOCUMENTS

| | | | |
|---|---|---|---|
| 4,329,366 A | 5/1982 | Nashed et al. |
| 4,898,694 A | 2/1990 | Schwartz et al. |
| 5,292,730 A | 3/1994 | Lardy |
| 5,296,481 A | 3/1994 | Partridge et al. |
| 5,565,467 A | 10/1996 | Batchelor et al. |
| 5,641,766 A | 6/1997 | Lardy |
| 5,859,000 A | 1/1999 | Dowell et al. |
| 5,869,709 A | 2/1999 | Marwah et al. |
| 5,922,701 A | 7/1999 | Araneo |
| 6,111,118 A | 8/2000 | Marwah et al. |
| 6,274,746 B1 | 8/2001 | Marwah et al. |
| 6,384,251 B1 | 5/2002 | Marwah et al. |
| 6,451,340 B1 | 9/2002 | Arimilli et al. |
| 6,667,299 B1 | 12/2003 | Ahlem et al. |
| 6,686,486 B1 | 2/2004 | Marwah et al. |
| 6,930,192 B2 | 8/2005 | Dalko et al. |
| 7,045,513 B1 | 5/2006 | Parasrampuria et al. |
| 7,524,835 B2 | 4/2009 | Frincke |
| 7,691,835 B2 | 4/2010 | Frincke |
| 7,696,189 B1 | 4/2010 | Frincke |
| 7,776,845 B2 | 8/2010 | Frincke |
| 7,863,261 B2 | 1/2011 | Frincke |
| 7,867,990 B2 | 1/2011 | Schultz et al. |
| 7,964,604 B2 | 6/2011 | Eijgendaal et al. |
| 8,003,636 B2 | 8/2011 | Wollmann et al. |
| 8,217,025 B2 | 7/2012 | Flores-Riveros et al. |
| 8,252,947 B2 * | 8/2012 | White .................. C07J 5/00 552/562 |
| 8,354,396 B2 | 1/2013 | Frincke et al. |
| 9,310,310 B2 | 4/2016 | Gozum |
| 9,555,046 B2 | 1/2017 | White et al. |

(Continued)

FOREIGN PATENT DOCUMENTS

| | | |
|---|---|---|
| EP | 2 273 994 B1 | 12/2015 |
| WO | WO 01/30802 A2 | 5/2001 |
| WO | WO 2008/039566 A2 | 4/2008 |

OTHER PUBLICATIONS

Hursthouse et al, Organic Process Research & Development, Why Do Organic Compounds Crystallise Well or Badly or Ever so Slowly? Why Is Crystallisation Nevertheless Such a Good Purification Technique?, 2009, 73, pp. 1231-1240.*

(Continued)

*Primary Examiner* — Paul A Zucker
(74) *Attorney, Agent, or Firm* — Knobbe Martens Olson & Bear LLP

(57) ABSTRACT

The invention provides and describes solid state 17α-ethynyl-androst-5-ene-3β,7β,17β-triol including amorphous and crystalline forms and specific polymorphic forms thereof. Anhydrates and solvates of 17α-ethynyl-androst-5-ene-3β, 7β,17β-triol include Form I anhydrate and Form IV and Form V solvates. The invention further relates to solid and suspension formulations containing 17α-ethynyl-androst-5-ene-3β,7β,17β-triol in a described solid state form and use of the formulations to treat hyperglycemic conditions, such as type 2 diabetes and metabolic syndrome, and autoimmune conditions, such as rheumatoid arthritis, ulcerative colitis and type 1 diabetes, among other inflammation related conditions in subjects or human patients. The invention also relates to methods to make liquid formulations from solid state forms of 17α-ethynyl-androst-5-ene-3β,7β,17β-triol and uses of such formulations in treating the described conditions.

20 Claims, 24 Drawing Sheets

(56) References Cited

U.S. PATENT DOCUMENTS

| | | |
|---|---|---|
| 2003/0060425 A1 | 3/2003 | Ahlem et al. |
| 2003/0083231 A1 | 5/2003 | Ahlem et al. |
| 2003/0144219 A1 | 7/2003 | Phinney et al. |
| 2005/0075321 A1 | 4/2005 | Ahlem et al. |
| 2006/0079492 A1 | 4/2006 | Ahlem et al. |
| 2006/0088473 A1 | 4/2006 | Dowding et al. |
| 2006/0211604 A1 | 9/2006 | Mentzer |
| 2007/0129282 A1 | 6/2007 | Ahlem et al. |
| 2008/0015174 A1 | 1/2008 | Reading et al. |
| 2008/0146532 A1 | 6/2008 | Flores-Riveros et al. |
| 2008/0153792 A1 | 6/2008 | Frincke et al. |
| 2008/0153797 A1 | 6/2008 | Frincke et al. |
| 2008/0221074 A1 | 9/2008 | Flores-Riveros et al. |
| 2009/0326251 A1 | 12/2009 | White et al. |
| 2010/0075937 A1 | 3/2010 | Flores-Riveros et al. |
| 2016/0175322 A9 | 6/2016 | White et al. |

OTHER PUBLICATIONS

Caira, Topics in Current Chemistry, Design of Organic Solids, Crystalline Polymorphism of Organic Compounds, 1998, Springer, New York, pp. 162-208.*

* cited by examiner

CRYSTALLINE SOLVATE FORMS OF A PHARMACEUTICAL

CROSS REFERENCE TO RELATED APPLICATIONS

This non-provisional U.S. patent application claims priority to and is a continuation application of U.S. application Ser. No. 14/459,528, filed Aug. 14, 2014, now U.S. Pat. No. 9,555,046, which issued on Jan. 31, 2017 and which is a non-provisional U.S. patent application that claims priority to abandoned U.S. application Ser. No. 13/563,982, filed Aug. 1, 2012, which is a continuation of and claims priority to U.S. non-provisional application Ser. No. 12/418,559 filed on Apr. 3, 2009, now U.S. Pat. No. 8,252,947, which claims priority to abandoned U.S. provisional application Ser. No. 61/042,240 filed Apr. 3, 2008, all of which patents and applications are incorporated herein by reference in their entireties.

FIELD OF THE INVENTION

The invention relates to solid state forms of 17-Ethynyl-10R,13S-dimethyl 2,3,4,7,8R,9S,10,11,12,13,14S,15,16,17-hexadecahydro-1H-cyclopenta[a]phenanthrene-3R,7R,17S-triol and methods for preparation of these solid state forms.

The invention further relates to solid formulations comprising the solid state forms and to methods for using the solid state forms, including the polymorph forms and pseudopolymorph forms, in preparing solid and liquid formulations. The invention further relates to methods for using the solid state forms for the treatment of conditions related to hyperglycemia and autoimmunity. Unit dosage forms for the solid and liquid formulations are also included.

BACKGROUND OF THE INVENTION

The ability of a substance to exist in more than one crystalline form is generally referred to as polymorphism and these different crystalline forms are usually named "polymorphs" and may be referred to by certain analytical properties such their X-ray powder diffraction (XRPD) patterns. In general, polymorphism reflects the ability of a molecule to change its conformation or to form different intermolecular and intramolecular interactions. This can result in different atom arrangements that are reflected in the crystal lattices of different polymorphs. However, polymorphism is not a universal feature of solids, since some molecules can exist in one or more crystal forms while other molecules cannot. Therefore, the existence or extent of polymorphism for a given compound is unpredictable.

The different polymorphs of a substance posses different crystal lattice energies and thus each polymorph typically shows one or more different physical properties in the solid state, such as density, melting point, color, stability, dissolution rate, flowability, compatibility with milling, granulation and compacting and/or uniformity of distribution [See, e.g., P. DiMartino, et al., J. Thermal Anal. 48:447-458 (1997)]. The capacity of any given compound to occur in one or more crystalline forms (i.e. polymorphs) is unpredictable as are the physical properties of any single crystalline form. The physical properties of a polymorphic form may affect its suitability in pharmaceutical formulations. For example, those properties can affect positively or negatively the stability, dissolution and bioavailability of a solid-state formulation, which subsequently affects suitability or efficacy of such formulations in treating disease.

An individual polymorph having one or more desirable properties can be suitable for the development of a pharmaceutical formulation having desired property(ies). Existence of a compound with a polymorphic form(s) having undesirable properties can impede or prevent development of the polymorphic form as a pharmaceutical agent.

In the case of a chemical substance that exists in more than one polymorphic form, the less thermodynamically stable forms can occasionally convert to the more thermodynamically stable form at a given temperature after a sufficient period of time. When this transformation is rapid, such a thermodynamically unstable form is referred to as a "metastable" form. In some instances, a metastable form may exhibit sufficient chemical and physical stability under normal storage conditions to permit its use in a commercial form. Likewise, the amorphous form of an active pharmaceutical ingredient may have different solubility in comparison to a given crystalline material due to reduction of crystal lattice forces in the amorphous material that must be overcome to effect dissolution in aqueous or non-aqueous liquids.

SUMMARY OF THE INVENTION

In a principal embodiment, the invention provides new solid state forms of 17-Ethynyl-10R,13S-dimethyl 2,3,4,7, 8R,9S,10,11,12,13,14S,15,16,17-hexadecahydro-1H-cyclopenta[a]phenanthrene-3R,7R,17S-triol, which is represented by Formula 1. This compound is suitable for treating a condition related to inflammation, hyperglycemia, autoimmunity and related conditions such as diabetes and ulcerative colitis.

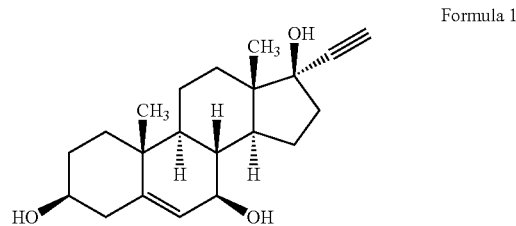

Formula 1

The compound of Formula 1 (hereafter also referred to as Compound 1 or 17α-ethynyl-androst-5-ene-3β,7β,17β-triol) has been prepared in amorphous and crystalline forms, and in particular, crystalline forms referred herein as Form I, Form II, Form III or Form IV.

Conditions related to hyperglycemia include hyperglycemia, insulin resistance, Type 2 diabetes (including forms with (1) predominant or profound insulin resistance, (2) predominant insulin deficiency and some insulin resistance and (3) forms intermediate between these), obesity and hyperlipidemia conditions such as hypertriglyceridemia and hypercholesterolemia. The formulations comprising a solid state form of Compound 1, including Crystalline form I essentially free of amorphous Compound 1, amorphous Compound 1 essentially free of crystalline Compound 1 and a mixture of crystalline and amorphous forms of Compound 1, are thus useful to treat, prevent, ameliorate or slow the progression of Type 2 diabetes or other hyperglycemia conditions, in a subject such as a human or a mammal.

Conditions related to autoimmunity include Type 1 diabetes (including Immune-Mediated Diabetes Mellitus and Idiopathic Diabetes Mellitus), multiple sclerosis, optic neuritis, Crohn's disease (regional enteritis), ulcerative colitis, inflammatory bowel disease, rheumatoid arthritis and Hashimotos' thyroiditis. The formulations comprising a solid state form of Compound 1 including crystalline Form I, essentially free of other crystalline and amorphous forms of Compound 1, and a mixture of crystalline and amorphous forms of Compound 1 are thus useful to treat, prevent, ameliorate or slow the progression of arthritis, ulcerative colitis, multiple sclerosis, optic neuritis or other autoimmune condition, in a subject such as a human or a mammal.

In diabetes, the formulations described herein are useful to (1) enhance β-cell function in the islets of Langerhans (e.g., increase insulin secretion), (2) reduce the rate of islet cell damage, (3) increase insulin receptor levels or activity to increase cell sensitivity to insulin and/or (4) modulate glucocorticoid receptor activity to decrease insulin resistance in cells that are insulin resistant.

One embodiment of the invention is directed to a particular crystalline form of Compound 1 (e.g., crystalline Form I) substantially free or essentially free of other crystalline or amorphous forms of Compound 1.

In certain embodiments, the present invention is directed to a particular polymorph form (e.g., crystalline Form I or Form II) or pseudopolymorph form (e.g., crystalline Form III or Form IV) of Compound 1 that is substantially free or essentially free of other polymorph, pseudopolymorph or crystalline forms of Compound 1.

Another embodiment of the invention is directed to amorphous Compound 1, typically wherein the amorphous material is substantially free or essentially free of crystalline Compound 1.

In certain embodiments, the present invention provides methods of making, isolating and/or characterizing the solid state forms of the invention. Some of these embodiments are directed to methods to prepare Compound 1 in crystalline form. Other such embodiments are directed to methods to prepare Compound 1 in amorphous form.

In some embodiments a solid state form of Compound 1 is characterized or identified by methods comprising X-ray Powder Diffraction (XRPD) and one or more thermal methods including Differential Thermal Analysis (DTA), Differential Scanning Calorimetry (DSC), Modulated Differential Scanning Calorimetry (m DSC), Thermogravimetric Analysis (TGA), Thermogravimetric-infrared (TG-IR) analysis and melting point measurements.

In some embodiments a solid state form of Compound 1 is characterized or identified by methods including XRPD and a vibrational spectroscopy method such as Raman spectroscopy.

Other embodiments of the invention are directed to solid formulations comprising a solid state form of Compound 1 and methods for preparation of the solid formulation.

In certain embodiments, the present invention encompasses the use of the solid state forms of the invention for preparing a final drug product. Preferred drug products are generally prepared using Form I, Form III or amorphous 17α-ethynyl-androst-5-ene-3β,7β,17β-triol.

Other embodiments of the invention are directed to pharmaceutically acceptable formulations comprising a particular crystalline form (e.g. crystalline Form I, Form II, Form III or Form IV) of Compound 1 that is substantially free or essentially free of other solid state forms, such as amorphous Compound 1 or other crystalline forms of Compound 1, and methods for preparation of the formulations with solid and liquid formulations comprising Form I most preferred.

Still other embodiments of the invention are directed to liquid formulations prepared by contacting or admixing at least one solid state form of Compound 1 with a liquid excipient into which Compound 1 has sufficient solubility, optionally in the presence of another excipient, and methods for preparation of the liquid formulation.

Other embodiments that are related to contacting or admixing at least one solid state form of Compound 1 with a liquid excipient are directed to solid formulations as suspension formulation wherein at least some amount of Compound 1 is present as particles in the formulation. These suspension formulations are made using a solid state form described herein.

Yet another embodiment of the invention is directed to methods for treating a condition related to hyperglycemia and autoimmunity in a subject with a solid formulation comprising a solid state form of Compound 1 such as amorphous or a crystalline form of Compound 1.

Yet another embodiment of the invention is directed to methods for treating a condition related to hyperglycemia, such Type 2 diabetes, in a subject with a solid formulation comprising a particular crystalline form (e.g. crystalline Form I, Form II, Form III or Form IV) of Compound 1 that is substantially free of other solid state forms, such as amorphous and other crystalline forms of Compound 1.

Another embodiment of the invention is directed to methods for treating a condition related to autoimmunity, such as Type 1 diabetes, rheumatoid arthritis or Hashimotos' thyroiditis and an inflammatory bowel disease such as Crohn's disease and ulcerative colitis, in a subject with a solid formulation comprising a solid state form of Compound 1, such as amorphous or a crystalline form of Compound 1. In these embodiments crystalline Form I is preferred.

Invention embodiments also include the use or Compound 1 in amorphous or crystalline form for the preparation of a medicament for the treatment or prophylaxis of a condition related to hyperglycemia or autoimmunity.

Still other embodiments are directed to methods for preparing liquid formulations using a solid state form of Compound 1 and uses of such formulations for treating a condition related to hyperglycemia or autoimmunity.

Other embodiments and advantages of the present invention are as described elsewhere in the specification including the numbered embodiments and the claims.

DETAILED DESCRIPTION

Figure 1:
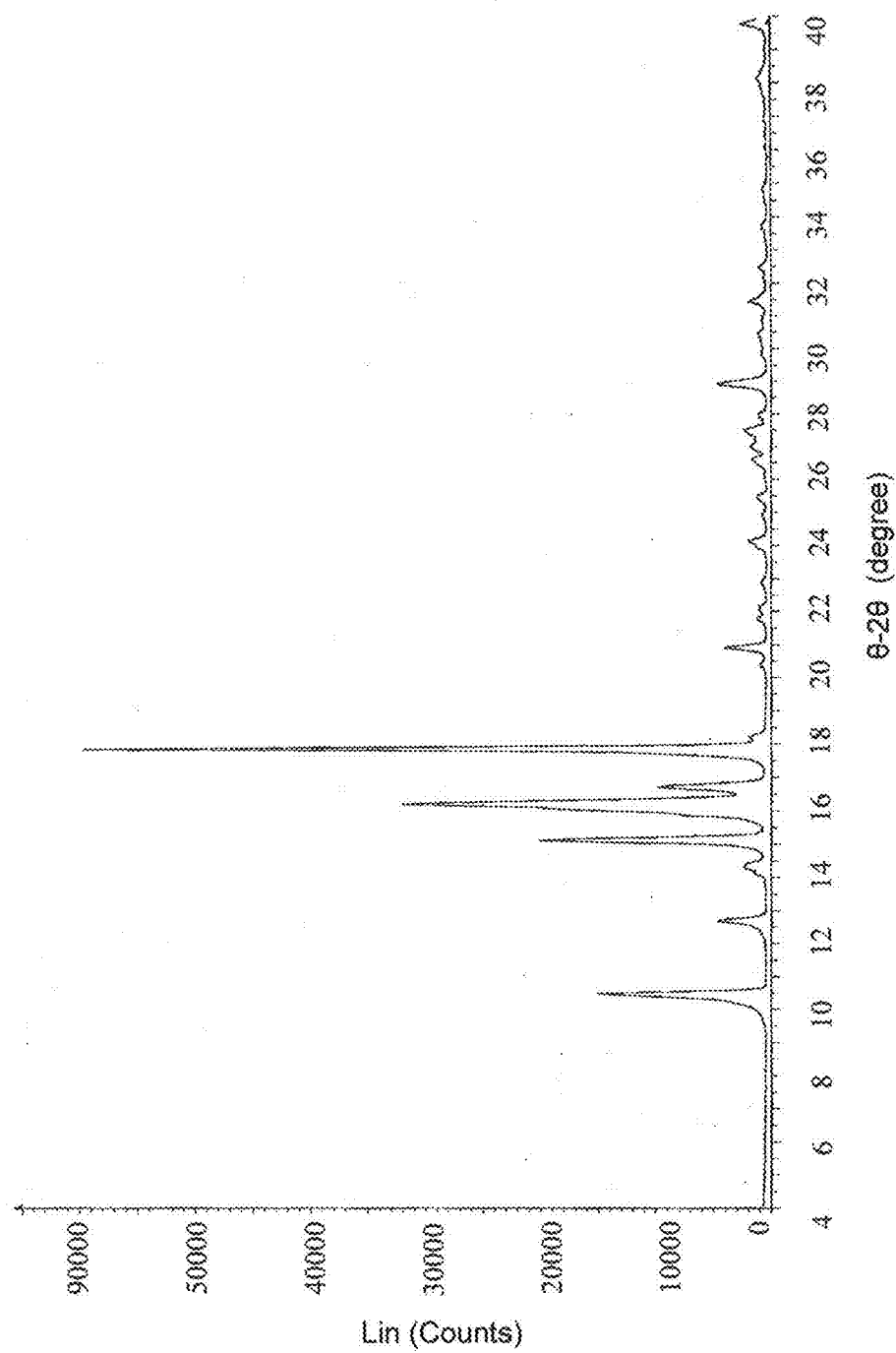
FIG. 1 is a low resolution XRPD pattern of Form I 17α-ethynyl-androst-5-ene-3β,7β,17β-triol prepared by bulk recrystallization.

Definitions. As used herein or otherwise stated or implied by context, terms that are defined herein have the meanings that are specified. The descriptions of embodiments and examples that are described illustrate the invention and they are not intended to limit it in any way. Unless otherwise contraindicated or implied, e.g., by mutually exclusive elements or options, in the descriptions or throughout this specification, the terms "a" and "an" mean one or more and the term "or" means and/or.

Unless specified otherwise explicitly or by context, percentage amounts are expressed as % by weight (w/w). Thus, a solid-dosage formulation containing at least about 2% Compound 1 is a solid-dosage formulation or suspension containing at least about 2% w/w Compound 1. Solid Compound 1 containing 0.1% water means 0.1% w/w water is associated with the solid.

"About" and "approximately," when used in connection with a numeric value or range of values which is provided to describe a particular solid form, e.g., a specific temperature or temperature range, such as, for example, that describing a melting, dehydration, desolvation or glass transition; a mass change, such as, for example, a mass change as a function of temperature or humidity; a solvent or water content, in terms of, for example, mass or a percentage; or a peak position, such as, for example, in analysis by IR or Raman spectroscopy or XRPD; indicate that the value or range of values may deviate to an extent deemed reasonable to one of ordinary skill in the art while still describing the particular solid state form. Specifically, the terms "about" and "approximately," when used in this context, indicate that the numeric value or range of values may vary by 20%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1% or 0.01% of the recited value or range of values while still describing the particular composition or solid state form.

"Solid State" as used herein refers to a physical state of a compound or composition comprising the compound, such as 17α-ethynyl-androst-5-ene-3β,7β,17β-triol (i.e., Compound 1); wherein at least about 2-10% of the mass of the compound that is present exists as a solid. Typically, the majority of the mass of Compound 1 will be in solid state form. More typically, between at least about 80-90% of the mass of Compound 1 is in solid form. Solid state forms include crystalline, disordered crystalline, polycrystalline, microcrystalline, nanocrystalline, partially crystalline, amorphous and semisolid forms or mixtures thereof, optionally with non-solid or non-crystalline Compound 1. Solid state forms of Compound 1 further include polymorphs, pseudopolymorphs, hydrates, solvates, dehydrated hydrates and desolvated solvates and mixtures thereof, optionally with non-solid or non-crystalline Compound 1. Thus, solid state forms of Compound 1 will include a single polymorph form of Compound 1, a single pseudo-polymorph form of Compound 1, a mixture of two or more, typically two or three, polymorph or pseudo-polymorph forms of Compound 1 or a combination of any one of these solid state forms, optionally with non-solid or non-crystalline Compound 1, provided that at least about 2-10% of the mass of Compound 1 is in solid form.

The term "crystalline" and related terms used herein, when used to describe a substance, component or product, means that the substance, component or product is crystalline as determined by visual inspection or usually with a suitable method, typically an X-ray diffraction method such as X-ray powder diffraction [See, e.g., Remington's Pharmaceutical Sciences, 18th ed., Mack Publishing, Easton Pa., p 173 (1990); The United States Pharmacopeia, 23$^{rd}$ ed., pp. 1843-1844 (1995)].

The term "crystalline forms" and related terms herein refers to the various crystalline modifications of a given substance, including, but not limited to, polymorphs, solvates, hydrates, mixed solvates, co-crystals and other molecular complexes. A crystalline form may also be a mixture various crystalline modifications of a given substance such as a combination of pseudopolymorph or polymorph forms, a combination of one or more polymorph forms with one or more pseudopolymorph or a combination of such forms with amorphous or non-solid state forms of the substance. Typical combinations are of two or more polymorph or pseudo polymorph forms, such a mixture of a polymorph form with a pseudopolymorph form or a mixture of a polymorph or pseudopolymorph form with amorphous material. Typically crystalline forms are typically distinguishable from each other by their XRPD patterns. Solid state forms having different crystal morphologies but essentially identical XRPD patterns are considered to be different crystalline forms, since different morphologies can exhibit different properties related to physical shape. Properties related to physical shape include dissolution rate, stability, hygroscopicity, mechanical properties such hardness, tensile strength, compatibility (tableting) and those related to handling, e.g., flow, filtering, blending and other physical or pharmaceutical properties as described herein for different polymorphs.

"Polymorph" as used herein refers to a defined crystalline form of 17α-ethynyl-androst-5-ene-3β,7β,17β-triol (i.e., Compound 1). Polymorphs typically differ in their physical properties due to the order of the molecules in the lattice of the polymorph. Thus, polymorphs may exhibit one or more differences in physical or pharmaceutical properties including hygroscopicity, solubility, intrinsic dissolution rate, solid state reaction rates (i.e., chemical stability of a pharmaceutical ingredient as the drug substance or drug product), crystalline stability (i.e. tendency to transition to a more thermodynamically stable crystalline form), surface free energy, interfacial tension, mechanical strength (e.g., hardness, brittleness, plastic deformation, docility, malleability, etc.), tensile strength, compactability (i.e., tableting) and processability (e.g., handling, flow, blending, etc.). Differences in physical and mechanical properties of polymorphic forms of a drug substance may also affect scale-up and transfer from laboratory procedures though pilot plant and then to full production.

Polymorphs existing as hydrates, solvates or mixed solvates are generally referred to as pseudopolymorphs and represent different polymorphic or solid state forms in view of an isostructural polymorph form that is anhydrous or not a solvate. Pseudopolymorphs that differ in solvate identity or stoichiometry are also considered different polymorphic or solid state forms in view of each other. For example, Compound 1 existing as a solvate (e.g., crystalline Form III) is a different solid state form in view of another solvate (e.g., crystalline Form IV) or an anhydrate (e.g., crystalline Form I). Stability profiles of hydrates and solvates at various temperatures and/or at different vapor pressures of water (e.g., relative humidity) or organic solvents will sometimes differ from those of the isostructural anhydrate or desolvate. Such differences may influence formulation, processing or stability of an active pharmaceutical ingredient (e.g., Compound 1), either as the drug substance in a drug product under various storage conditions.

Thus, different crystalline or polymorphic forms may have different physical properties such as, for example, melting temperatures, heats of fusion, solubilities, and/or vibrational spectra as a result of the arrangement or conformation of the molecules in the crystal lattice (see, e.g., Byrn, S. R., Pfeiffer, R. R., and Stowell, J. G. (1999) Solid-State Chemistry of Drugs, 2$^{nd}$ ed., SSCI, Inc.: West Lafayette, Ind.). The differences in physical properties exhibited by polymorphs and pseudopolymorphs may affect pharmaceutical parameters such as storage stability, compressibility and density (important in formulation and product manufacturing), and dissolution rate, which can be an important factor in bioavailability. Differences in stability may result from changes in chemical reactivity (e.g., differential oxidation, such that a dosage form discolors more rapidly when comprised of one polymorph or pseudopolymorph than when comprised of another polymorphic form) or mechanical changes (e.g., tablets crumble on storage as a kinetically favored polymorph converts to thermodynamically more stable polymorph) or both (e.g., tablets of one polymorph are more susceptible to breakdown at high humidity). As a result of kinetic solubility/dissolution rate differences, in the extreme case, some polymorphic transitions may result in lack of potency or, at the other extreme, toxicity. In addition, the physical properties of the crystal may be important in processing, e.g., one polymorph might be more likely to form solvates or hydrates that may be difficult to filter or wash free of impurities due to, for example, by differences in crystal morphology and/or particle size distribution.

Typically, crystalline forms are distinguished from each other by one or more physical or analytical properties such as rate of dissolution, Infrared and Raman spectroscopy, X-ray diffraction techniques such as single crystal and powder diffraction techniques, solid state-NMR (SS-NMR), thermal techniques such as melting point, differential thermal analysis (DTA), differential scanning calorimetry (DSC), thermal gravimetric analysis (TGA) and other methods as disclosed elsewhere in the specification. Additional methods to characterize or distinguish one pseudopolymorph from another polymorphic form, include elemental analysis, Karl-Fisher titration, dynamic vapor sorption analysis, thermogravimetric-infrared spectroscopic analysis (TG-IR), residual solvent gas chromatography and $^1$H-NMR.

The term "isostructural crystalline form," as used herein, refers to a crystal form of a substance that has a common structural similarity with another crystalline form, including approximately similar interplanar spacing in the crystal lattice. Thus, isostructural crystalline forms will have similar molecular packing motifs, but differing unit cell parameters (a symmetry translation). Due to their common structural similarity, isostructural crystalline forms typically have similar, but not necessarily identical, X-ray powder diffraction patterns. An isostructural crystalline form may be based upon a substance that is a neutral molecule or a molecular complex. The isostructural crystalline form may be a solvate, including a hydrate, or a desolvated solvate crystalline form of the substance. Isostructural forms that are solvates of a polymorph are sometimes referred to as pseudopolymorphic to the unsolvated polymorph. A solvated crystalline form typically contains one or more solvents, including water, in the crystal lattice, that may be the solvent or solvents of crystallization used in preparing the crystalline form.

"Amorphous", as used herein, refers to a solid state form of a compound (e.g., Compound 1) wherein in the three dimensional structure positions of the molecules relative to one another are essentially random, [for example, see Hancock et al. "Characteristics and significance of the amorphous state in pharmaceutical systems" *J. Pharm. Sci.* Vol. 86, pp. 1-12 (1997)]. As a result, amorphous material will have only liquid-like short range order, and, when examined by X-ray diffraction, will generally produce broad, diffuse scattering will result in peak intensity sometimes centered on one or more amorphous halos. Thus, XRPD analysis of amorphous material will provide a 2-theta pattern with one or more broad bands with no distinctive peaks.

Amorphous Compound 1 may sometimes be characterized by its glass transition temperature ($T_g$), which defines a pseudo second order phase transition in which a supercooled melt of Compound 1 yields, on cooling, a glassy structure with properties similar to those of crystalline Compound 1. However, since $T_g$ is a kinetic parameter, its value will be dependent on the melt cooling rate and the measurement conditions used for its determination (e.g., the slower the melt cooling rate, the lower $T_g$ will be). Furthermore, $T_g$ of an amorphous sample, such as amorphous Compound 1 will be highly dependent on the amount of water present. For example, a 1% increase in water content may lower $T_g$ by about 10° C. or more. The glass transition temperature for a sample of amorphous Compound 1 may be obtained by differential scanning calorimetry (DSC), which will exhibit a heat capacity change having a second order endothermic transition that appears as a step transition. The inflection point of this transition provides $T_g$.

"Formulation" or "pharmaceutically acceptable formulation" as used herein refers to a composition comprising 17α-ethynyl-androst-5-ene-3β,7β,17β-triol (i.e., Compound 1), present in a solid state form in addition to one or more pharmaceutically acceptable excipients. Formulations include compositions prepared from a solid state form of Compound 1, wherein the composition is suitable for administration to a human. The formulation may be comprised of, or be prepared from, one, two or more crystalline forms of Compound 1, e.g. a single polymorph or pseudopolymorph form of Compound 1, a mixture of two polymorph forms of Compound 1 or a mixture of a polymorph form of Compound 1 and a pseudopolymorph form of Compound 1. The formulation may be comprised of, or be prepared from amorphous Compound 1 or a mixture of a polymorph or pseudopolymorph form of Compound 1 and amorphous Compound 1. Typically, the formulations will be comprised of, or prepared from, a single crystalline form of Compound 1 (e.g., crystalline Form I, Form II, Form III or Form IV), amorphous Compound 1 or, less preferably, a mixture of a single polymorph or pseudopolymorph form and amorphous Compound 1. Preferred formulations contain Form I 17α-ethynyl-androst-5-ene-3β,7β,17β-triol.

"Solid formulation" as used herein refers to a formulation wherein Compound 1 is in solid state form in the presence of one or more pharmaceutically acceptable excipients wherein the majority of the mass amount of the solid state form of Compound 1 used in preparation of the formulation remains in that solid state form for at least about 6 months at ambient temperature, usually for at least about 12 months or 24 months at ambient temperature, when admixed with the excipients in proportions required for the solid state formulation. Dosage units that are a solid formulation include tablets, capsules, caplets, suspensions and other dosage units typically associated with oral administration of an active pharmaceutical ingredient in solid state form to a subject in need thereof.

"Liquid formulation" as used herein refers to a formulation wherein one or more solid state forms of Compound 1 has been admixed or contacted with one or more excipients, wherein at least one of the excipients is in liquid or non-solid state form (i.e. a non-solid excipient), in proportions required for the liquid formulation, such that a majority of the mass amount of Compound 1 is dissolved into the non-solid excipient. Dosage units containing a liquid formulation include syrups, gels, ointments and other dosage units typically associated with parenteral or enteral administration of an active pharmaceutical ingredient to a subject in need thereof in non-solid state form.

"Substantially free" as used herein refers to a compound such as Compound 1 wherein more than about 60% by weight of the compound is present as the given solid state form. For example, the term crystalline Compound 1 "substantially free" of amorphous material refers to a solid-state form of Compound 1 wherein more than about 60% of Compound 1 is in one or more crystalline forms. Such compositions preferably contain at least about 80%, more preferably at least about 90%, of Compound 1 in one or more crystalline forms with the remaining present as amorphous or non-crystalline Compound 1. In another example, the term amorphous Compound 1 "substantially free" of crystalline forms refers to a solid-state form of Compound 1 wherein more than about 60% of Compound 1 is amorphous. Such compositions typically contain at least about 80%, preferably at least about 90%, more preferably at least about 95%, of amorphous Compound 1, with the remaining present as one or more crystalline forms of Compound 1. In yet another example, the term Form I "substantially free" of other crystalline forms refers to a solid-state composition wherein more than about 60% of Compound 1 exists as a single crystalline form. Such compositions typically contain at least about 80%, preferably at least about 90%, more preferably at least about 95% Compound 1 as a single crystalline form. Preferred formulations contain at least about 80%, preferably at least about 90% and more preferably at least about 95% of Compound 1 as Form I, with the remaining Compound 1 present as other crystalline forms or in amorphous form or a combination thereof. Other preferred formulations contain at least about 80%, preferably at least about 90% and more preferably at least about 95% of Compound 1 in amorphous form with the remaining Compound 1 present in one or more crystalline forms. Most preferred formulations contain about 95-99% of Form I 17α-ethynyl-androst-5-ene-3β,7β,17β-triol with about 97%, about 98% or about 99% particularly preferred.

"Essentially free" as used herein refers to a component so identified as not being present in an amount that is detectable under typical conditions used for its detection or would adversely affect the desired properties of a composition or formulation in which the component may be found. For example, "essentially free of liquid" means a composition or formulation in solid form that does not contain water or solvent, in liquid form, in an amount that would adversely affect the pharmaceutical acceptability of the formulation or composition for use in a solid dosage form to be administered to a subject in need thereof. A suspension is considered a solid formulation and for such formulations liquid excipient(s) comprising the suspension formulation are not included within this definition. "Crystalline Form I essentially free of amorphous Compound 1" refers to a specific crystalline form of Compound 1 in which amorphous Compound 1 is not detected by XRPD analysis. Typically, the detection limit for amorphous material within crystalline material is about 10%.

"Substantially pure" as used herein refers to a solid state form of Compound 1 that contain less than about 3% or less than about 2% by weight total impurities, or more preferably less than about 1% by weight water, and/or less than about 0.5% by weight impurities such as decomposition or synthesis by-products or residual organic solvent. Residual solvent does not include solvent that is part of a solvate of a solid state form of Compound 1 (e.g. a pseudopolymorph).

"Substantially identical" as used herein refers to measured physical characteristics that are comparable in value or data traces that are comparable in peak position and amplitude or intensity within the scope of variations that are typically associated with sample positioning or handling or the identity of the instrument employed to acquire the traces or physical characteristics or due to other variations or fluctuations normally encountered within or between laboratory environments or analytical instrumentation.

"Hydrate" as used here refers to a solid state form of Compound 1 that contains water molecules as an integral part of the solid state form and does not refer to water that is non-specifically bound to the bulk compound. Hydrates of Compound 1 in a crystalline form can be isolated site hydrates or channel hydrates. Hydrates can contain stoichiometric or nonstoichiometric amounts of water molecules per Compound 1 molecule. Typically, water will be present in a hydrate in the ratio of 0.25, 0.5, 1.0, 1.5 or 2.0 relative to Compound 1 on a mole basis.

"Solvate" as used here refers to a solid state form of Compound 1 that contains solvent molecules that is combined in a definite ratio to the molecules of the compound and is an integral part of the solid state form and does not refer to solvent that is non-specifically bound to bulk compound. When the solvent molecule is water such solvates are referred to as hydrates.

"Inflammation condition" as used herein refers to a condition that is characterized by the inappropriate or pathological presence of inflammation or its associated pain or fever. Inflammation may be present as a flare as for example in an autoimmune disease such as multiple sclerosis. Inflammation may be acute or chronic and present in conditions such as Type 2 diabetes, Alzheimer's disease and metastatic cancer, e.g., metastatic prostate or breast cancer.

Inflammation conditions include autoimmune conditions, such as multiple sclerosis, a lupus condition, e.g., systemic lupus erythematosus, an arthritis condition, e.g., rheumatoid arthritis, and an inflammatory bowel condition, e.g. as ulcerative colitis or Crohn's disease. Inflammation conditions also include metabolic conditions, such as hyperglycemia conditions, diabetes, liver cirrhosis conditions, e.g., nonalcoholic steatohepatitis (NASH), fatty liver conditions, acute and chronic lung conditions, e.g., obstructive pulmonary disease (COPD), acute asthma, chronic asthma, emphysema, acute bronchitis, allergic bronchitis, chronic bronchitis and lung fibrosis.

"Metabolic condition" as used herein include conditions such as type 1 diabetes, type 2 diabetes, obesity, metabolic syndrome, insulin resistance, hyperglycemia, impaired glucose utilization or tolerance, impaired or reduced insulin synthesis, a hyperlipidemia condition, such as hyperlipidemia, hypercholesterolemia, hypertriglyceridemia, elevated free fatty acids, or macrovascular damage, such as arterial atherosclerosis, hypolipidemias or vascular atherosclerosis. Hypercholesterolemia includes hyper-LDL cholesterolemia or elevated LDL cholesterol. Hypolipidemias include hypo-HDL cholesterolemia or low HDL cholesterol levels. Type 1 diabetes includes Immune-Mediated Diabetes Mellitus and Idiopathic Diabetes Mellitus. Type 2 diabetes includes forms with predominant or profound insulin resistance, predominant insulin deficiency and some insulin resistance and forms intermediate between these.

Solid state forms of Compound 1 can also be used to treat diseases or conditions associated with neuroinflammation such as Alzheimer's disease, Parkinson's disease, amyotrophic lateral sclerosis and age-related macular degeneration.

An "excipient", "carrier", "pharmaceutically acceptable carrier" or similar terms mean one or more component(s) or ingredient(s) that is acceptable in the sense of being compatible with the other ingredients in compositions or formulations comprising Compound 1 as the active pharmaceutical ingredient that is in solid state form when admixed with the excipients. These excipients usually are not overly deleterious to a subject to whom the composition formulation is to be administered. Excipients include one or more components typically used in the pharmaceutical formulation arts, e.g., one, two or more of fillers, binders, disintegrants, dispersants, preservatives, glidants, surfactants and lubricants. Exemplary excipients include povidone, crospovidone, corn starch, carboxymethyl cellulose, hydroxypropyl methylcellulose, microcrystalline cellulose, gum arabic, polysorbate 80, butylparaben, propylparaben, methylparaben, BHA, EDTA, sodium lauryl sulfate, sodium chloride, potassium chloride, titanium dioxide, magnesium stearate, castor oil, olive oil, vegetable oil, buffering agents such as sodium hydroxide, monobasic sodium phosphate, dibasic sodium phosphate, potassium hydroxide, monobasic potassium phosphate, dibasic potassium phosphate, tribasic potassium phosphate, potassium carbonate, potassium bicarbonate, ammonium hydroxide, ammonium chloride, saccharides such as mannitol, glucose, fructose, sucrose or lactose.

A "subject" means a human or an animal. Usually the animal is a mammal or vertebrate such as a non-human primate dog or rodent.

A "surface-active agent" (surfactant) means a substance, which, at low concentrations, interacts between the surfaces of a solid and fluid in which the solid is insoluble or sparingly soluble. The fluid may be a liquid excipient present in a suspension formulation comprising a solid state form of an active pharmaceutical ingredient, such as a crystalline form of Compound 1, the liquid excipient and the surface active agent that acts to improve suspendability. Alternatively, the surface active agent may be present in an oral solid dosage form comprising a polymorph or pseudopolymorph of Compound 1 (e.g., crystalline Form I, Form II, Form III or Form IV), the amorphous form of Compound 1 or a mixture thereof and the surface active agent, which acts to improve dissolution rate of the active pharmaceutical ingredient in the gastric fluid. Surface-active agents are amphipathic in structure having both polar (hydrophilic) and non-polar (hydrophobic) regions in the same molecule. Examples of surface active agents used in the formulation arts are given in Corrigan, O. I.; Healy, A. M. "Surfactants in Pharmaceutical Products and Systems" in *Encyclopedia of Pharmaceutical Technology* $2^{nd}$ ed. Taylor and Francis, 2006, pp. 3583-3596.

A "suspension" generally refers to a solid state form of Compound 1 that is present, usually as a finely divided (e.g., micronized) solid, in a liquid carrier (vehicle) at a time prior to administration of the suspension. The suspension may be either ready to use or a dry powder reconstituted as a suspension dosage form just prior to use. Suspensions typically include a suspending or flocculating agent, a wetting agent, if the suspending or flocculating agent that is present does not already serve this purpose, a buffering agent and a preservative. In a colloidal suspension, the Compound 1 particles are typically less than about 1 µm in size. In a coarse suspension, they are larger than about 1 µm. The practical upper limit for individual suspendable Compound 1 particles in coarse suspensions is about 50 µm to 75 µm although some proportion of particles up to 200 µm may be suitable dependent upon the syringeability of the suspension. Design considerations for developing a suspension for oral or parenteral administration are given in Akers, et al. *J. Parenteral Sci. Tech.* 1987 Vol. 41, pp. 88-96; Nash, R A "Suspensions" in Encyclopedia of Pharmaceutical Technology $2^{nd}$ ed. Taylor and Francis, 2006, pp 3597-3610 (which is hereby incorporated herein by reference with specificity into the present application).

Characterization and Identification Methods for Solid State Forms

Morphology—Crystal morphology refers to the symmetry in a crystal as exhibited by its crystal faces due to the ordered internal arrangement of atoms in the crystal structure. Crystal morphology of a particular crystalline form is sometimes described by the crystalline form's crystal system, namely, triclinic, monoclinic, orthorhombic, tetragonal, hexagonal or isometric. More typically, crystal morphology of crystals in a sample of crystalline material refers to the physical appearance of the majority of the crystals in the sample and is indicated by a shape descriptive label such as blades, plates, tablets, needles, etc. Crystal morphology may be determined by observation, for example by microscopic evaluation under at about 2×, 10×, 40× or 100× magnification using normal or polarized light.

X-Ray Powder Diffraction—X-Ray powder diffraction (XRPD) is typically used to characterize or identify crystalline compounds (see, e.g., U.S. Pharmacopoeia, volume 23, 1995, method 941, pp. 1843-1845, U.S.P. Pharmacopeia Convention, Inc., Rockville, Md.; Stout et al, X-Ray Structure Determination; A Practical Guide, MacMillan Co., New York, N.Y. 1968). When an X-ray beam interacts with a crystalline form a diffraction pattern is typically produced characterized by sequences of intensity maximums at positions that depend on lattice features of the crystalline form. Thus, the positions and the relative intensity of the XRPD lines are indicative of a particular crystalline form that provide a "fingerprint" that is often specific for a given crystalline form, although weak or very weak diffraction peaks may not always appear in replicate diffraction patterns obtained from successive batches of crystals. This is particularly the case if other crystalline forms are present in the sample in appreciable amounts, e.g., when a polymorph or pseudopolymorph form has become partially hydrated, dehydrated, desolvated or heated to give a significant amount of another polymorph or pseudopolymorph form.

Furthermore, the relative intensities of bands, particularly at low angle X-ray incidence values (low 2θ), may vary due to preferred orientation effects arising from differences in, e.g., crystal habit, particle size and other conditions of measurement. Thus, one typically looks to the relative positioning of the peaks coupled with their amplitude. Broad XRPD peaks, which may consist of two or more individual peaks located closely together, may be produced by amorphous components, disordered crystalline forms or parasitic scatter from the main beam. Broad peaks for different samples of the same solid state form are generally located within about 0.3-1 degree 2θ. Sharp isolated XRPD peaks for different samples of the same solid state form are usually found for normal resolution data within about 0.1 2θ degrees or occasionally within about ±0.2 2θ degrees on successive XRPD analyses. Thus, when a sharp isolated XRPD peak at a given position is identified as being located at, e.g., about 16.1 or 16.07 this means that the peak is at 16.1±0.1 or 16.07±0.1. When a broad XRPD peak at a given position is identified as being located at about a given degree 2θ value, this means that the peak is at that degree 2θ value±0.3.

An XRPD pattern may be described by "Prominent Peaks". Prominent peaks are selected from observed peaks by identifying preferably non-overlapping, low-angle peaks. A prominent peak will have relative intensity of at least about 5% or more typically at least about 10% or at least about 15% or at least about 20% relative intensity in comparison to the most intense peak in the X-ray diffraction pattern. Sometimes one or more peaks of intensity lower than 5% may be considered prominent are used in addition with one or more peaks that are more prominent (i.e. at least about 10% or at least about 15% or at least about 20% relative intensity) in order to describe an XRPD pattern for a crystalline form of 17α-ethynyl-androst-5-ene-3β,7β,17β-triol.

Under reproducible intra-lab conditions using the same instrument and protocol to obtain the XRPD patterns, the differences in XRPD peak locations and intensities obtained from successive XRPD analyses on different samples of the same solid state form having the same degree of crystallinity are due primarily to differences in sample preparation or the purity of the sample.

It is usually not necessary to rely on all peaks that one observes in a purified polymorph or pseudopolymorph sample disclosed herein, since even a single band may be diagnostic of a given polymorph or pseudopolymorph form of Compound 1. Rather, identification should typically focus on peak position and general pattern, particularly on the selection of prominent peaks to distinguish the various polymorph and pseudopolymorph forms described herein. Typically, an individual polymorph or pseudopolymorph form of Compound 1 is described by reference to the 2, 3 or 4 most intense peaks or to 2, 3 or 4 prominent peaks and optionally by reference to one or two other physical or analytical properties. Those properties include melting point, one or more thermal transitions observed in differential thermal analysis (DTA) or differential scanning calorimetry (DSC), percent weight loss in TGA occurring within a defined range of temperature, one or more absorption peaks observed in infrared or Raman spectroscopy and intrinsic dissolution rate (DR). Standardized methods for obtaining XRPD, DTA, DSC, DR, etc. data have been described for example in U.S. Pharmacopoeia, volume 23, 1995, United States Pharmacopeial Convention, Inc., Rockville, Md., pp 2292-2296 and 2359-2765 (incorporated herein by reference).

One method to identify a known polymorph or pseudopolymorph form within a suspected solid state sample, such as a solid state formulation comprising the known polymorph or pseudopolymorph form, involves obtaining one or more XRPD patterns from sample(s) containing the known polymorph or pseudopolymorph form, which are then compared with the XRPD patterns of the suspected solid state sample using, for example, a heuristic clustering analysis method as described for example in US Pat. Appl. Publ. No. 2004/0103130 (incorporated herein by reference particularly at paragraphs 0067-0078 and paragraphs 0086-0115 inclusive). Heuristic clustering analysis may also be used for quantitative analysis of samples containing either mixed crystalline phases (e.g., mixture of two or more polymorph forms) or mixed crystalline and disordered phases (e.g. mixture of a polymorph and amorphous forms) as described for example in US Pat. Appl. Publ. No. 2004/0103130 (incorporated herein by reference, particularly at paragraphs 0116-0130 inclusive).

Comparisons of atomic pairwise distribution functions (PDFs) derived from XRPD patterns may also be used to identify a known polymorph or pseudopolymorph in a suspected solid state sample, such as a solid state formulation comprising the known polymorph or pseudopolymorph form. If two crystalline forms are of the same molecule with the same molecular packing, their PDFs will be essentially the same. To determine if two PDFs derived from, for example, a known polymorph form or pseudopolymorph form and a solid state formulation suspected of containing these crystalline forms are essentially identical, the PDFs are compared by, for example, the method described in US Pat. Appl. Publ. No. 2007/0243620 (incorporated herein by reference).

If high resolution XRPD pattern(s) of an essentially pure polymorph or pseudopolymorph may be obtained, then unit cell parameters (as described in the section on single crystal X-ray analysis) may be determined for the crystalline form by an indexing method as, for example, in US Pat. Appl. Publ. No. 2007/0270397 (incorporated herein by reference). For a pseudopolymorph, if an isostructural crystalline form (i.e., a reference crystalline form), such as an isostructural anhydrate, which may be derived from dehydration and/or desolvation of the pseudopolymorph, may be obtained, then comparison of the unit cell volume of the isostructural crystalline form with the unit cell volume determined from high resolution XRPD pattern(s) may allow determination of the stoichiometry of the pseudopolymorph (i.e., number of water or solvent molecules per molecule of Compound 1). In such applications, the unit cell parameters for the reference isostructural crystalline form may be obtained from single crystal X-ray analysis or derived from indexing of high resolution XRPD data for this reference form.

Indexing may also be used to determine if a solid state form of Compound 1 contains a given crystalline form essentially free of other crystalline forms. This may be done by comparing the allowed reflections of the unit cell determined by an aforementioned indexing method with the peaks of the experimentally derived XRPD pattern taking into account those peaks that would be absent due to destructive interference. The presence of one or more prominent peaks in the experimental XRPD not allowed by the indexing solution indicates the presence of one or more other crystalline forms of Compound 1.

Vibrational Spectroscopy—Diagnostic techniques that one can optionally use to characterize crystalline forms of Compound 1, such as a polymorph or pseudopolymorph form, include vibrational spectroscopy techniques such as IR and Raman, which measure the effect of incident energy on a solid state sample due to the presence of particular chemical bonds within molecules of the sample that vibrate in response to the incident energy. Because polymorphs and pseudopolymorph form may possess different IR and Raman characteristics from each other, IR and Raman spectrum provide complementary information and either may provide a fingerprint for identification of a particular polymorph. [see, Anderton, C. *Eur. Pharm. Rev.*, Vol. 9, pp. 68-74 (2004)].

Raman is capable of determining polymorph or pseudopolymorph identity and/or quantification in a complex matrix, such as a tablet formulation, and of distinguishing between amorphous and crystalline forms or differentiating between multiple polymorphic and pseudo polymorphic forms of Compound 1 [for example, see Pratiwia, D., et al. "Quantitative analysis of polymorphic mixtures of ranitidine hydrochloride by Raman spectroscopy and principal components analysis" *Eur. J. Pharm. Biopharm.* Vol. 54, No. 3, pp. 337-341 (2002)]. For formulations containing a mixture of crystalline forms, recognition of about 10% polymorphic or pseudopolymorphic impurity of Compound 1 (representing an absolute detection limit of about 0.05% w/w), is sometimes possible.

For determining polymorph or pseudopolymorph identity or quantification of a crystalline form of Compound 1 within a complex matrix such as a solid formulation using the above vibrational spectroscopy methods, the technique of attenuated total reflectance (ATF) is sometimes used (for an example see Salari, H., et al. "Application of attenuated total reflectance FTIR spectroscopy to the analysis of mixtures of pharmaceutical polymorphs" *Intl. J. Pharm.*, Vol. 163, No. 1, pp. 157-166 (1998)].

Another technique for identification or quantification of crystalline material, such as a crystalline form of Compound 1 is Diffuse Reflectance Infrared Fourier Transform Spectroscopy (DRIFTS) (for an example see Tantishaiyakul, V., et al. "Use of DRIFTS and PLS for the Determination of Polymorphs of Piroxicam alone and in combination with pharmaceutical excipients: A Technical Note" *AAPS PharmSciTech*, Vol. 9, No. 1, pp. 95-99 (2008)].

In yet another technique, near-infrared (NIR) spectroscopy may also be used in identification or quantitative analysis of a crystalline form, such as a polymorphs or pseudo polymorph form (e.g., hydrate) of Compound 1 in a mixture of solid state forms or identification of a polymorph or pseudopolymorph form in a solid formulation such as a tablet containing the polymorph or pseudopolymorph form of Compound 1.

Overlap of IR or Raman bands from different crystalline forms of Compound 1 examined by various vibration spectroscopy methods may sometimes occur so that identification or quantification requires deconvolution methods to extract information for each individual component. Such deconvolution methods include partial least squares regression, principle component analysis or other methodologies [for examples, see Reich, G. "Near-infrared spectroscopy and imaging: Basic principles and pharmaceutical applications" *Adv. Drug Deliv. Rev.*, Vol. 57, pp. 1109-43 (2005)].

Solid State Nuclear Magnetic Resonance (SS-NMR)—Diagnostic techniques that one can optionally use to characterize polymorphs of Compound 1 include solid state NMR techniques [for examples see Tishmack, P. A., et al. "Solid-State Nuclear Magnetic Resonance Spectroscopy: Pharmaceutical Applications," *J. Pharm. Sci*. Vol. 92, No. 3, pp. 441-474 (2003)]. These techniques offer the advantage of being nondestructive and noninvasive. SS-NMR spectroscopy is sometimes suitable for testing drug formulations, such as those comprising Compound 1, because the NMR resonances for most pharmaceutical excipients occur in a narrow range of the NMR spectrum.

SS-NMR may also be applied to analyzing solid formulations comprising Compound 1 and thus may be useful for detecting different solid state forms of Compound 1 in the presence of excipients. For detecting amorphous Compound 1 in a solid state sample of Compound 1 the detection limit for SS-NMR is expected to be about 10-20%, depending on the relative location of the peaks form amorphous and crystalline forms in their spectra, because amorphous peaks generally are very broad. This is about the same detection limit for XRPD. In addition, because NMR spectroscopy is inherently a quantitative technique (i.e., signal intensity is relative to the number of nuclear sites at that specific resonance frequency), SS-NMR spectroscopy may allow one to determine the contribution of crystalline forms of Compound 1, or of crystalline and amorphous Compound 1, in a mixture of such forms.

Thermal Analysis Procedures—Diagnostic techniques that one can optionally use to characterize polymorphs of Compound 1 include differential thermal analysis (DTA), differential scanning calorimetry (DSC), thermogravimetric analysis (TGA) and melting point measurements.

DTA and DSC measure thermal transition temperatures at which a crystalline form absorbs or releases heat when its crystal structure changes or it melts. TGA is used to measure thermal stability and the fraction of volatile components of a sample by monitoring the weight change as the sample is heated. If infrared spectroscopy is conducted on the volatile components outgassed during TGA analysis of a pseudopolymorph (TGA-IR), then the molecular composition of the pseudopolymorph can be determined. These techniques are thus useful for characterizing solid state forms existing as solvates and/or hydrates.

DTA involves heating a test sample of a solid state form of Compound 1 and an inert reference under identical conditions while recording any temperature difference between the sample and reference.

DSC measures the energy needed to establish a nearly zero temperature difference between a sample and an inert reference as they are subjected to identical heating regimes.

Thermal transition temperatures observed in DSC and DTA typically occur within about 2° C. or ±2° C. on successive analyses using a temperature scan rate of 10° C./min and may occur within about 1° C. or ±1° C. depending on the temperature scan rate used (with slower scan rates such as 5° C./min or 1° C./min sometimes providing greater precision). When a sample of Compound 1 has a DSC or DTA transition at a given value, it means that the DSC or DTA transition will usually be within about 2° C. or ±2° C. for that sample for a sharp transition such as an sharp endotherm peak. For broad transitions, a temperature transition refers to the center of the peak (for exothermic transitions or valley (for endothermic transitions) of that transition. For broad transitions, particularly those resulting from dehydration or desolvation, successive analyses using a temperature scan rate of 10° C./min may occur within about 3° C. or ±3° C. or more for very broad transitions. Different crystalline forms including polymorph or pseudopolymorph forms may be identified, at least in part, based on their different transition temperature profiles in their DSC or DTA thermographs.

Thermal analysis is usually conducted at a temperature scan rate of 10° C./min. Lower scan rates such as 5° C./min or 1° C./min may be used if overlap of temperature transitions is suspected. Thus, a suspected transition due to a change in polymorph form to a different, more stable polymorph prior to complete melting of the sample may be discerned using a slower scan rate. A transition during thermal analysis of a kinetically formed polymorph to a thermodynamically more stable polymorph prior to complete melting may be avoided using a faster scan rate that does not allow time for the transition to occur.

Data Acquisition for Characterization and Identification Methods

Data provided in various Figures, Tables and Examples were obtained using the following methods and instrumentation.

X-Ray Powder Diffraction—XRPD patterns were obtained using one of the following methods. A PANalytical X'Pert Pro diffractometer. An incident beam of Cu Kα radiation was produced using an Optix long, fine-focus source. An elliptically graded multilayer mirror was used to focus the Cu Kα X-rays of the source through the specimen and onto the detector. A beam-stop and a helium atmosphere were used to minimize the background generated by air scattering. Soller slits were used for the incident and diffracted beams to minimize axial divergence. Prior to the analysis, a silicon specimen (NIST SRM 640c) was analyzed to verify the Si 111 peak position. Diffraction patterns were collected using a scanning position-sensitive detector (X'Celerator) located 240 mm from the specimen. Data were collected and analyzed using X'Pert Pro Data Collector software (v. 2.2b). The specimen was sandwiched between 3 μm thick films, analyzed in transmission geometry, and rotated to optimize orientation statistics.

XRPD patterns were also collected using an Inel XRG-3000 diffractometer equipped with a curved position sensitive detector with a 2θ range of 120°. An incident beam of Cu Kα radiation (40 kV, 30 mA) was used to collect data in real time at a resolution of 0.03° 2θ starting at about 4° 2θ. The monochromator slit was set at 5 mm by 160 μm. Prior to the analysis, a silicon standard (NIST SRM 640c) was analyzed to verify the Si 111 peak position. Diffraction radiation was detected by a sodium iodide scintillation detector. Samples were analyzed for 300 sec. Samples were prepared for analysis by packing them into thin-walled glass capillaries. Each capillary was mounted onto a goniometer head and rotated during data acquisition.

XRPD patterns were also obtained on a Shimadzu WRD-6000 X-ray powder diffractometer with Cu Kα radiation. The instrument was equipped with a long fine focus X-ray tube and a curved graphite monochromator. The tube voltage and amperage were set to 40 kV and 40 mA, respectively. The divergence and scattering slits were set at 1° and the receiving slit was set at 0.15 mm. Prior to the analysis, a silicon standard (NIST SRM 640c) was analyzed to verify the Si 111 peak position. Diffraction radiation was detected by a sodium iodide scintillation detector. Data were collected and analyzed using XRD-6100/7000 software (v. 5.0). Samples were prepared for analysis by placing them in a silicon zero-background holder.

X-ray diffraction patterns presented herein are accompanied by labeled peaks and/or tables with peak lists. Reported peak data, under most circumstances, is within the range of up to about 30° 2θ. Rounding algorithms were sometimes used to round each peak to the nearest 0.1° or 0.01° 2θ, depending upon the instrument used to collect the data and/or the inherent peak resolution.

The location of reported peaks along the x-axis (degree 2θ) in the figures and the tables were automatically determined using PATTERNMATCH™ 2.4.0 software and rounded to one or two significant figures after the decimal point based upon the above criteria. Peak position variability is given to within ±0.1° 2θ based upon recommendations outlined in the USP discussion of variability in X-ray powder diffraction given in United States Pharmacopeia, USP 31, NF 26, Vol. 1, p. 374. For d-space listings, the wavelength used to calculate d-spacings was 1.541874 Å, a weighted average of the Cu-$K_{\alpha1}$ and Cu-$K_{\alpha2}$ wavelengths [*Phys. Rev.*, Vol. A56, No. 6, pp. 4554-4568 (1997)]. Variability associated with d-spacing estimates was calculated from the USP recommendation at each d-spacing and is provided in the respective data tables.

Differential Scanning Calorimetry (DSC)—DSC was performed using a TA Instruments Q2000 differential scanning calorimeter. Temperature calibration was performed using NIST traceable indium metal. The sample was placed into an aluminum DSC pan, and the weight was accurately recorded. The pan was covered with a lid perforated with a laser pinhole, and the lid was crimped. A weighed, crimped aluminum pan was placed on the reference side of the cell. The sample cell was equilibrated at 25° C., in some cases cooled to −30° C. and heated under a nitrogen purge at a rate of 10° C./minute, up to a final temperature of 300° C. Indium metal was used as the calibration standard. Reported temperatures are at the transition maxima. For studies on glass transition temperature ($T_g$) of amorphous material, the sample was equilibrated at −20° C., and then heated under nitrogen at a rate of 1° C./min., up to 160° C. The $T_g$ is reported from the inflection point of the transition.

Differential Thermal Analysis (DTA)—DTA were performed simultaneously using a Seiko SSC 5200 TG/DTA instrument. Temperature calibration was performed using NIST traceable indium metal. The sample was placed into an aluminum pan and loosely covered with a lid and the weight accurately recorded. The sample cell was equilibrated at 25° C. and then heated under a nitrogen purge at a rate of 10° C./minute, up to a final temperature of 300° C. Reported temperatures are at the transition maxima.

Thermogravimetric Analysis (TGA)—TGA was performed using a TA Instruments Q5000 IR thermogravimetric analyzer or simultaneously with DTA/DSC a Seiko SSC 5200 TG/DTA instrument. Temperature calibration was performed using nickel and ALUMEL™. Each sample was placed in an aluminum/or/platinum pan. The pan was hermetically sealed with a lid that was opened using a punching mechanism just before being inserted into the TG furnace. The furnace was heated under nitrogen at a rate of 10° C./minute to a final temperature of 350° C.

Thermogravimetric-Infrared (TG-IR) Analysis—TG-IR was preformed on a TA Instruments thermogravimetric (TG) analyzer model 2050 interfaced to a Magna-IR 560™ Fourier transform infrared (FT-IR) spectrophotometer (Thermo Nicolet) equipped with an Ever-Glo mid/far IR source, a potassium bromide (KBr) beam splitter and a mercury cadmium telluride (MCT-A) detector. The FT-IR wavelength verification was performed using polystyrene, and the TG calibration standards were nickel and Alumel™. The sample was placed in a platinum sample pan, and the pan was inserted into the TG furnace. The TG instrument was started first, immediately followed by the FT-IR instrument. The TG instrument was operated under a flow of helium at 90 and 10 cc/min. for the purge and balance, respectively. The furnace was heated under nitrogen at a rate of 20° C./minute to a final temperature of 250° C. IR spectra were collected approximately every 32 seconds for approximately 13 minutes. Each IR spectrum used 32 co-added scans collected at a spectral resolution of 4 $cm^{-1}$. Volatiles were identified from a search of the High Resolution Nicolet Vapor Phase spectral library.

FT-Raman Spectroscopy—Raman spectra were acquired on a Nexus 670 FT-Raman accessory module interfaced to a Nexus 670 FT-IR spectrophotometer (Thermo Nicolet) equipped with an indium gallium arsenide (InGaAs) detector. Wavelength verification was performed using sulfur and cyclohexane. Each sample was prepared for analysis by placing the sample into a glass tube and positioning the tube in a gold-coated tube holder. Approximately 0.5 W of Nd:YVO$_4$ laser power (1064 nm excitation wavelength) was used to irradiate the sample. Each spectrum used 256 co-added scans collected at a spectral resolution of 4 $cm^{-1}$.

Raman spectra were also acquired on a Nexus 670 FT-Raman accessory module interfaced to a Nexus 670 FT-IR spectrophotometer (Thermo Nicolet) equipped with an indium gallium arsenide (InGaAs) detector. Wavelength verification was performed using sulfur and cyclohexane. Each sample was prepared for analysis by placing the sample into a glass tube and positioning the tube in a gold-coated tube holder.

Formulations—Formulations comprising Compound 1 as the active pharmaceutical ingredient will have a significant percentage of Compound 1 in one or more of its solid state forms, typically in one or two solid state forms. Exemplary formulations contain at least about 60% or usually at least about 90% of Compound 1 in one solid state form. Formulations will usually comprise one or more given solid state forms of Compound 1, substantially free of other solid state forms, and one or more, typically 1, 2, 3 or 4 excipients or carriers. Other formulations can contain Compound 1 in one or more solid state forms, typically one or two. Other formulations are generally solids, precipitates, gels, suspensions and colloids that contain one or more solid state forms of Compound 1, such as the amorphous form of Compound 1, crystalline Form I or crystalline Form III of Compound 1 or a mixture thereof. Preferred formulations use a single crystalline form with Form I preferred. Preferred oral unit dosages for human use will contain about 2 mg, 5 mg, 10 mg, 15 mg, 20 mg or 40 mg of a solid state form of Compound 1 per unit dose, with 2 mg, 5 mg and 10 mg unit doses preferred in treating chronic inflammation conditions in humans and unit doses of 15 mg and 20 mg preferred for treating acute inflammation conditions in humans.

While it is possible to administer Compound 1 in its solid state as a pure compound to a subject, it is usually presented as a solid formulation essentially free of liquid or less frequently a solid suspension. Formulations will typically be used to prepare unit dosages, e.g., tablets, capsules or lozenges for oral, buccal or sublingual administration. Alternatively, embodiments include a formulation for parenteral (e.g., subcutaneous, subdermal, intravenous, intramuscular, intraperitoneal or aerosol) administration made by the process of contacting a solid state form of Compound 1, such as amorphous Compound 1, or a crystalline form of Compound 1 (e.g., Form I), with a liquid excipient, e.g., any one, two, three or more of water, buffered aqueous solution, PEG 100, PEG 200, PEG 300, PEG 400, propylene glycol, benzyl benzoate, benzyl alcohol or ethanol, and optionally sterilizing the solution and optionally dispensing the solution into vials or ampoules (typically amber glass), which may be single-use or multi-use and optionally storing the formulation at reduced temperature (about 0-12° C., or about 2-10° C.). Such formulations optionally may also be used for oral administration and optionally may contain one or more of a salt, buffer or bacteriostat or preservative (e.g., NaCl, BHA, BHT or EDTA). Sometimes a surface active agent is used to affect a suspension or is incorporated into an oral solid dosage form to assist dissolution of the solid state form of Compound 1, e.g., Form I, into the gastric tract. In general, formulations for oral administration are preferred for human therapeutic applications with solid oral formulations particularly preferred.

Surface active agents used in a suspension or a solid form of Compound 1 in a liquid excipient(s) include nonionic, cationic and anionic surfactants. Examples of preferred surfactants include, but are not limited to, a lauryl sulfate, sodium dodecyl sulfate, polysorbate 40 and polysorbate 80.

In one embodiment, sodium lauryl sulfate is used as a surface active agent in a unit dosage form, such as a tablet or a capsule, for oral administration in treatment of a condition disclosed herein wherein the formulation comprises crystalline Form I essentially free of other solid state forms of Compound 1 and the surface active agent, optionally comprising one or more additional excipients.

Micronization—To improve dissolution rate of a crystalline form of Compound 1 in a formulation comprising at least one crystalline form of Compound 1 and one or more pharmaceutically acceptable excipients in a solid dosage form or to affect suspendability in a suspension for oral or parenteral administration comprising a crystalline form of Compound 1 and a liquid excipient(s), the crystalline form may be milled to an mean volume weighted particle size (Dv, 50) or average diameter of about 0.01-200 μm, or about 0.1-100 μm or preferably about 3-50 μm. Mean volume weighted particle size (Dv, 50) or average diameter for milled crystalline Compound 1 may thus be relatively small, e.g., about 0.1-1.0 µm, or somewhat larger, e.g., about 3-100 µm. Milled crystalline Compound 1 is suitable for preparing solid and suspension formulations intended for oral or parenteral administration to a subject. Preferably, mean volume weighted particle size (Dv,50) or average diameter are about 5, about 10, about 15 or about 20 micron. The particle size (Dv, 90) typically is about 5 micron, about 10, about 15, about 20, about 25 or about 30 micron. Preferred particle size has (Dv, 90) of ≤10 microns or (Dv, 90) of about 7 microns.

Micronization methods include milling by ball mills, pin mills, jet mills (e.g., fluid energy jet mills) and grinding, sieving and precipitation of a compound(s) from a solution, see, e.g., U.S. Pat. Nos. 4,919,341; 5,202,129; 5,271,944; 5,424,077 and 5,455,049 (all of which are specifically incorporated herein by reference). Particle size is determined by, e.g., transmission electron microscopy, scanning electron microscopy, light microscopy, X-ray diffractometry and light scattering methods or Coulter counter analysis (see, for example, "Characterization of Bulk Solids" D. McGlinchey, Ed., Blackwell Publishing, 2005).

Thus, crystalline Compound 1 may comprise or consist essentially of a powder that contains one, two or more of these mean volume weighted particle sizes or average diameter particle sizes and the powder may be contacted with a solid excipient(s), which can be mixed and optionally compressed or formed into a desired shape. Alternatively, crystalline Compound 1 formed into a powder a described above is contacted with a liquid excipient(s) to prepare a liquid formulation or a liquid composition that is incorporated into a solid formulation or suspension. Suitable micronized formulations thus include aqueous or oily suspensions of crystalline Compound 1.

Dosing Protocols or Methods—n treating any of the conditions or symptoms disclosed herein, one can continuously (daily) or intermittently administer the compositions or formulations comprising a crystalline or amorphous form of Compound 1 to a subject suffering from or susceptible to the condition or symptom, preferably administering a formulation comprising Form I.

Dosages of Compound 1 in solid state form administered by the routes described herein and the use of combination therapies with other standard therapeutic agents or treatments could be applied essentially as described above for any of the diseases or conditions that are disclosed herein. Thus, the Compound 1 in solid state form may be administered prophylactically or therapeutically in chronic conditions or they may be administered at the time of or relatively soon after an acute event such as a pain flare associated with a condition being treated. Prophylactic administration is used to reduce expected incidence or severity of an event, e.g., a multiple sclerosis, arthritis or asthma flare.

Preparation Methods of Solid State Forms

Crystalline forms of 17α-ethynyl-androst-5-ene-3β,7β, 17β-triol described in the Examples were obtained using one or more of the following methods.

Fast Evaporation (FE): Saturated solutions of Compound 1 were prepared in various solvents as shown in Table 5 at ambient temperature. The solutions were filtered into clean vials and allowed to evaporate under ambient conditions, uncapped.

Very Fast Evaporation (VFE): A solution of Compound 1 was prepared in ethanol at elevated temperature. The sample was filtered into a clean petri dish and nitrogen was blown over the sample to facilitate drying. The solids were collected and immediately analyzed.

Slow Evaporation (SE): Saturated solutions of Compound 1 were prepared in various solvents as shown in Table 5 at ambient temperature. The solutions were filtered into clean vials and these vials were covered with aluminum foil. The foil was perforated with small holes and allowed to evaporate under ambient conditions.

Slow Cool (SC): Saturated solutions of Compound 1 were prepared in various solvents as shown in Table 5 at elevated temperature. The solution was immediately filtered into a warm vial. The vial was sealed and allowed to slowly cool. Solids that formed were isolated by vacuum filtration and allowed to dry under ambient conditions.

Ambient Temperature or Elevated Temperature Slurry: Samples of Compound 1 were prepared in various solvents as shown in Table 5 so that excess solids were present in each vial. The mixtures were agitated in a closed vial at either ambient temperature or at elevated temperature using an orbital shaker. After several days the solids were isolated by vacuum filtration and allowed to dry under ambient conditions.

Crash Cooling (CC): Saturated solutions of Compound 1 were prepared in various solvents as shown in Table 5 at either ambient or elevated temperatures. The samples were thermally shocked by quickly placing them at sub-ambient temperatures. After several minutes, vials were checked for precipitation. In the absence of precipitation, the vials were stored sub-ambient. Resulting solids were isolated by vacuum filtration and typically air-dried at ambient temperature.

Crash Precipitation (CP): Solutions of Compound 1 were prepared in various solvents as shown in Table 5 at either elevated or ambient temperature. The solutions were quickly filtered into vials containing room temperature anti-solvent in order to induce solid formation. After several minutes, vials were checked for precipitation. In the absence of precipitation, the vials were stored sub-ambient. Resulting solids were isolated by vacuum filtration and typically air-dried at ambient temperature.

Liquid Vapor Diffusion (LVD): Saturated solutions of Compound 1 were prepared in various solvents as shown in Table 5 at ambient temperature. The solutions were filtered into clean vials and placed uncapped in a larger vial that contained a diffusing solvent. The larger vial was capped and left at ambient conditions for several days. Resulting solids were isolated by vacuum filtration and air-dried at ambient temperature.

Sonication: Super saturated solutions of Compound 1 were prepared at ambient temperatures. The samples were briefly subjected to probe sonication (Cole-Parmer Ultrasonic processor with 3-mm probe). The samples were capped and left at ambient temperature for nucleation/solid growth. Solids that were formed after sonication were immediately isolated and dried under ambient conditions.

Numbered embodiments. Some preferred aspects of the invention and related subject matter include the following numbered embodiments.

1. A solid-state form of 17α-ethynyl-androst-5-ene-3β,7β, 17β-triol wherein the solid-state form is crystalline 17α-ethynyl-androst-5-ene-3β,7β,17β-triol substantially free of 17α-ethynyl-androst-5-ene-3β,7β,17β-triol in amorphous form.

2. The solid-state form of embodiment 1 wherein the crystalline 17α-ethynyl-androst-5-ene-3β,7β,17β-triol is Form I 17α-ethynyl-androst-5-ene-3β,7β,17β-triol essentially free of amorphous 17α-ethynyl-androst-5-ene-3β,7β, 17β-triol and optionally substantially free of other crystalline forms of 17α-ethynyl-androst-5-ene-3β,7β,17β-triol. In this embodiment Form I Compound 1 is optionally characterized by an X-ray powder diffraction pattern having three or four of degree 2-theta values selected from the group consisting of 10.4, 16.2, 17.8 and 28.8 and optionally with one or more degree 2-theta values selected from the group consisting of 12.6, 15.1, 16.7 and 27.3. One description of Form I Compound 1 has degree 2-theta values of 10.4, 16.2, 17.8 and 28.8 and optionally with a degree 2-theta value of 15.0 or 27.3. Another description of Form I Compound 1 has degree 2-theta values of 10.4, 16.2, 17.8 and 28.8 and optionally with a degree 2-theta value of 16.1 and 27.3. Another exemplary description of Form I Compound 1 has degree 2-theta values of 16.2, 17.8, 28.8 and 15.1.

3. The solid-state form of embodiment 1 wherein the crystalline 17α-ethynyl-androst-5-ene-3β,7β,17β-triol is Form I 17α-ethynyl-androst-5-ene-3β,7β,17β-triol characterized by a X-ray powder diffraction pattern substantially identical to the X-ray powder diffraction pattern of FIG. 1, FIG. 2 or FIG. 3 and optionally a differential scanning calorimetry and thermogravimetric analysis thermograms substantially identical to the differential scanning calorimetry and thermogravimetric analysis thermograms of FIG. 4.

Figure 5A:
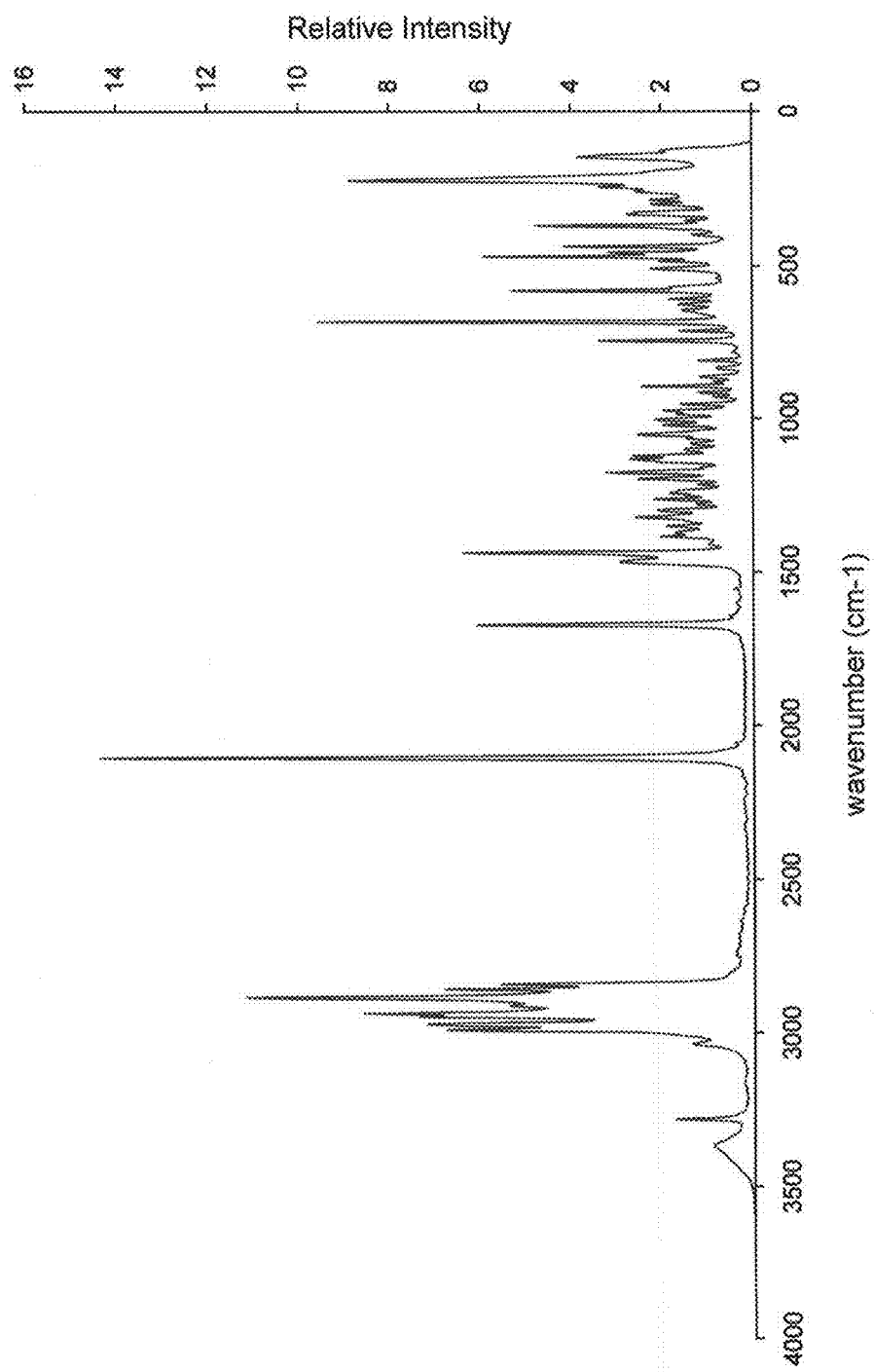
FIG. 5A is a Raman spectroscopy spectrum with expanded region for a sample containing crystalline Form I 17α-ethynyl-androst-5-ene-3β,7β,17β-triol.
Figure 5B:
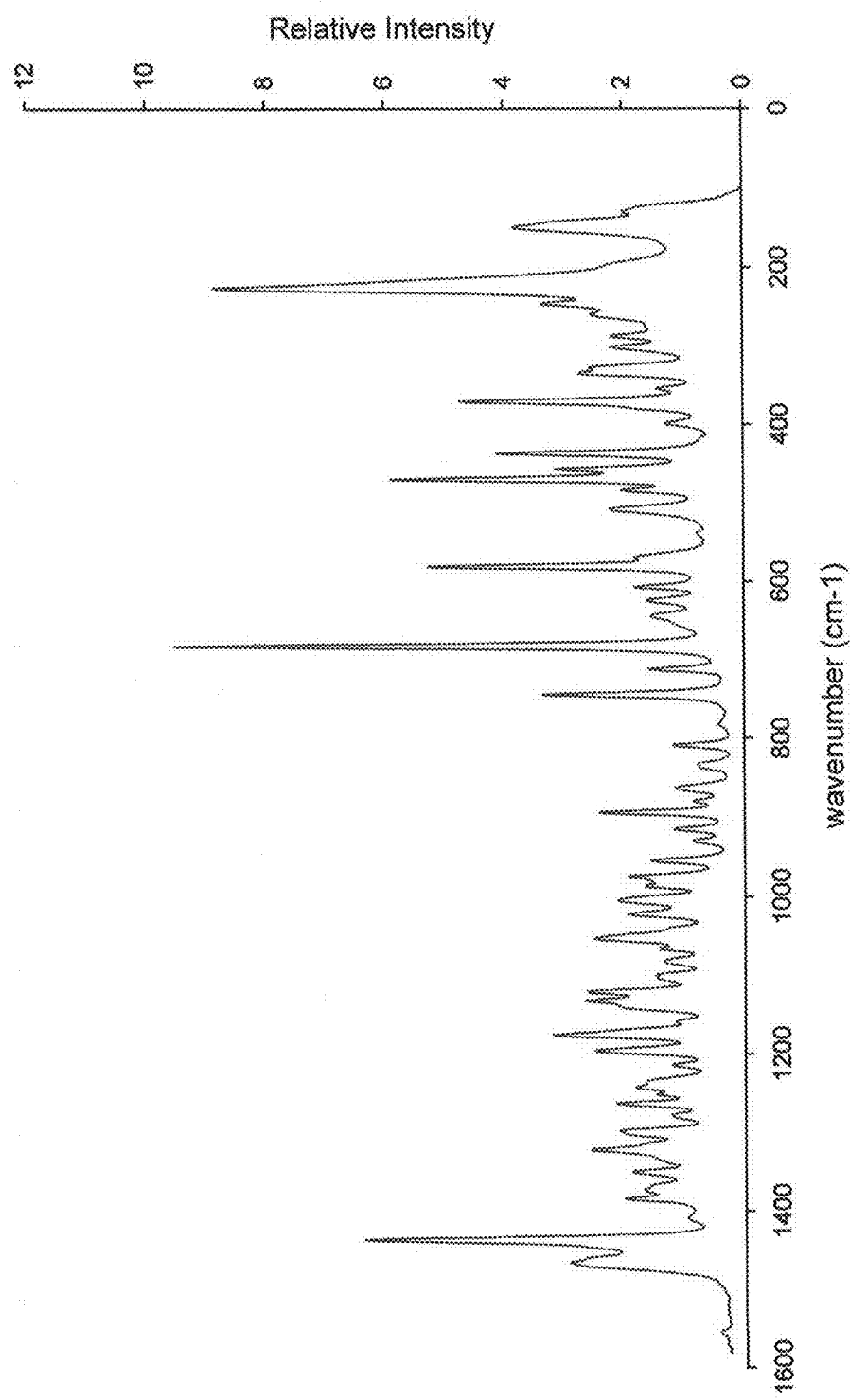
FIG. 5B is a Raman spectroscopy spectrum for a sample containing crystalline Form I 17α-ethynyl-androst-5-ene-3β,7β,17β-triol.

4. The solid-state form of embodiment 1, 2 or 3 characterized by or further characterized by a Raman spectrum substantially identical to the Raman spectrum of FIG. 5. In this embodiment Form I Compound 1 is characterized by one, two or three Raman absorptions selected from the group consisting of 2993, 2974, 2947, 2937, 2887, 2860 and 2843 cm$^{-1}$; optionally with one two or three absorptions selected from the group consisting of 2106, 1674, 1467 and 1437 cm-1 or one, two or three absorptions selected from the group consisting of 744, 712, 683, 484, 471, 457, 438, 247 and 226 cm$^{-1}$. One description of Form I Compound 1 has Raman absorptions at 2887, 2106, 1674, 1437 and 712 cm$^{-1}$ and optionally an absorption at 247 or 226 cm$^{-1}$. Another description of Form I Compound 1 has Raman absorptions at 2887, 2106, 1674, 1437, 712 and 683 cm$^{-1}$ and optionally an absorption at 484, 471 or 457. Another exemplary description of Form I Compound 1 has Raman absorptions at 2106, 1674, 1437, 712 and 683 cm$^{-1}$ and optionally with an absorption at 1467 cm$^{-1}$.

5. The solid-state form of embodiment 1 wherein the crystalline 17α-ethynyl-androst-5-ene-3β,7β,17β-triol is Form II 17α-ethynyl-androst-5-ene-3β,7β,17β-triol essentially free of amorphous 17α-ethynyl-androst-5-ene-3β,7β,17β-triol and optionally substantially free of other crystalline forms of 17α-ethynyl-androst-5-ene-3β,7β,17β-triol. In this embodiment Form II Compound 1 is optionally characterized by an X-ray powder diffraction pattern having one, two or three degree 2-theta values selected from the group consisting of 2.5, 5.0 and 7.6 and two or more degree 2-theta values selected from the group consisting of 10.4, 16.2, 17.8 and 28.8. One description of Form II Compound 1 has degree 2-theta values of 2.5, 5.0 and 16.2 and optionally with a degree 2-theta value of 10.4 or 28.8. Another description of Form II Compound 1 has degree 2-theta values of 2.5, 16.2 and 28.8 and optionally with a degree 2-theta value of 10.4 or 17.8. Another exemplary description of Form II Compound 1 has degree 2-theta values of 2.5, 5.0, 10.4, 16.2, 17.8 and 28.8.

Figure 6A:
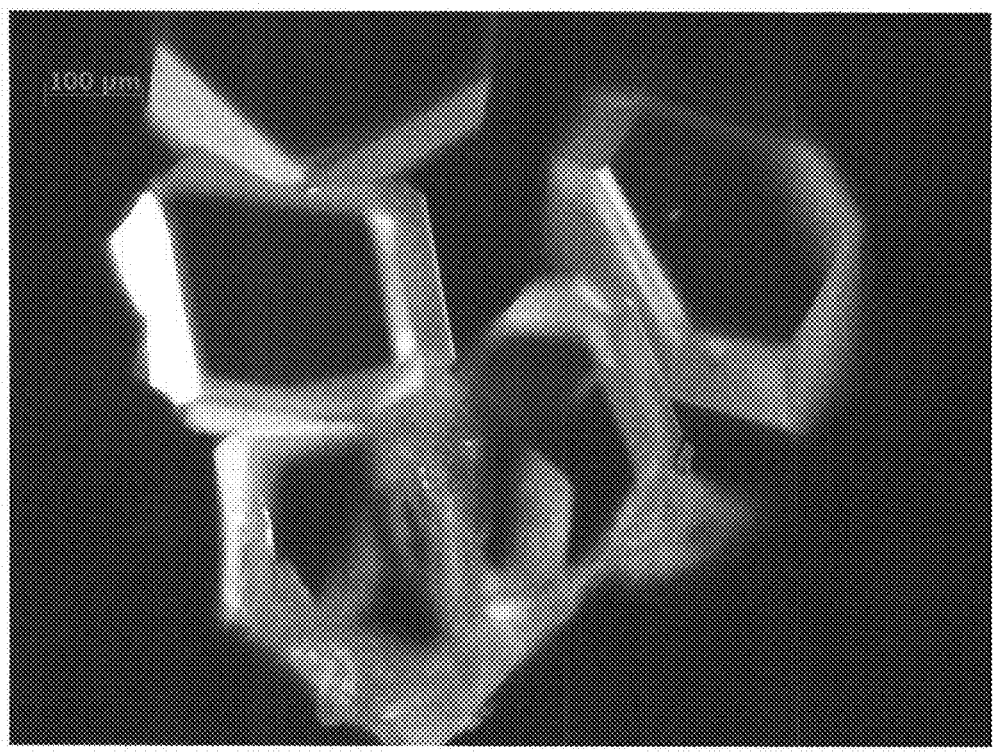
FIGS. 6A and 6B are microscope photographs of crystals of crystalline Form I 17α-ethynyl-androst-5-ene-3β,7β,17β-triol under 10× magnification.
Figure 6B:
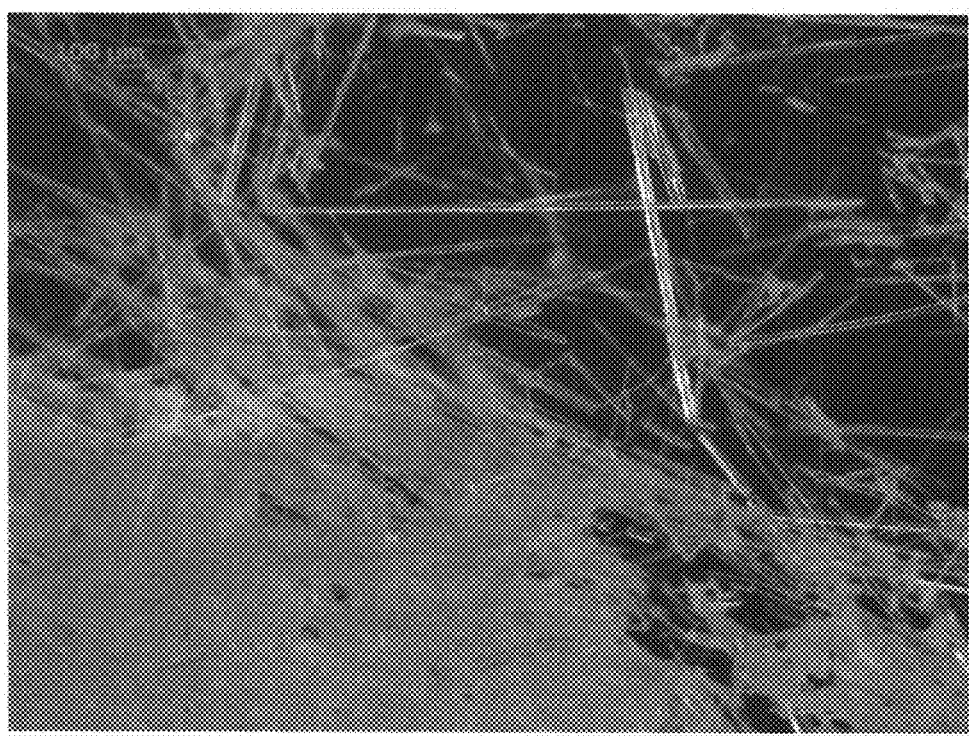

6. The solid-state form of embodiment 1 wherein the crystalline material is Form II 17α-ethynyl-androst-5-ene-3β,7β,17β-triol characterized by a X-ray powder diffraction pattern substantially identical to the X-ray powder diffraction pattern of FIG. 6 and optionally a differential scanning calorimetry and thermogravimetric analysis thermograms substantially identical to the differential scanning calorimetry and thermogravimetric analysis thermograms of FIG. 7.

7. The solid-state form of embodiment 1 wherein the crystalline 17α-ethynyl-androst-5-ene-3β,7β,17β-triol is Form III 17α-ethynyl-androst-5-ene-3β,7β,17β-triol essentially free of amorphous 17α-ethynyl-androst-5-ene-3β,7β, 17β-triol and optionally free of other crystalline forms of 17α-ethynyl-androst-5-ene-3β,7β,17β-triol. In this embodiment Form III Compound 1 is optionally characterized by an X-ray powder diffraction pattern having two or three degree 2-theta values selected from the group consisting of 15.2, 15.7, 16.6 and optionally with one or more degree 2-theta values selected from the group consisting of 8.3, 12.3, 18.4 and 27.8. One description of Form III Compound 1 has degree 2-theta values of 15.2, 16.6 and 27.8 and optionally with a degree 2-theta value of 8.3 or 12.3. Another description of Form III Compound 1 has degree 2-theta values of 15.2, 16.6 and 27.8 and optionally with a degree 2-theta value of 8.3 or 12.3. Another exemplary description of Form III Compound 1 has degree 2-theta values of 15.2, 15.7, 16.6 and 27.8.

8. The solid-state form of embodiment 1 wherein the crystalline material is Form III 17α-ethynyl-androst-5-ene-3β,7β,17β-triol characterized by a X-ray powder diffraction pattern substantially identical to the X-ray powder diffraction pattern of FIG. 11 and optionally a differential scanning calorimetry and thermogravimetric analysis thermograms substantially identical to the differential scanning calorimetry and thermogravimetric analysis thermograms of FIG. 12.

Figure 13A:
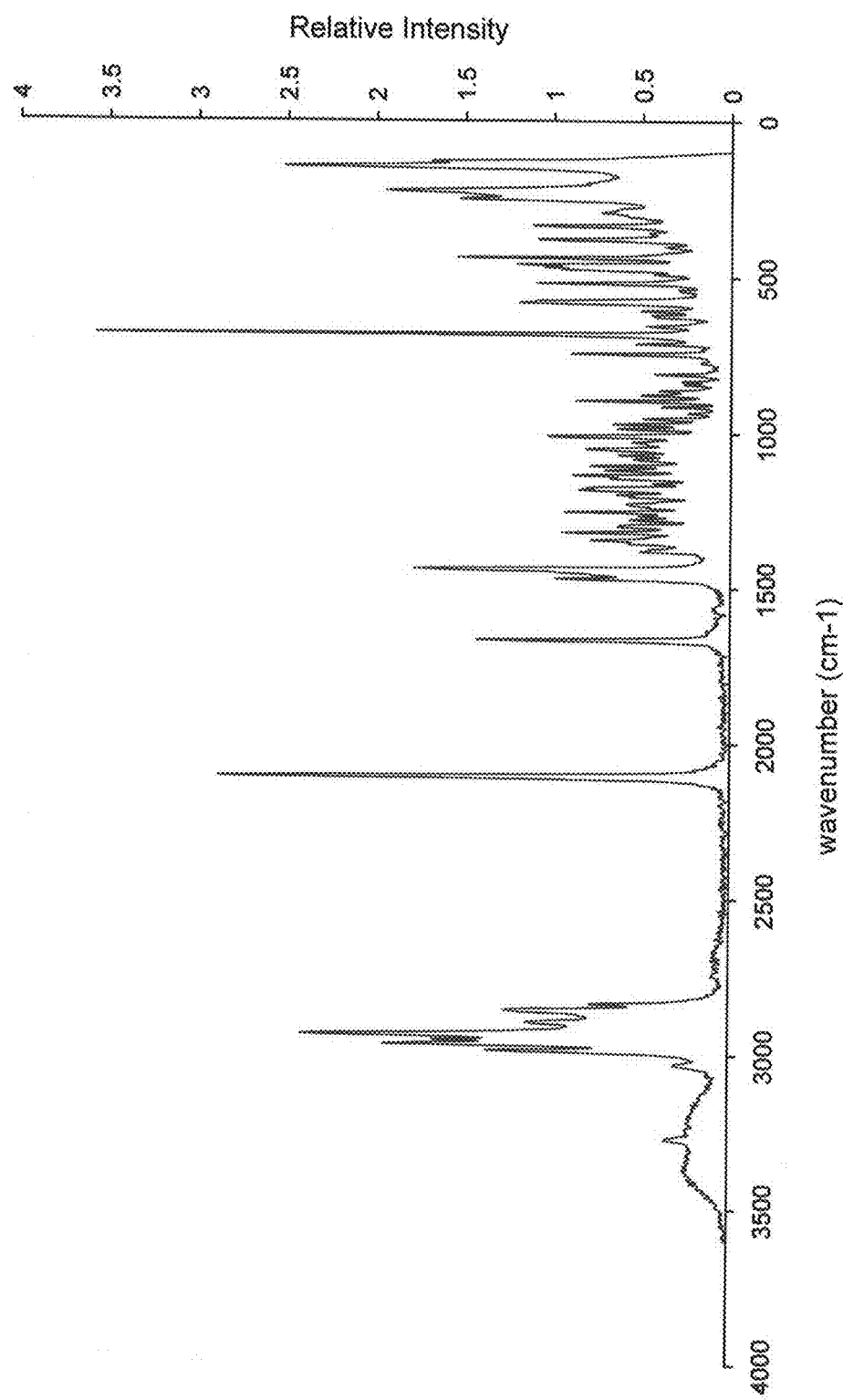
FIG. 13A is a Raman spectrum with expanded region for a sample containing crystalline Form III 17α-ethynyl-androst-5-ene-3β,7β,17β-triol.
Figure 13B:
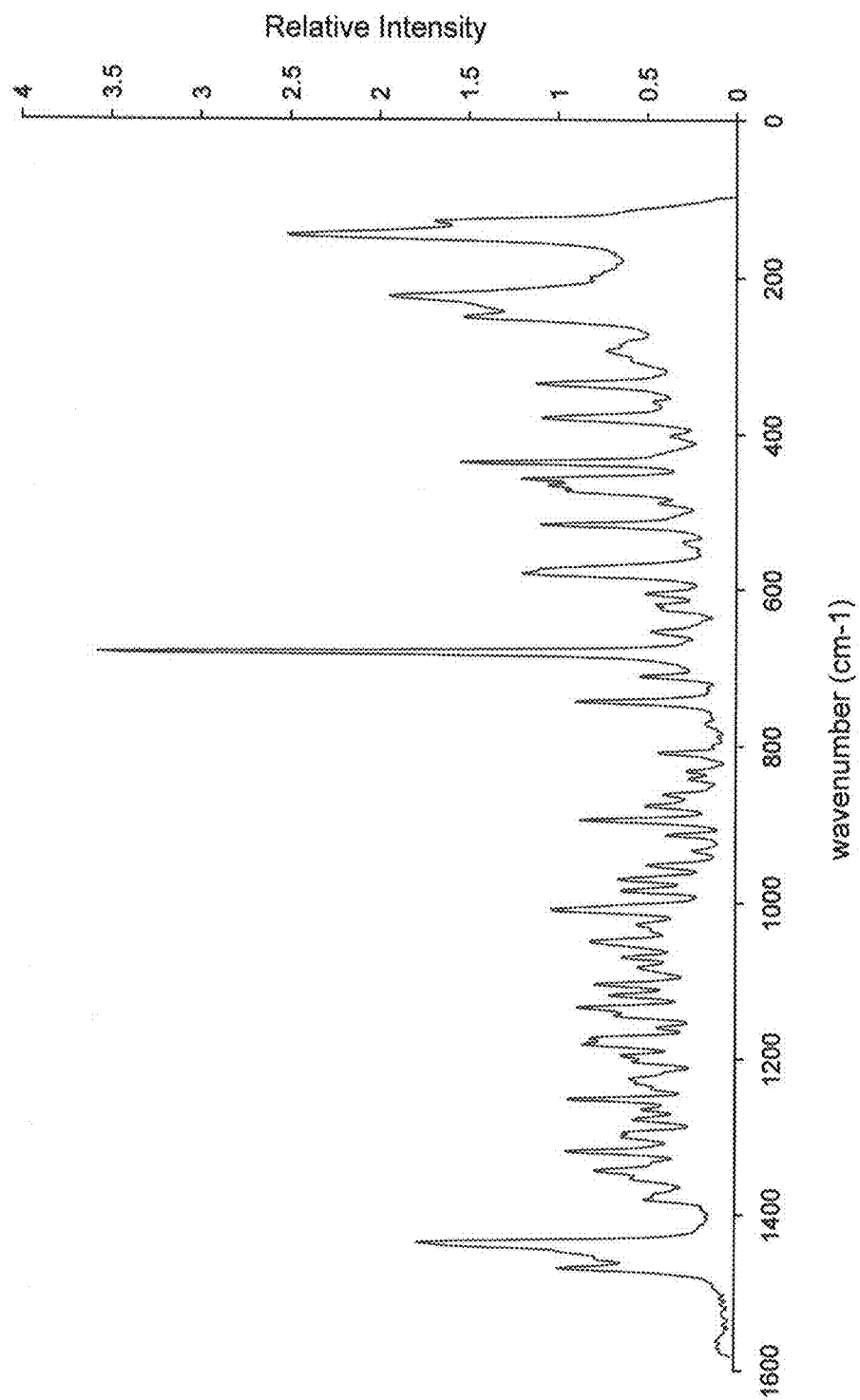
FIG. 13B is a Raman spectrum for a sample containing crystalline Form III 17α-ethynyl-androst-5-ene-3β,7β,17β-triol.

9. The solid-state form of embodiment 1, 8 or 9 characterized by or further characterized by a Raman spectrum substantially identical to the Raman spectrum of FIG. 13. In this embodiment Form III Compound 1 is characterized by one, two or three Raman absorptions selected from the group consisting of 2985, 2966, 2950, 2933, 2893, 2853 and 2833 cm$^{-1}$; optionally with one two or three absorptions selected from the group consisting of 2108, 1666, 1469 and 1437 cm-1 or one, two or three absorptions selected from the group consisting of 711, 681, 457, 436, 251 and 224 cm$^{-1}$. One description of Form III Compound 1 has Raman absorptions at 2950, 2934, 2108, 1666, 1437 and 711 cm$^{-1}$ and optionally an absorption at 250 or 224 cm$^{-1}$. Another description of Form III Compound 1 has Raman absorptions at 2985, 2950, 2108, 1437, 1666, 711 and 681 cm$^{-1}$ and optionally an absorption at 457 or 436 cm$^{-1}$. Another exemplary description of Form III Compound 1 has Raman absorptions at 2108, 1666, 1437, 712 and 681 cm$^{-1}$ and optionally with an absorption at 1469 cm$^{-1}$.

10. The solid-state form of embodiment 1 wherein the crystalline material is Form IV 17α-ethynyl-androst-5-ene-3β,7β,17β-triol essentially free of amorphous 17α-ethynyl-androst-5-ene-3β,7β,17β-triol and optionally substantially free of other crystalline forms of 17α-ethynyl-androst-5-ene-3β,7β,17β-triol. In this embodiment Form IV Compound 1 is optionally characterized by an X-ray powder diffraction pattern having two or three degree 2-theta values selected from the group consisting of 15.1, 15.7, 16.6 and optionally with one or more degree 2-theta values selected from the group consisting of 8.3, 10.3, 12.3, 16.6 and 27.8. One description of Form IV Compound 1 has degree 2-theta values of 15.1, 16.6 and 27.8 and optionally with a degree 2-theta value of 8.3 or 12.3. Another description of Form IV Compound 1 has degree 2-theta values of 15.7, 16.6 and 27.8 and optionally with a degree 2-theta value of 8.3, 12.3 or 16.6. Another exemplary description of Form IV Compound 1 has degree 2-theta values of 8.3, 15.1, 15.7, 16.6 and 27.8.

11. The solid-state form of embodiment 1 wherein the crystalline material wherein the crystalline material is Form IV 17α-ethynyl-androst-5-ene-3β,7β,17β-triol characterized by a X-ray powder diffraction pattern substantially identical to the X-ray powder diffraction pattern of FIG. 14 and optionally a differential scanning calorimetry and thermogravimetric analysis thermograms substantially identical to the differential scanning calorimetry and thermogravimetric analysis thermograms of FIG. 15.

Figure 16A:
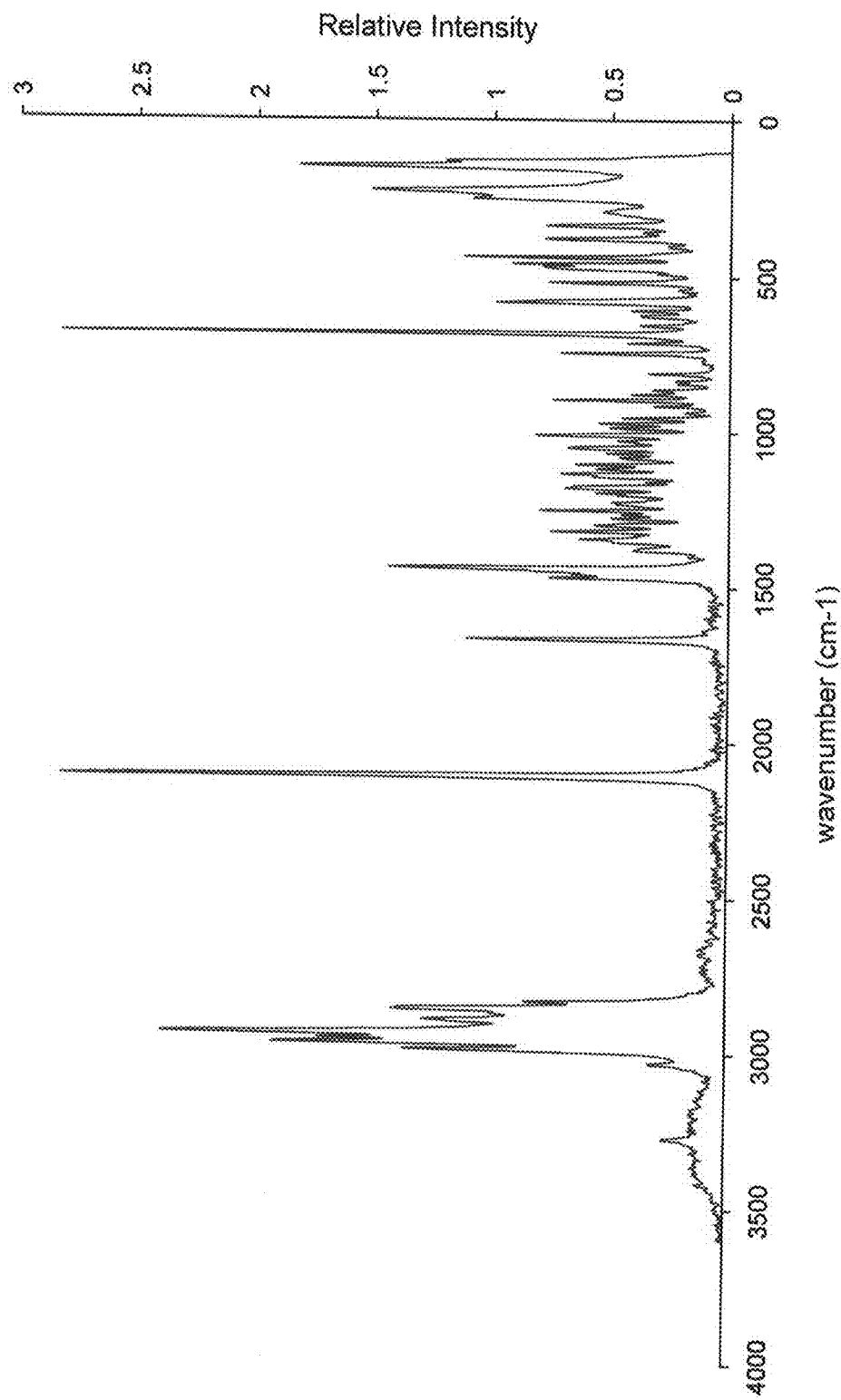
FIG. 16A is a Raman spectrum with expanded region for a sample containing crystalline Form IV 17α-ethynyl-androst-5-ene-3β,7β,17β-triol.

12. The solid-state form of embodiment 1, 10 or 11 characterized by or further characterized by a Raman spectrum substantially identical to the Raman spectrum of FIG. 16. In this embodiment Form IV Compound 1 is characterized by one, two or three Raman absorptions selected from the group consisting of 2985, 2966, 2950, 2933, 2891, 2858 and 2833 cm$^{-1}$; optionally with one, two or three absorptions selected from the group consisting of 2108, 1666, 1469 and 1437 cm$^{-1}$ or one, two or three absorptions selected from the group consisting of 711, 681, 467, 457, 436 and 224 cm$^{-1}$. One description of Form IV Compound 1 has Raman absorptions at 2950, 2933, 2108, 1666, 1437 and 711 cm$^{-1}$ and optionally an absorbtion at 1469 or 457 cm$^{-1}$. Another description of Form IV Compound 1 has Raman absorptions at 2985, 2950, 2108, 1666, 1437, 711 and 681 cm$^{-1}$ and optionally an absorption at 467 or 457 cm$^{-1}$. Another exemplary description of Form IV Compound 1 has Raman absorptions at 2108, 1666, 1437, 711 and 681 cm$^{-1}$ and optionally with an absorption at 1469 cm$^{-1}$.

13. A solid-state form of 17-ethynyl-androst-5-ene-3β,7β,17β-triol wherein the solid-state form is amorphous 17α-ethynyl-androst-5-ene-3β,7β,17β-triol substantially free of 17α-ethynyl-androst-5-ene-3β,7β,17β-triol in crystalline form.

14. The solid state form of embodiment 13 essentially free of crystalline 17-ethynyl-androst-5-ene-3β,7β,17β-triol and optionally characterized by a X-ray powder diffraction pattern substantially identical to the X-ray powder diffraction pattern of FIG. 17 and optionally by a reversible heat flow in a modulated differential scanning calorimetry thermogram substantially identical to the reversible heat flow shown in FIG. 18.

Figure 19A:
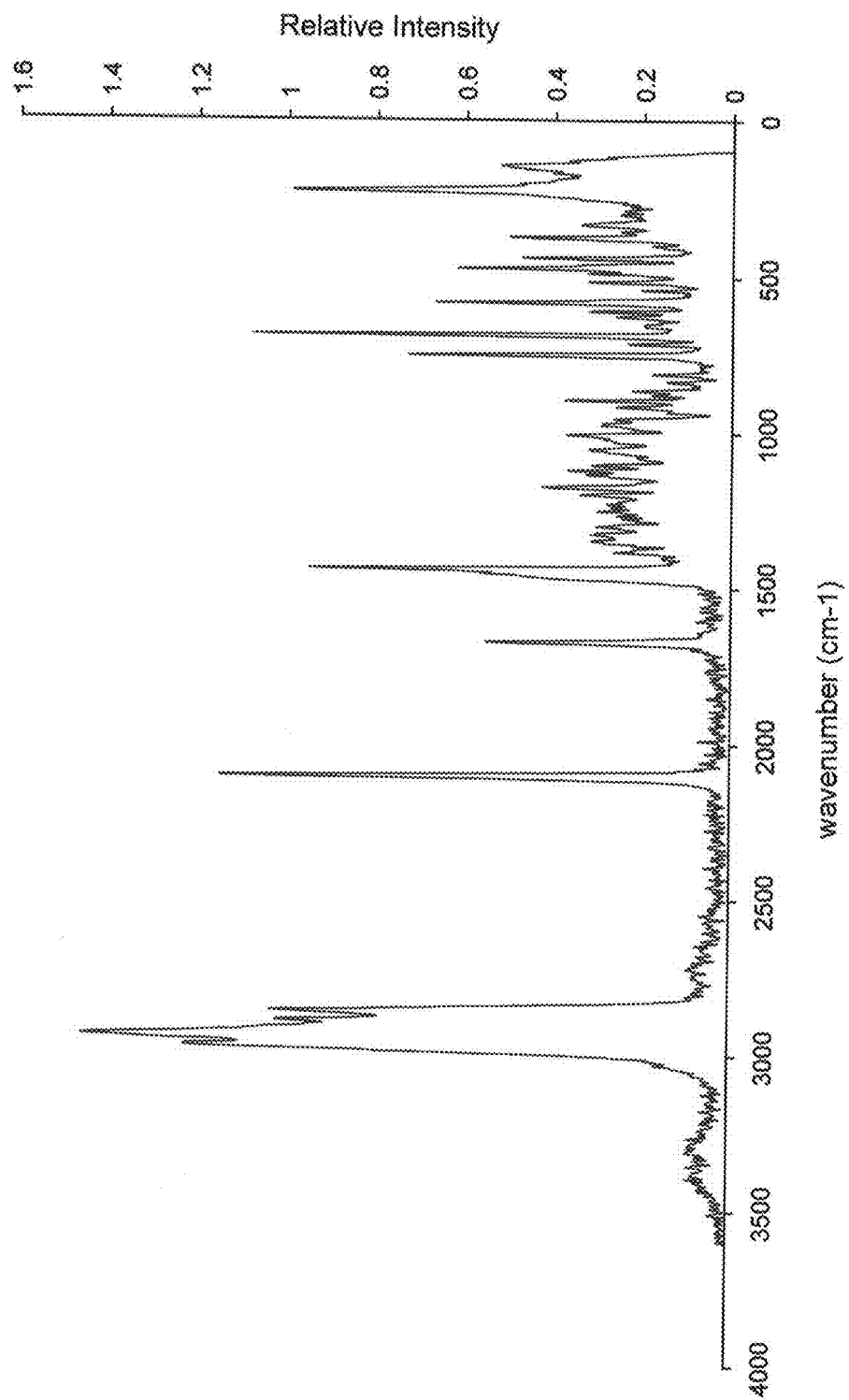
FIG. 19A is a Raman spectrum with expanded region for a sample containing amorphous 17α-ethynyl-androst-5-ene-3β,7β,17β-triol substantially free of crystalline 17α-ethynyl-androst-5-ene-3β,7β,17β-triol.
Figure 19B:
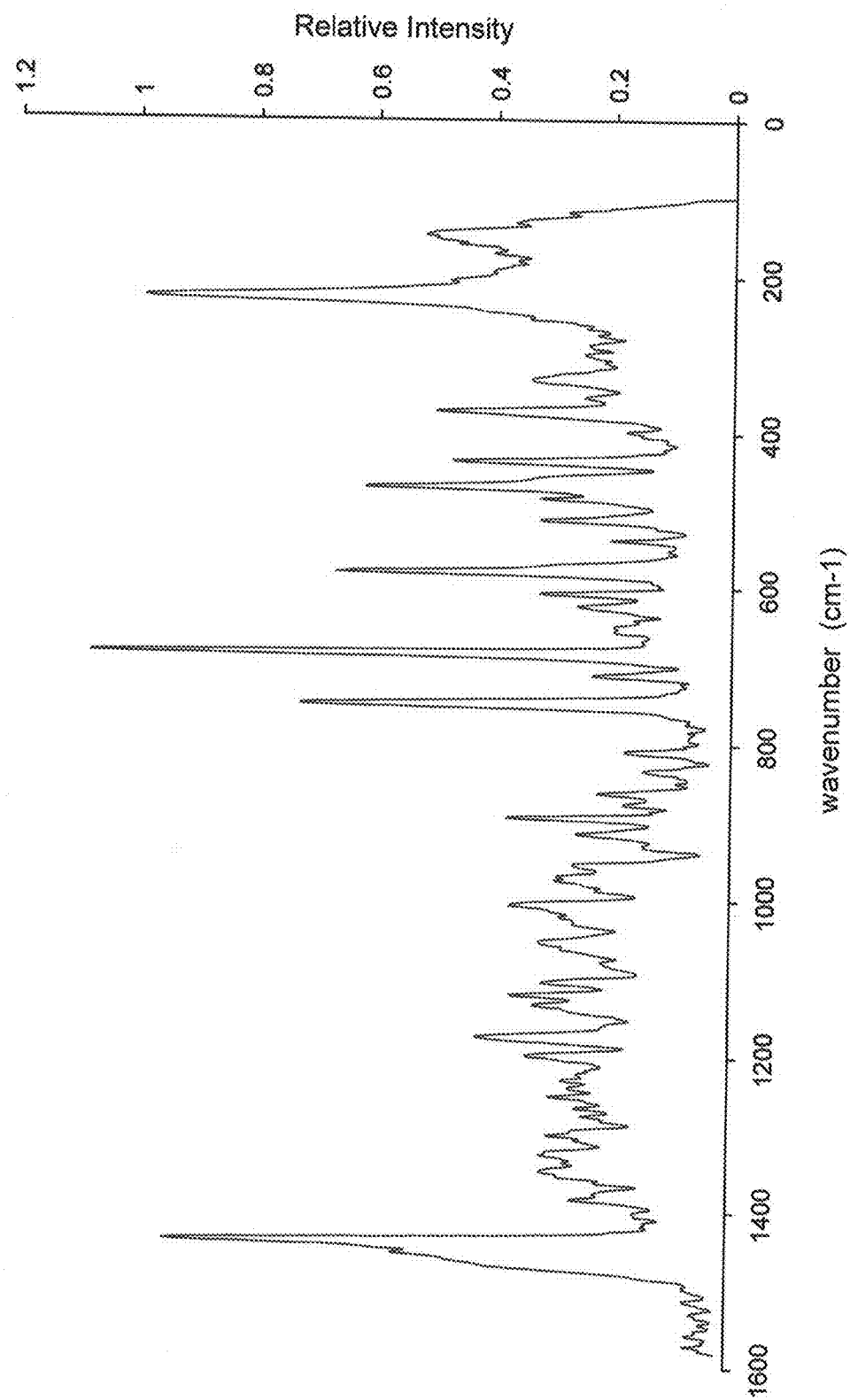
FIG. 19B is a Raman spectrum for a sample containing amorphous 17α-ethynyl-androst-5-ene-3β,7β,17β-triol substantially free of crystalline 17α-ethynyl-androst-5-ene-3β,7β,17β-triol.

15. The solid state form of embodiment 13 or 14 characterized by or further characterized by a Raman spectrum substantially identical to the Raman spectrum of FIG. 19. In this embodiment amorphous Compound 1 is characterized by one, two or three Raman absorptions selected from the group consisting of 2972, 2937, 2889 and 2858 cm$^{-1}$; optionally with one two or three absorptions selected from the group consisting of 2106, 1674 and 1439 cm-1 or one, two or three absorptions selected from the group consisting of 748, 684, 484, 470, 436 and 226 cm$^{-1}$. One description of amorphous Compound 1 has Raman absorptions at 2972, 2106, 1674, 1439 and 684 cm$^{-1}$ and optionally an absorption at 226 cm$^{-1}$. Another description of amorphous Compound 1 has Raman absorptions at 2937, 2106, 1674, 1439, 748 and 684 cm$^{-1}$ and optionally an absorption at 484, 470 or 436. Another exemplary description of amorphous Compound 1 has Raman absorptions at 2106, 1674, 1439 and 684 cm$^{-1}$ and optionally with an absorption at 748 cm$^{-1}$.

16. A formulation comprising a solid state form of 17α-ethynyl-androst-5-ene-3β,7β,17β-triol and at least one pharmaceutically acceptable excipient.

17. The formulation of embodiment 16 wherein said at least one pharmaceutically acceptable excipient is sodium dodecyl sulfate.

18. The formulation of embodiment 16 wherein the pharmaceutically acceptable excipients are sodium dodecyl sulfate, microcrystalline cellulose and magnesium stearate.

19. The formulation of embodiment 16, 17 or 18 wherein the solid state form is 17α-ethynyl-androst-5-ene-3β,7β,17β-triol in crystalline form.

20. The formulation of embodiment 19 wherein the crystalline form is essentially free of amorphous of 17α-ethynyl-androst-5-ene-3β,7β,17β-triol.

21. The formulation of embodiment 20 wherein the crystalline form is crystalline Form I essentially free of other crystalline forms of 17α-ethynyl-androst-5-ene-3β,7β,17β-triol.

22. The formulation of embodiment 16, 17 or 18 wherein the solid state form is 17α-ethynyl-androst-5-ene-3β,7β,17β-triol in amorphous form.

23. The formulation of embodiment 22 wherein the amorphous form is essentially free of 17α-ethynyl-androst-5-ene-3β,7β,17β-triol in crystalline form.

24. A method to treat an inflammation condition comprising administering to a human or mammal in need thereof an effective amount of a formulation comprising a solid state form of 17α-ethynyl-androst-5-ene-3β,7β,17β-triol and at least one pharmaceutically acceptable excipient.

25. The method of embodiment 24 wherein the inflammation condition is an inflammatory bowel condition.

26. The method of embodiment 24 wherein the inflammation condition is an inflammatory lung condition.

27. The method of embodiment 26 wherein the inflammatory lung condition is cystic fibrosis, asthma, bronchitis or chronic obstructive pulmonary disease.

28. A method to treat metabolic syndrome, impaired glucose tolerance (pre-diabetes) or a hyperglycemia condition comprising administering to a human or mammal in need thereof an effective amount of a formulation comprising a solid state form of 17α-ethynyl-androst-5-ene-3β,7β,17β-triol and at least one pharmaceutically acceptable excipient. In these embodiments, patients having metabolic syndrome are usually characterized as having three or more of the following five conditions: hypertension, abdominal obesity (a waist circumference of at least 102 cm in adult males and a waist circumference of at least 88 cm in adult females), low HDL cholesterol (less than 40 mg/dL in adult males and less than 50 mg/dL in adult females), elevated serum triglycerides (at least 150 mg/dL) and an elevated fasting plasma glucose (at least 100 mg/dL). Patients having impaired glucose tolerance are typically characterized as having a fasting plasma glucose level of 100 mg/dL to 125 mg/dL and/or a postprandial glucose level of 140-200, which is usually measured at 2 hours after ingestion of 75 g of anhydrous glucose in an oral glucose tolerance test. Patients having impaired glucose tolerance are typically considered pre-diabetic when postprandial glucose is 140-200 mg/dL. Impaired fasting glucose and impaired glucose tolerance identifies individuals at risk for developing overt diabetes mellitus over time. In preferred embodiments, the treatment method is for treatment of impaired glucose tolerance. In other preferred embodiments, the treatment method is for treatment of hyperglycemia.

29. The method of embodiment 28 wherein the hyperglycemia condition is type 1 diabetes or type 2 diabetes. Patients having diabetes that can be treated are typically characterized as having a fasting plasma glucose level of at least 126 mg/dL and/or a postprandial glucose level of at least 200 mg/dL. In preferred embodiments, the hyperglycemia condition is type 2 diabetes.

30. A method to treat inflammation associated with a hyperproliferation condition comprising administering to a human or mammal in need thereof an effective amount of a formulation comprising a solid state form of 17α-ethynyl-androst-5-ene-3β,7β,17β-triol and at least one pharmaceutically acceptable excipient.

31. The method of embodiment 30 wherein the hyperproliferation condition is breast cancer, prostate cancer or benign prostatic hyperplasia.

32. A method to treat a neurodegenerative condition comprising administering to a human or mammal in need thereof an effective amount of a formulation comprising a solid state form of 17α-ethynyl-androst-5-ene-3β,7β,17β-triol and at least one pharmaceutically acceptable excipient.

33. The method of embodiment 32 wherein the neurodegenerative condition is Alzheimer's disease, Parkinson's disease or Amyotrophic Lateral Sclerosis.

34. A method to treat an autoimmune condition comprising administering to a human or mammal in need thereof an effective amount of a formulation comprising a solid state form of 17α-ethynyl-androst-5-ene-3β,7β,17β-triol and at least one pharmaceutically acceptable excipient.

35. The method of embodiment 34 wherein the autoimmune condition is multiple sclerosis, rheumatoid arthritis, ulcerative colitis, Crohn's disease, Hashimotos' thyroiditis, Systemic Lupus Erythematosus or optic neuritis.

36. The method of any one of embodiments 24-35 wherein the solid state form is Form I 17α-ethynyl-androst-5-ene-3β,7β,17β-triol. In these embodiments the Form I 17α-ethynyl-androst-5-ene-3β,7β,17β-triol can be essentially free of amorphous 17α-ethynyl-androst-5-ene-3β,7β, 17β-triol, for example, when used in (a) the method of embodiment 25, 29 or 30 or (b) the method of embodiment 35 or 36.

37. The method of any one of embodiments 24-35 wherein the solid state form is Form I, Form II, Form III or Form IV 17α-ethynyl-androst-5-ene-3β,7β,17β-triol or a mixture thereof wherein the solid state form is essentially free of amorphous 17α-ethynyl-androst-5-ene-3β,7β,17β-triol. In these embodiments the Form I 17α-ethynyl-androst-5-ene-3β,7β,17β-triol can be essentially free of amorphous 17α-ethynyl-androst-5-ene-3β,7β,17β-triol, for example, when used in (a) the method of embodiment 25, 29 or 30 or (b) the method of embodiment 35 or 36.

38. The method of any one of embodiments 24-35 wherein the solid state form is amorphous 17α-ethynyl-androst-5-ene-3β,7β,17β-triol.

39. The method of any one of embodiments 24-35 wherein the solid state form is amorphous 17α-ethynyl-androst-5-ene-3β,7β,17β-triol wherein the solid state form is essentially free of 17α-ethynyl-androst-5-ene-3β,7β,17β-triol in crystalline form.

Other embodiments of the invention related to 17α-ethynyl-androst-5-ene-3β,7β,17β-triol in solid state form includes the following numbered embodiments.

1A. A solid state form of 17α-ethynyl-androst-5-ene-3β,7β,17β-triol.

2A. The solid-state form of embodiment 1A wherein the solid-state form is one or more crystalline forms of 17α-ethynyl-androst-5-ene-3β,7β,17β-triol substantially free of amorphous 17α-ethynyl-androst-5-ene-3β,7β,17β-triol.

3A. The solid-state form of embodiment 1A wherein solid-state form is a polymorph or pseudopolymorph of 17α-ethynyl-androst-5-ene-3β,7β,17β-triol.

4A. The solid-state form of embodiment 1A wherein the polymorph or pseudopolymorph of 17α-ethynyl-androst-5-ene-3β,7β,17β-triol is essentially free of amorphous 17α-ethynyl-androst-5-ene-3β,7β,17β-triol.

5A. The solid-state form of embodiment 1A wherein the solid-state form is a crystalline form of 17α-ethynyl-androst-5-ene-3β,7β,17β-triol and is essentially free of amorphous 17α-ethynyl-androst-5-ene-3β,7β,17β-triol.

6A. The solid-state form of embodiment 1A wherein the solid-state form is obtained from a slurry of 17α-ethynyl-androst-5-ene-3β,7β,17β-triol in methanol-water essentially as described in Example 1.

7A. The solid-state form of embodiment 1A wherein the solid-state form is obtained from a methanol-water solution essentially as described in Example 2.

8A. The solid-state form of embodiment 1A wherein the solid-state form is prepared by micronization essentially as described in Example 3.

9A. The solid-state form of embodiment 1A wherein the solid-state form is obtained from a tetrahydrofuran-methanol solution essentially as described in Example 4.

10A. The solid state form of embodiment 4A wherein the solid-state form is characterized by: (a) an X-ray powder pattern with degree 2-theta values of 10.41±0.1, 16.20±0.1 and 17.85±0.1 and optionally one or more degree 2-theta values of 12.68±0.1, 15.12±0.1, 16.72±0.1 and 20.91±0.1 and optionally with (b) differential scanning calorimetry (DSC) thermogram having a prominent endotherm at about 266° C. (onset at about 259° C.) obtained with a heating rate of 10° C./min or (c) TGA thermogram with negligible weight loss or ≤0.5% weight loss from about 30° C. to about 200° C., obtained with a heating rate of 10° C./min or is characterized by (a) and (b) or (a), (b) and (c).

11A. The solid-state form of embodiment 4A wherein the solid-state form is characterized by an X-ray powder diffraction pattern and differential scanning calorimetry (DSC) thermogram substantially identical to the X-ray powder diffraction pattern of FIG. 1, FIG. 2 or FIG. 3 and optionally with DSC-TGA thermograms of FIG. 4.

12A. The solid-state form of embodiment 4A, 10A or 11A characterized or further characterized by Raman spectrum substantially identical to FIG. 5A or FIG. 5B or a Raman spectroscopy spectrum with absorptions at peak positions of about 2106 and 1674 cm$^{-1}$, optionally with one, two or three absorptions with peak positions selected from the group consisting of 2947, 2887, 976, 507, 484, 470, 370, 301, 247 and 226 cm$^{-1}$.

13A. The solid-state form of embodiment 4A, 10A or 11A characterized or further characterized by crystals having the morphology of FIG. 6A or FIG. 6B.

14A. The solid state form of embodiment 4A wherein the solid-state form is characterized by: (a) an X-ray powder pattern with degree 2-theta values of 2.5, 5.0, 16.22±0.1 and optionally one or more 2-theta values of 7.6, 10.40, 12.66, 14.36, 15.08, 16.73, 17.75 and 18.29±0.1 and optionally by (b) DSC thermogram having a prominent endotherm at about 266° C. (onset at about 259° C.) or (c) TGA thermogram with negligible weight loss or ≤0.5% weight loss from about 30° C. to about 200° C., obtained with a heating rate of 10° C./min or is characterized by (a) and (b) or (a), (b) and (c).

15A. The solid-state form of embodiment 4A wherein the solid-state form is characterized by an X-ray powder diffraction pattern and differential scanning calorimetry (DSC) thermogram substantially identical to the X-ray powder diffraction pattern of FIG. 7 and DSC-TGA thermograms of FIG. 8.

16A. The solid state form of embodiment 4A wherein the solid-state form is characterized by: (a) an X-ray powder pattern with degree 2-theta values of 15.25, 15.64 and 16.60±0.1 and optionally one or more degree 2-theta values selected from the group consisting of 8.35, 12.31, 18.25, 20.08 and 27.82±0.1 and optionally with (b) DSC thermogram having a prominent sharp endotherm at about 266° C. (onset at about 258° C.) and a prominent broad endotherm centered at about 105° C., optionally with an endotherm at about 1.7° C. or (c) TGA thermogram with weight loss of about 9.6% from about 20° C. to about 100° C., obtained with a heating rate of 10° C./min or is characterized by (a) and (b) or (a), (b) and (c).

17A. The solid-state form of embodiment 4A wherein the solid-state form is characterized by an X-ray powder diffraction pattern and differential scanning calorimetry (DSC) thermogram substantially identical to the X-ray powder diffraction pattern of FIG. 11 and DSC-TGA thermograms of FIG. 12.

18A. The solid-state form of embodiment 4A, 16A or 17A characterized or further characterized by Raman spectrum substantially identical to FIG. 13A or FIG. 13B or a Raman spectroscopy spectrum with absorptions at peak positions of about 2108 and 1666 cm$^{-1}$, optionally with one, two or three absorptions with peak positions selected from the group consisting of 2950, 2933, 1469, 983, 681, 654, 517, 380, 251 and 224 cm$^{-1}$.

19A. The solid state form of embodiment 4A wherein the solid-state form is characterized by: (a) an X-ray powder pattern with two or more 2-theta values selected from the group consisting of 15.24, 15.66 and 16.62±0.1 and optionally with one or more 2-theta values of 8.34, 10.50, 12.30, 16.23 and 27.78±0.1 and optionally with (b) DSC thermogram having a prominent sharp endotherm at about 266° C. (onset at about 257° C.) and a broad endotherm centered at about 98° C., optionally with a sharp endotherm at about 79° C. or about 88° C. (c) TGA thermogram having about 9.0 or about 9.7 wt % weight loss from about 20° C. to about 110° C. obtained with a heating rate of 10° C./min or is characterized by (a) and (b) or (a), (b) and (c).

20A. The solid-state form of embodiment 4A wherein the solid-state form is characterized by an X-ray powder diffraction pattern and differential scanning calorimetry (DSC) thermogram substantially identical to the X-ray powder diffraction pattern of FIG. 14 and DSC-TGA thermograms of FIG. 15.

21A. The solid-state form of embodiment 4A, 19A or 20A characterized or further characterized by Raman spectrum substantially identical to FIG. 16A or a Raman spectroscopy spectrum with absorptions at peak positions of about 2108 and 1666 cm$^{-1}$, optionally with one, two or three absorptions with peak positions selected from the group consisting of 2950, 2933, 1469, 983, 681, 654, 577, 467, 380, 251 and 224 cm$^{-1}$.

22A. The solid-state form of embodiment 1A wherein the solid-state form is characterized by an X-ray powder diffraction pattern and differential scanning calorimetry (DSC) thermogram substantially identical to the X-ray powder diffraction pattern of FIG. 17 and modulated DSC thermogram of FIG. 18.

23A. The solid-state form of embodiment 1A or 23A characterized or further characterized by Raman spectrum substantially identical to FIG. 19A or FIG. 19B or a Raman spectrum with absorptions at peak positions of about 2105 and 1673 cm$^{-1}$; optionally with one, two or three peak positions selected from the group consisting of 2972, 2937, 684, 538, 484, 470, 372 and 226 cm$^{-1}$.

24A. The solid-state form of embodiment 23A wherein the solid-state form is amorphous 17α-ethynyl-androst-5-ene-3β,7β,17β-triol substantially free of 17α-ethynyl-androst-5-ene-3β,7β,17β-triol in crystalline form.

25A. The solid-state form of embodiment 1A wherein the solid-state form is amorphous 17α-ethynyl-androst-5-ene-3β,7β,17β-triol essentially free of 17α-ethynyl-androst-5-ene-3β,7β,17β-triol in crystalline form.

26A. A formulation comprising or prepared from a solid state form of 17α-ethynyl-androst-5-ene-3β,7β,17β-triol and at least one pharmaceutically acceptable excipient.

27A. The formulation of embodiment 26A wherein the solid state form is one or more crystalline forms of 17α-ethynyl-androst-5-ene-3β,7β,17β-triol.

28A. The formulation of embodiment 27A wherein said one crystalline form is a polymorph or pseudopolymorph form of 17α-ethynyl-androst-5-ene-3β,7β,17β-triol and is substantially free of 17α-ethynyl-androst-5-ene-3β,7β,17β-triol in amorphous form.

29A. The formulation of embodiment 27A wherein said one crystalline form is a polymorph or pseudopolymorph form of 17α-ethynyl-androst-5-ene-3β,7β,17β-triol and is essentially free of amorphous 17α-ethynyl-androst-5-ene-3β,7β,17β-triol.

30A. The formulation of embodiment 27A wherein the solid-state form is a single crystalline form of 17α-ethynyl-androst-5-ene-3β,7β,17β-triol essentially free of amorphous 17α-ethynyl-androst-5-ene-3β,7β,17β-triol.

31A. The formulation of embodiment 30A wherein said one single crystalline form is an anhydrate.

32A. The formulation of embodiment 30A wherein the single crystalline form is Form I.

33A. The formulation of embodiment 28A or 29A wherein said one crystalline form is a pseudopolymorph, optionally selected from the group consisting of crystalline Form III and Form IV.

34A. The formulation of embodiment 28A or 29A wherein said one crystalline form is Form I substantially free or essentially free of other crystalline forms of 17α-ethynyl-androst-5-ene-3β,7β,17β-triol.

35A. The formulation of embodiment 27A, 28A or 29A wherein the crystalline form is, or is comprised of, crystalline Form I.

36A. The formulation of embodiment 27A, 28A or 29A wherein the crystalline form is, or is comprised of crystalline Form III.

37A. The formulation of embodiment 27A, 28A or 29A wherein the crystalline form is or is comprised of Form IV.

38A. The formulation of embodiment 26A wherein the solid state form is amorphous 17α-ethynyl-androst-5-ene-3β,7β,17β-triol.

39A. The formulation of embodiment 38A wherein amorphous 17α-ethynyl-androst-5-ene-3β,7β,17β-triol is substantially free of crystalline 17α-ethynyl-androst-5-ene-3β,7β,17β-triol.

40A. The formulation of any one of embodiments 26A-33A, 38A, 39A wherein the formulation is a solid formulation.

41A. The formulation of any one of embodiments 26A-33A, 38A, 39A wherein the formulation is a liquid formulation prepared from a solid state form of 17α-ethynyl-androst-5-ene-3β,7β,17β-triol.

42A. The formulation of embodiment 40A wherein the formulation comprises 17α-ethynyl-androst-5-ene-3β,7β,17β-triol in crystalline form substantially free of 17α-ethynyl-androst-5-ene-3β,7β,17β-triol in amorphous form.

43A. The formulation of embodiment 40A wherein the formulation comprises amorphous 17α-ethynyl-androst-5-ene-3β,7β,17β-triol substantially free of 17α-ethynyl-androst-5-ene-3β,7β,17β-triol in crystalline form.

44A. The formulation of embodiment 41A wherein the formulation is prepared from 17α-ethynyl-androst-5-ene-3β,7β,17β-triol in crystalline form substantially free of 17α-ethynyl-androst-5-ene-3β,7β,17β-triol in amorphous form.

45A. The formulation of embodiment 41A wherein the formulation is prepared from amorphous 17α-ethynyl-androst-5-ene-3β,7β,17β-triol substantially free of 17α-ethynyl-androst-5-ene-3β,7β,17β-triol in crystalline form.

46A. The formulation of embodiment 40A wherein the solid formulation is for oral dosing.

47A. The formulation of embodiment 46A wherein said at least one pharmaceutically acceptable excipient is a surface active agent in an amount sufficient to provide 90% dissolution of the formulation in water at ambient temperature after 30 min.

48A. The formulation of embodiment 47A wherein the surface active agent is sodium lauryl sulfate.

49A. The formulation of embodiment 46A wherein the pharmaceutically acceptable excipients are comprised of sodium lauryl sulfate, microcrystalline cellulose and magnesium stearate.

50A. The formulation of any one of embodiments 46A wherein the pharmaceutically acceptable excipients consist essentially of sodium lauryl sulfate, microcrystalline cellulose and magnesium stearate in relative amounts to the solid state form of 17α-ethynyl-androst-5-ene-3β,7β,17β-triol as provided by Table 14 or Table 15.

51A. An oral dosage form comprising a formulation of any one of embodiments 26A-33A, 38A, 39A or a solid state form of 17α-ethynyl-androst-5-ene-3β,7β,17β-triol.

52A. The oral dosage form of embodiment 51 wherein the dosage form is a tablet or capsule.

53A. A method to treat a hyperglycemic condition comprising administering to a subject in need thereof an effective amount of 17α-ethynyl-androst-5-ene-3β,7β,17β-triol in a solid state form or in a solid formulation comprising the solid state form of 17α-ethynyl-androst-5-ene-3β,7β,17β-triol and at least one pharmaceutically acceptable excipient.

54A. The method of embodiment 53A wherein the solid state form is a crystalline form of 17α-ethynyl-androst-5-ene-3β,7β,17β-triol substantially free of 17α-ethynyl-androst-5-ene-3β,7β,17β-triol in amorphous form.

55A. The method of embodiment 53A wherein the solid state form is a polymorph or pseudopolymorph form of 17α-ethynyl-androst-5-ene-3β,7β,17β-triol essentially free or substantially free of amorphous 17α-ethynyl-androst-5-ene-3β,7β,17β-triol and other crystalline forms of 17α-ethynyl-androst-5-ene-3β,7β,17β-triol.

56A. The method of embodiment 55A wherein the polymorph form is crystalline Form I.

57A. The method of any one of embodiments 53A-56A wherein the hyperglycemic condition is type 2 diabetes or metabolic syndrome.

58A. A method of preparing a solid formulation comprising the step of blending a solid state form of 17α-ethynyl-androst-5-ene-3β,7β,17β-triol with one, two, three or four other pharmaceutically acceptable excipients.

59A. The method of embodiment 58A wherein the solid state form is crystalline Form I.

60A. The method of embodiment 58A wherein the solid state form is amorphous 17α-ethynyl-androst-5-ene-3β,7β,17β-triol.

61A. The method of embodiment 58A wherein one excipient is sodium lauryl sulfate.

62A. A method of preparing a liquid formulation comprising 17α-ethynyl-androst-5-ene-3β,7β,17β-triol and a pharmaceutically acceptable excipients wherein at least one excipient is a liquid excipient comprising the step of contacting or admixing a solid state form of 17α-ethynyl-androst-5-ene-3β,7β,17β-triol with the liquid excipient, optionally in the presence of another excipient.

63A. The method of embodiment 62A wherein the solid state form is crystalline Form I.

64A. The method of embodiment 62A wherein the solid state form is amorphous 17α-ethynyl-androst-5-ene-3β,7β,17β-triol.

65A. A method to treat a hyperglycemic condition comprising administering to a subject in need thereof an effective amount of 17α-ethynyl-androst-5-ene-3β,7β,17β-triol in a liquid formulation prepared according to the method of embodiment 62A.

66A. The method of embodiment 65A wherein the hyperglycemic condition is Type 2 diabetes or metabolic syndrome.

67A. A product, wherein the product is a solid state form of 17α-ethynyl-androst-5-ene-3β,7β,17β-triol, prepared by the process according essentially to Example 1.

68A. A product, wherein the product is a solid state form of 17α-ethynyl-androst-5-ene-3β,7β,17β-triol, prepared by a process comprising the steps of (a) slurrying 17α-ethynyl-androst-5-ene-3β,7β,17β-triol in 75:25 by volume methanol:water; (b) drying solids obtained from step (a) under vacuum (about 28 in Hg) at about 45° C. to a loss on drying of about 0.5%.

69A. A product, wherein the product is a solid state form of 17α-ethynyl-androst-5-ene-3β,7β,17β-triol, prepared by a process comprising the steps adding water sufficient to maintain volume of a mixture of 17α-ethynyl-androst-5-ene-3β,7β,17β-triol in 10:1 by weight methanol:water during distillation of the mixture at ambient pressure to decrease by about 50% the initial volume contributed by methanol wherein 17α-ethynyl-androst-5-ene-3β,7β,17β-triol is present in between about 4-5% by weight relative to the total initial volume.

70A. The product of embodiment 69A wherein the process further comprises the step of cooling the solution to a final temperature between about 0-5° C. and holding at the final temperature for about 1 h.

71A. A product prepared by a process comprising the step of reducing in volume by 50% a solution of 17α-ethynyl-androst-5-ene-3β,7β,17β-triol in tetrahydrofuran:methanol in volume ratio of between about 5:1 to 10:1 wherein 17α-ethynyl-androst-5-ene-3β,7β,17β-triol is present in weight to volume percent of between about 5-10% in relation to the initial solution volume.

72A. The product of embodiment 71A wherein the volume ratio of tetrahydrofuran to water is about 6.5:1 and the weight to volume percent of 17α-ethynyl-androst-5-ene-3β,7β,17β-triol to initial solvent volume is about 7.5%

Further aspects of the invention related to crystalline 17α-ethynyl-androst-5-ene-3β,7β,17β-triol includes the following numbered embodiments.

1B. A crystalline form 17α-ethynyl-androst-5-ene-3β,7β,17β-triol.

2B. The crystalline form of embodiment 1B wherein the crystalline form is a pseudopolymorph, a polymorph or a mixture thereof.

3B. The crystalline form of embodiment 2B wherein the pseudopolymorph is a solvate.

4B. The crystalline form of embodiment 2B wherein the crystalline form is a pseudopolymorph wherein the pseudopolymorph consists essentially of 17α-ethynyl-androst-5-ene-3β,7β,17β-triol and an alcohol, water of hydration or a mixture thereof.

5B. The crystalline form of embodiment 4B wherein the alcohol is ethanol or methanol.

6B. The crystalline form of embodiment 4B wherein the pseudopolymorph is a single pseudopolymorph characterized by the molecular formula of $C_{21}H_{30}O_3 \cdot 1$ $CH_3OH$, $C_{21}H_{30}O_3 \cdot 0.5$ $CH_3OH \cdot 0.5$ $H_2O$, $C_{21}H_{30}O_3 \cdot 1$ $H_2O$ or $C_{21}H_{30}O_3 \cdot 2$ $H_2O$.

7B. The crystalline form of embodiment 3B wherein the solvate is a hydrate.

8B. The crystalline form of embodiment 7B wherein the hydrate is the dihydrate having the molecular formula of $C_{21}H_{30}O_3 \cdot 2$ $H_2O$.

9B. The crystalline form of embodiment 3B, 7B or 8B wherein the pseudopolymorph is essentially free of 17α-ethynyl-androst-5-ene-3β,7β,17β-triol in other crystalline forms and has a thermal gravimetric analysis thermogram with weight loss between about 9 to 10% from about 20° C. to about 110° C. obtained using a temperature ramp of 10° C./min.

10B. The crystalline form of embodiment 3B, 7B or 8B wherein the pseudopolymorph is a single polymorph essentially free of 17α-ethynyl-androst-5-ene-3β,7β,17β-triol in other crystalline forms and has a thermal gravimetric analysis thermogram with weight loss of between about 9.0% to about 9.7% from about 20° C. to about 110° C. obtained using a temperature ramp of 10° C./min.

11B. The crystalline form of embodiment 3B wherein the single pseudopolymorph is a solvate comprising methanol or ethanol.

12B. The crystalline form of embodiment 3B wherein the pseudopolymorph is a solvate comprising water of hydration.

13B. The crystalline form of embodiment 4B wherein the pseudopolymorph is a single pseudopolymorph essentially free of 17α-ethynyl-androst-5-ene-3β,7β,17β-triol in other crystalline forms and has a thermal gravimetric analysis thermogram essential identical to that provided in FIG. 12.

14B. The crystalline form of embodiment 13B wherein the single pseudopolymorph is crystalline Form III.

15B. The crystalline form of embodiment 4B wherein the pseudopolymorph is a single pseudopolymorph essentially free of 17α-ethynyl-androst-5-ene-3β,7β,17β-triol in other crystalline forms and has a thermal gravimetric analysis thermogram essential identical to that provided in FIG. 15.

16B. The crystalline form of embodiment 15B wherein the single pseudopolymorph is crystalline Form IV.

17B. The crystalline form of embodiment 1B wherein the crystalline form is an anhydrate.

18B. The crystalline form of embodiment 17B wherein the anhydrate is a product prepared from a process comprising the step of complete desolvation of crystalline Form III, Form IV or a mixture thereof.

19B. The crystalline form of embodiment 17B wherein the anhydrate is, or is comprised of, crystalline Form I.

20B. The crystalline form of embodiment 17B wherein the anhydrate is, or is comprised of, crystalline Form II.

21B. The crystalline form of embodiment 1B wherein the crystalline form is characterized by one or more, typically 2, 3 or 4 XRPD prominent peaks in Table 1A, Table 1B or Table 4; optionally with a prominent endotherm at about 266° C. obtained by differential scanning calorimetry using a temperature ramp of 10° C./min or negligible weight loss when heated from about 20° C. to about 100° C. as determined by thermogravimetric analysis (TGA) using a temperature ramp of 10° C./min.

22B. The crystalline form of embodiment 1B wherein the crystalline form is characterized by one or more, typically 2, 3 or 4 XRPD prominent peaks in Table 1A, Table 1B or Table 4; optionally with an apparent melting point of about 256° C. as determined in an open capillary tube.

23B. The crystalline form of embodiment 1B wherein the crystalline form is characterized by one or more, typically 2, 3 or 4 XRPD prominent peaks in Table 6; optionally with a prominent endotherm at about 259° C. obtained by differential scanning calorimetry thermogram using a temperature ramp of 10° C./min.

24B. The crystalline form of embodiment 1B wherein the crystalline form is characterized by one or more, typically 2, 3 or 4 XRPD prominent peaks in Table 9; optionally with a prominent endotherm at about 266° C. or a broad endotherm centered at about 105° C. obtained by differential scanning calorimetry thermogram using a temperature ramp of 10° C./min or about 9.5% weight loss when heated from about 20° C. to about 100° C. as determined by thermogravimetric analysis (TGA) using a temperature ramp of 10° C./min.

25B. The crystalline form of embodiment 1B wherein the crystalline form is characterized by one or more, typically 2, 3 or 4 XRPD prominent peaks in Table 11; optionally with a prominent endotherm at about 266° C. obtained by differential scanning calorimetry thermogram using a temperature ramp of 10° C./min or about 9.0% or about 9.7% loss when heated from about 30° C. to 100° C. as determined by thermogravimetric analysis (TGA) using a temperature ramp of 10° C./min.

26B. The crystalline form of embodiment 1B wherein the crystalline form is characterized by a pairwise distribution function calculated from a XRPD pattern from FIG. 2.

27B. The crystalline form of embodiment 1B wherein the crystalline form is characterized by one or more prominent absorptions, typically one, two or three prominent absorptions, in the Raman spectrum of FIG. 5B.

28B. The crystalline form of embodiment 1B wherein the crystalline form is characterized by one or more prominent absorptions, typically one, two or three absorptions, in the Raman spectrum of FIG. 13B.

Further aspects of the invention related to crystalline 17α-ethynyl-androst-5-ene-3β,7β,17β-triol includes the following numbered embodiments.

1C. Crystalline 17α-ethynyl-androst-5-ene-3β,7β,17β-triol.

2C. The crystalline 17α-ethynyl-androst-5-ene-3β,7β,17β-triol of embodiment 1C wherein the crystalline 17α-ethynyl-androst-5-ene-3β,7β,17β-triol is substantially free of amorphous 17α-ethynyl-androst-5-ene-3β,7β,17β-triol, optionally as characterized an analytical method described herein such as XRPD, DSC, TGA, TGA-IR analysis, melting point, Raman spectroscopy, Karl Fisher and/or elemental analysis. Crystalline forms of 17α-ethynyl-androst-5-ene-3β,7β,17β-triol includes anhydrates, hydrates and solvates, which include mixed water-solvent solvates. In these embodiments, 17α-ethynyl-androst-5-ene-3β,7β,17β-triol that is substantially free of amorphous 17α-ethynyl-androst-5-ene-3β,7β,17β-triol will typically and preferably contain less than about 10% w/w or less than about 7% w/w of the amorphous material.

3C. The crystalline 17α-ethynyl-androst-5-ene-3β,7β,17β-triol of embodiment 2C as Form III crystals. This form of 17α-ethynyl-androst-5-ene-3β,7β,17β-triol is a solvate material comprising water of hydration and is typically substantially free of amorphous 17α-ethynyl-androst-5-ene-3β,7β,17β-triol.

4C. The crystalline Form III 17α-ethynyl-androst-5-ene-3β,7β,17β-triol of embodiment 3C that contains less than about 10% w/w or less than about 7% w/w of other crystalline forms of 17α-ethynyl-androst-5-ene-3β,7β,17β-triol, optionally as characterized by an analytical method described herein such as XRPD, DSC, TGA, TG-IR analysis, melting point or Raman spectroscopy.

5C. The crystalline Form III 17α-ethynyl-androst-5-ene-3β,7β,17β-triol of embodiment 4C having (1) an XRPD pattern with prominent peaks of 15.64±0.1 and 16.60±0.1 degrees 2θ and with optional prominent peaks of 15.25±0.1 and 27.82±0.1 degrees 2θ; optionally with (2) a DTA or DSC thermogram having a sharp endotherm with onset at about 258° C. and a broad endotherm centered at about 105° C. and (3) TGA thermogram with about 9.6% weight loss from about 19° C. to about 100° C. using a temperature ramp of 10° C./min.

6C. The crystalline Form III 17α-ethynyl-androst-5-ene-3β,7β,17β-triol of embodiment 4C or 5C having a Raman spectrum with one, two or three prominent peaks of FIG. 13B or substantially identical to that shown in FIG. 13B.

7C. The crystalline 17α-ethynyl-androst-5-ene-3β,7β,17β-triol of embodiment 2C as Form IV crystals. This form of 17α-ethynyl-androst-5-ene-3β,7β,17β-triol is a solvate comprising methanol and is typically substantially free of amorphous 17α-ethynyl-androst-5-ene-3β,7β,17β-triol.

8C. The crystalline Form IV 17α-ethynyl-androst-5-ene-3β,7β,17β-triol of embodiment 7C that contains less than about 10% w/w or less than about 7% w/w of other crystalline forms of 17α-ethynyl-androst-5-ene-3β,7β,17β-triol, optionally as characterized by an analytical method described herein such as XRPD, DSC, TGA, TGA-IR, melting point or Raman spectroscopy.

9C. The crystalline Form IV 17α-ethynyl-androst-5-ene-3β,7β,17β-triol of embodiment 7C having (1) an XRPD pattern with prominent peaks at 15.66±0.1 and 16.62±0.1 degrees 2θ and with optional prominent peaks at 8.34±0.1 and 15.24±0.1 degrees 2θ; optionally with (2) a DTA or DSC thermogram having an sharp endotherm with onset between about 257° C. to 258° C. and a broad endotherm centered at about 98° C. and (3) TGA thermogram with about 9.7% loss from about 17° C. to about 110° C. using a temperature ramp of 10° C./min.

10C. The crystalline Form IV 17α-ethynyl-androst-5-ene-3β,7β,17β-triol of embodiment 7C having (1) an XRPD pattern with prominent peaks at 15.66±0.1 and 16.62±0.1 degrees 2θ and with optional prominent peaks at 8.34±0.1 and 15.24±0.1 degrees 2θ; optionally with (2) a DTA or DSC thermogram having an sharp endotherm with onset between about 257° C. to 258° C. and TGA thermogram with about 9% loss from about 30° C. to about 100° C. using a temperature ramp of 10° C./min.

11C. The crystalline Form IV 17α-ethynyl-androst-5-ene-3β,7β,17β-triol of embodiment 8C, 9C or 10C having a Raman trace with one, two or three prominent peaks of FIG. 19B or substantially identical to that shown in FIG. 19B.

12C. The crystalline 17α-ethynyl-androst-5-ene-3β,7β,17β-triol of embodiment 2C wherein the crystalline form is characterized by sufficient bioavailability of the crystalline material to be suitable for once daily or twice daily administration of unit oral doses of 5 mg, 10 mg, 15 mg, 20 mg or 50 mg to a human, such as a human having a hyperglycemic or autoimmune condition.

13C. The crystalline 17α-ethynyl-androst-5-ene-3β,7β,17β-triol of embodiment 12C wherein the crystalline form is characterized by sufficient stability on storage at 65° C. and 75% relative humidity for at least 6 months wherein sufficient stability is characterized by a change of less than about 5% w/w in the degradation of 17α-ethynyl-androst-5-ene-3β,7β,17β-triol to a degradant or by conversion of less than about 5% w/w to another solid state form.

14C. The crystalline 17α-ethynyl-androst-5-ene-3β,7β,17β-triol of embodiment 13C wherein the crystalline form is or is comprised of Form I.

15C. The crystalline 17α-ethynyl-androst-5-ene-3β,7β,17β-triol of embodiment 2C as Form I crystals. This form of 17α-ethynyl-androst-5-ene-3β,7β,17β-triol is an anhydrate and does not contain a solvent as measured by an analytical method described herein such as Karl Fisher titration and/or elemental analysis and/or TG-IR analysis and in preferred embodiments it is substantially free of amorphous 17α-ethynyl-androst-5-ene-3β,7β,17β-triol, optionally as measured by an analytical method described herein such as XRPD, DSC/DTA, TGA, Raman spectroscopy or solid state NMR spectroscopy 16C. The crystalline Form I 17α-ethynyl-androst-5-ene-3β,7β,17β-triol of embodiment 14C that contains less than about 10% w/w or less than about 7% w/w of other crystalline forms of 17α-ethynyl-androst-5-ene-3β,7β,17β-triol, optionally as characterized by an analytical method described herein such as XRPD, DSC/DTA, TGA, Raman spectroscopy or solid state NMR spectroscopy.

17C. The crystalline Form I 17α-ethynyl-androst-5-ene-3β,7β,17β-triol of embodiment 16C having an XRPD pattern with prominent peaks at 16.2±0.1, 16.7±0.1 and 17.8±0.1 degrees 2-theta and optional prominent peaks at 10.4±0.1, 12.6±0.1, 15.1±0.1 degrees 2-theta; optionally with (2) a DTA or DSC thermogram having an endotherm with onset at about 258° C. and TGA thermogram with negligible wt % loss in a temperature range of about 30° C. to about 100° C. using a temperature ramp of 10° C./min.

18C. The crystalline Form I 17α-ethynyl-androst-5-ene-3β,7β,17β-triol of embodiment 17C wherein the crystals have the morphology of tablets or needles.

19C. The crystalline Form I 17α-ethynyl-androst-5-ene-3β,7β,17β-triol of embodiment 16C or 17C having a Raman trace with one, two or three prominent peaks of FIG. 5 or substantially identical to that shown in FIG. 5B.

20C. The crystalline 17α-ethynyl-androst-5-ene-3β,7β,17β-triol of embodiment 12C wherein the crystalline form is, or is comprised of, Form II.

21C. The crystalline 17α-ethynyl-androst-5-ene-3β,7β,17β-triol of embodiment 2C as Form II crystals. This form of 17α-ethynyl-androst-5-ene-3β,7β,17β-triol is an anhydrate as determined by an analytical method described herein such as Karl Fisher titration and/or elemental analysis and/or TGA and in preferred embodiments it is substantially free of amorphous 17α-ethynyl-androst-5-ene-3β,7β,17β-triol, optionally as measured by an analytical method described herein such as XRPD, DSC/DTA, TGA, Raman spectroscopy or solid state NMR spectroscopy 22C. The crystalline Form II 17α-ethynyl-androst-5-ene-3β,7β,17β-triol of embodiment 21C that contains less than about 10% w/w or less than about 7% w/w of other crystalline forms of 17α-ethynyl-androst-5-ene-3β,7β,17β-triol, optionally as characterized by an analytical method described herein such as XRPD, DSC/DTA, TGA, Raman spectroscopy or solid state NMR spectroscopy.

23C. The crystalline Form II 17α-ethynyl-androst-5-ene-3β,7β,17β-triol of embodiment 21C having an XRPD pattern with prominent peaks at 2.5±0.1, 5.0±0.1 and 16.2±0.1 degree 2-theta; optionally with prominent peaks at 7.6±0.1, 10.4±0.1, 17.8±0.1 degree 2-theta and (2) a DTA or DSC thermogram having an sharp endotherm at 266° C. and TGA thermogram with negligible wt % loss in a temperature range of about 30° C. to about 100° C. using a temperature ramp of 10° C./min.

24C. Use of crystalline 17α-ethynyl-androst-5-ene-3β,7β,17β-triol, or use of a composition comprising one or more excipients and crystalline 17α-ethynyl-androst-5-ene-3β,7β,17β-triol, for the preparation of a medicament for the treatment or prophylaxis of a hyperglycemic or autoimmune condition. In these embodiments, the use of crystalline Forms I or Form III 17α-ethynyl-androst-5-ene-3β,7β,17β-triol is preferred, with Form I most preferred. In these uses appreciable amounts of two crystal forms can be present, but there is preferably only 1 crystalline form present, e.g., a single crystal form comprises at least about 90% w/w or at least about 93% w/w of the 17α-ethynyl-androst-5-ene-3β,7β,17β-triol that is present.

25C. The use according to embodiment 24C wherein the autoimmune condition is type 1 diabetes, rheumatoid arthritis, ulcerative colitis or Hashimotos' thyroiditis and the hyperglycemic condition is type 2 diabetes or metabolic syndrome 26C. The use according to embodiment 25C wherein the crystalline 17α-ethynyl-androst-5-ene-3β,7β,17β-triol is substantially free of amorphous 17α-ethynyl-androst-5-ene-3β,7β,17β-triol, optionally as characterized by an analytical method described herein such as XRPD, DSC/DTA, TGA, TGA-IR, Raman spectroscopy and/or solid state NMR.

27C. A method to make crystalline 17α-ethynylandrost-5-ene-3β,7β,17β-triol comprising the step of (i) reducing in volume a solution of 17α-ethynylandrost-5-ene-3β,7β,17β-triol in methanol-water, methanol-tetrahydrofuran or acetone, optionally under vacuum and/or with heating at about 35° C. to about 70° C., or (ii) removing methanol from a solution of 17α-ethynylandrost-5-ene-3β,7β,17β-triol in methanol-water by distillation concomitant with addition of water wherein the initial volume of the solution is substantially maintained, or (iii) removing ethanol from a solution of 17α-ethynylandrost-5-ene-3β,7β,17β-triol in ethanol by evaporation, optionally under vacuum and/or with heating at about 35° C. to about 80° C., or (iv) slurrying or mixing 17α-ethynylandrost-5-ene-3β,7β,17β-triol in isopropanol or in methyl ethyl ketone, or (v) precipitating with water a solution of 17α-ethynylandrost-5-ene-3β,7β,17β-triol in ethanol, optionally at a temperature of about 0° C. to about 35° C., or (vi) reducing the volume of a solution of 17α-ethynylandrost-5-ene-3β,7β,17β-triol in methanol-chloroform, optionally under vacuum and/or with heating at about 35° C. to about 65° C.

Further aspects of the invention related to amorphous 17α-ethynyl-androst-5-ene-3β,7β,17β-triol include the following numbered embodiments.

1D. Amorphous 17α-ethynyl-androst-5-ene-3β,7β,17β-triol.

2D. The amorphous 17α-ethynyl-androst-5-ene-3β,7β,17β-triol of embodiment 1D wherein the amorphous 17α-ethynyl-androst-5-ene-3β,7β,17β-triol is substantially free of crystalline 17α-ethynyl-androst-5-ene-3β,7β,17β-triol as measured by XRPD analysis, optionally wherein the amorphous 17α-ethynyl-androst-5-ene-3β,7β,17β-triol is substantially free of crystalline Form I and/or Form II 17α-ethynyl-androst-5-ene-3β,7β,17β-triol.

3D. The amorphous 17α-ethynyl-androst-5-ene-3β,7β,17β-triol of embodiment 1D wherein the amorphous 17α-ethynyl-androst-5-ene-3β,7β,17β-triol is substantially free of crystalline 17α-ethynyl-androst-5-ene-3β,7β,17β-triol as measured by XRPD analysis, optionally wherein the amorphous 17α-ethynyl-androst-5-ene-3β,7β,17β-triol is substantially free of crystalline Form I.

4D. The amorphous 17α-ethynyl-androst-5-ene-3β,7β,17β-triol of embodiment 1D wherein the amorphous 17α-ethynyl-androst-5-ene-3β,7β,17β-triol is substantially free of crystalline 17α-ethynyl-androst-5-ene-3β,7β,17β-triol as measured by XRPD analysis, optionally wherein the amorphous 17α-ethynyl-androst-5-ene-3β,7β,17β-triol is substantially free of crystalline Form I and Form II.

4D. The amorphous 17α-ethynyl-androst-5-ene-3β,7β,17β-triol of embodiment 1D wherein the amorphous 17α-ethynyl-androst-5-ene-3β,7β,17β-triol contains less than about 8% w/w of crystalline 17α-ethynyl-androst-5-ene-3β,7β,17β-triol.

5D. The amorphous 17α-ethynyl-androst-5-ene-3β,7β,17β-triol of embodiment 1D wherein the amorphous 17α-ethynyl-androst-5-ene-3β,7β,17β-triol contains less than about 5% w/w of crystalline 17α-ethynyl-androst-5-ene-3β,7β,17β-triol.

5D. A pharmaceutical formulation comprising one or more excipients and amorphous 17α-ethynyl-androst-5-ene-3β,7β,17β-triol, optionally wherein the amorphous 17α-ethynyl-androst-5-ene-3β,7β,17β-triol is as described in any one of embodiments 1D-4D.

6D. A product, wherein the product is amorphous 17α-ethynyl-androst-5-ene-3β,7β,17β-triol, produced by a process comprising the step of lyophilization of a mixture of 17α-ethynyl-androst-5-ene-3β,7β,17β-triol and t-butanol.

7D. The product of embodiment 6D wherein the amorphous 17α-ethynyl-androst-5-ene-3β,7β,17β-triol I (1) is substantially free of crystalline 17α-ethynyl-androst-5-ene-3β,7β,17β-triol as measured by XRPD analysis, or (2) contains less than about 8% w/w of crystalline 17α-ethynyl-androst-5-ene-3β,7β,17β-triol, or (3) contains less than about 5% w/w of crystalline 17α-ethynyl-androst-5-ene-3β,7β,17β-triol, optionally wherein the crystalline 17α-ethynyl-androst-5-ene-3β,7β,17β-triol is Form I 17α-ethynyl-androst-5-ene-3β,7β,17β-triol.

8D. Use of amorphous 17α-ethynyl-androst-5-ene-3β,7β,17β-triol, or use of a composition comprising one or more excipients and amorphous 17α-ethynyl-androst-5-ene-3β,7β,17β-triol for the preparation of a medicament for the treatment or prophylaxis of a hyperglycemic or autoimmune condition.

9D. The use according to embodiment 8D wherein the autoimmune condition is type 1 diabetes, rheumatoid arthritis, ulcerative colitis or Hashimotos' thyroiditis and the hyperglycemic condition is type 2 diabetes or metabolic syndrome. In these uses, amorphous material preferably comprises at least about 90% w/w or at least about 95% w/w of the 17α-ethynyl-androst-5-ene-3β,7β,17β-triol that is present.

10D. The use according to embodiment 9D wherein the amorphous 17α-ethynyl-androst-5-ene-3β,7β,17β-triol is substantially free of crystalline 17α-ethynyl-androst-5-ene-3β,7β,17β-triol as measured by XRPD analysis or wherein the amorphous 17α-ethynyl-androst-5-ene-3β,7β,17β-triol contains less than about 8% w/w or less than about 5% w/w of crystalline 17α-ethynyl-androst-5-ene-3β,7β,17β-triol.

1E. Crystalline 17α-ethynyl-androst-5-ene-3β,7β,17β-triol.

2E. The crystalline 17α-ethynyl-androst-5-ene-3β,7β,17β-triol of embodiment 1E wherein the crystalline 17α- ethynyl-androst-5-ene-3β,7β,17β-triol is substantially free of amorphous 17α-ethynyl-androst-5-ene-3β,7β,17β-triol.

3E. The crystalline 17α-ethynyl-androst-5-ene-3β,7β,17β-triol of embodiment 2E wherein the crystalline form of 17α-ethynyl-androst-5-ene-3β,7β,17β-triol is an anhydrate or is characterized by a negligible weight loss or a weight loss of about 0.5% or less when heated between about 40° C. to about 105° C. using a temperature ramp of 10° C./min.

4E. The crystalline anhydrate of embodiment 3E wherein the anhydrate is Form I or Form II 17α-ethynyl-androst-5-ene-3β,7β,17β-triol or a mixture thereof.

5E. The crystalline anhydrate of embodiment 4E wherein the anhydrate is Form I 17α-ethynyl-androst-5-ene-3β,7β,17β-triol substantially free of Form II 17α-ethynyl-androst-5-ene-3β,7β,17β-triol.

6E. The crystalline anhydrate of embodiment 5E wherein Form I 17α-ethynyl-androst-5-ene-3β,7β,17β-triol is characterized by or has an X-ray powder diffraction pattern with peak positions of 10.38±0.1, 16.20±0.1 and 17.75±0.1 degrees 2-theta, optionally with one, two or three peak positions selected from the group consisting of 12.66±0.1, 15.10±0.1, 16.73±0.1, 28.92±0.1 degrees 2-theta.

7E. The crystalline anhydrate of embodiment 6E wherein the Form I 17α-ethynyl-androst-5-ene-3β,7β,17β-triol is further characterized by or has a differential scanning calorimetry thermogram with a prominent endotherm at about 266° C. obtained using a temperature ramp of 10° C./min.

8E. The crystalline anhydrate of embodiment 5E wherein Form I 17α-ethynyl-androst-5-ene-3β,7β,17β-triol is substantially free of Form II, Form III and Form IV 17α-ethynyl-androst-5-ene-3β,7β,17β-triol or wherein Form I 17α-ethynyl-androst-5-ene-3β,7β,17β-triol comprises at least about 90% w/w of all crystalline 17α-ethynyl-androst-5-ene-3β,7β,17β-triol that is present.

9E. The crystalline anhydrate of any one of embodiments 5E-8E wherein Form I 17α-ethynyl-androst-5-ene-3β,7β,17β-triol has a Raman spectroscopy spectrum with peak positions at about 2105 and 1673 cm-1, optionally with one, two or three peak positions selected from the group consisting of about 2887, 1467, 1437, 833, 712, 681, 484, 470, 457, 247 and 226 cm$^{-1}$ or substantially identical to that of FIG. 5A or FIG. 5B.

10E. The crystalline anhydrate of embodiment 6E wherein the Form I 17α-ethynyl-androst-5-ene-3β,7β,17β-triol is characterized by or has a single crystal X-ray crystallography space group of P2$_1$2$_1$2$_1$ (#19).

11E. The crystalline anhydrate of embodiment 8E wherein the Form I 17α-ethynyl-androst-5-ene-3β,7β,17β-triol is characterized by morphology of FIG. 6A or FIG. 6B.

12E. The crystalline anhydrate of embodiment 8E wherein the Form I 17α-ethynyl-androst-5-ene-3β,7β,17β-triol is characterized by morphology of blades or plates.

13E. The crystalline anhydrate of embodiment 4E wherein the crystalline 17α-ethynyl-androst-5-ene-3β,7β,17β-triol is a mixture of Form II and Form I 17α-ethynyl-androst-5-ene-3β,7β,17β-triol substantially free of Form III and Form IV 17α-ethynyl-androst-5-ene-3β,7β,17β-triol.

14E. The crystalline anhydrate of embodiment 4E wherein the crystalline 17α-ethynyl-androst-5-ene-3β,7β,17β-triol is Form II 17α-ethynyl-androst-5-ene-3β,7β,17β-triol substantially free of Form I 17α-ethynyl-androst-5-ene-3β,7β,17β-triol.

15E. The crystalline anhydrate of embodiment 14E wherein Form II 17α-ethynyl-androst-5-ene-3β,7β,17β-triol is characterized by or has an X-ray powder diffraction pattern with peak positions of 2.49±0.1, 5.04±0.1 and 16.20±0.1 degrees 2-theta, optionally with one two or three peak positions selected from the group consisting of 10.44±0.1, 12.69±0.1, 15.12±0.1, 16.71±0.1, 17.73±0.1 and 28.92±0.1 degrees 2-theta.

16E. The crystalline anhydrate of embodiment 14E wherein Form II 17α-ethynyl-androst-5-ene-3β,7β,17β-triol is further characterized by or has a differential scanning calorimetry thermogram with a prominent endotherm at about 259° C., optionally with a week exotherm centered at about 207° C., obtained using a temperature ramp of 10° C./min.

17E. The crystalline anhydrate of embodiment 13E wherein Form II 17α-ethynyl-androst-5-ene-3β,7β,17β-triol is substantially free of Form I, Form III and Form IV 17α-ethynyl-androst-5-ene-3β,7β,17β-triol or wherein Form II 17α-ethynyl-androst-5-ene-3β,7β,17β-triol comprises at least about 90% w/w of all crystalline 17α-ethynyl-androst-5-ene-3β,7β,17β-triol that is present.

18E. The crystalline anhydrate of embodiment 14E wherein the Form II 17α-ethynyl-androst-5-ene-3β,7β,17β-triol is characterized by or has a single crystal X-ray crystallography space group of P2$_1$2$_1$2 (#18).

19E. The crystalline 17α-ethynyl-androst-5-ene-3β,7β,17β-triol of embodiment 2E wherein the crystalline form of 17α-ethynyl-androst-5-ene-3β,7β,17β-triol is a solvate or is characterized by a weight loss of BLANK when heated between about 40° C. to about 105° C. using a temperature ramp of 10° C./min.

20E. The crystalline solvate of embodiment 19E wherein the crystalline 17α-ethynyl-androst-5-ene-3β,7β,17β-triol is Form III or Form IV 17α-ethynyl-androst-5-ene-3β,7β,17β-triol or a mixture thereof.

21E. The crystalline solvate of embodiment 20E wherein the solvate is Form III 17α-ethynyl-androst-5-ene-3β,7β,17β-triol substantially free of Form I and Form II 17α-ethynyl-androst-5-ene-3β,7β,17β-triol.

22E. The crystalline solvate of embodiment 21E wherein Form III 17α-ethynyl-androst-5-ene-3β,7β,17β-triol is characterized by or has an X-ray powder diffraction pattern with peak positions of 15.24±0.1, 15.66±0.1 and 16.62±0.1, degrees 2-theta, optionally with one two or three peak positions selected from the group consisting of 8.37±0.1, 12.30±0.1 and 27.78±0.1 degrees 2-theta.

23E. The crystalline solvate of embodiment 20E wherein Form III 17α-ethynyl-androst-5-ene-3β,7β,17β-triol is further characterized by or has a differential scanning calorimetry thermogram with a prominent endotherm at about 266° C. or a broad endotherm centered at about 105° C. or 107° C. and optionally with a endotherm at about 1.7° C. or about 2.3° C. obtained using a temperature ramp of 10° C./min.

24E. The crystalline solvate of embodiment 19E wherein Form III 17α-ethynyl-androst-5-ene-3β,7β,17β-triol is substantially free of Form I, Form II or Form IV and Form V 17α-ethynyl-androst-5-ene-3β,7β,17β-triol or wherein Form III 17α-ethynyl-androst-5-ene-3β,7β,17β-triol comprises at least about 90% w/w of all crystalline 17α-ethynyl-androst-5-ene-3β,7β,17β-triol that is present.

25E. The crystalline anhydrate of any one of embodiments 21E-24E wherein Form III 17α-ethynyl-androst-5-ene-3β,7β,17β-triol is characterized by or has a Raman spectroscopy spectrum with peak positions at about 2108 and 1666 cm-1, optionally with one, two or three peak positions selected from the group consisting of about 2950, 1469, 1437, 711, 681, 251 and 224 cm-1 or substantially identical to that of FIG. 13A or FIG. 13B.

26E. The crystalline solvate of embodiment 19E wherein the solvate is Form IV 17α-ethynyl-androst-5-ene-3β,7β, 17β-triol substantially free of Form I and Form II 17α-ethynyl-androst-5-ene-3β,7β,17β-triol.

27E. The crystalline solvate of embodiment 26E wherein Form IV 17α-ethynyl-androst-5-ene-3β,7β,17β-triol is characterized by or has an X-ray powder diffraction pattern with peak positions of 15.24±0.1, 15.66±0.1 and 16.62±0.1 degrees 2-theta, optionally with one two or three peak positions selected from the group consisting of 8.34±0.1, 10.50±0.1, 12.30±0.1, 16.23±0.1 and 27.78±0.1 degrees 2-theta.

28E. The crystalline solvate of embodiment 27E wherein Form IV 17α-ethynyl-androst-5-ene-3β,7β,17β-triol is further characterized by or has a differential scanning calorimetry thermogram with a prominent endotherm at about 266° C. or a broad endotherm centered at about 98° C. and optionally with a sharp endotherm between about 75-90° C. obtained using a temperature ramp of 10° C./min.

29E. The crystalline solvate of embodiment 19E wherein Form IV 17α-ethynyl-androst-5-ene-3β,7β,17β-triol is substantially free of Form I, Form II and Form III 17α-ethynyl-androst-5-ene-3β,7β,17β-triol or wherein Form IV 17α-ethynyl-androst-5-ene-3β,7β,17β-triol comprises at least about 90% w/w of all crystalline 17α-ethynyl-androst-5-ene-3β,7β,17β-triol that is present.

30E. The crystalline solvate of any one of embodiments 19E-24E wherein Form IV 17α-ethynyl-androst-5-ene-3β,7β,17β-triol is characterized by or has a Raman spectroscopy spectrum with peak positions at about 2107 and 1666 cm-1, optionally with one, two or three peak positions selected from the group consisting of about 2950, 1469, 1437, 711, 467, 457 and 224 cm-1 or substantially identical to that of FIG. 13A or FIG. 13B.

31E. The crystalline solvate of embodiment 19E wherein the solvate comprises at least one $C_{1-6}$ alcohol, water or a combination thereof.

32E. The crystalline solvate of embodiment 31E wherein the solvate consists essentially of a $C_{1-6}$ alcohol or a $C_{1-6}$ alcohol and water of hydration.

33E. The crystalline solvate of embodiment 32E wherein the $C_{1-6}$ alcohol is ethanol or methanol.

34E. The crystalline solvate of embodiment 19E wherein the solvate consists essentially of water of hydration.

35E. The crystalline solvate of embodiment 28E wherein the crystalline 17α-ethynyl-androst-5-ene-3β,7β,17β-triol is Form IV or Form V 17α-ethynyl-androst-5-ene-3β,7β,17β-triol.

36E. The crystalline solvate of embodiment 31E wherein the crystalline 17α-ethynyl-androst-5-ene-3β,7β,17β-triol is Form III or Form IV, wherein the Form III or Form IV 17α-ethynyl-androst-5-ene-3β,7β,17β-triol is substantially free of crystalline Form I and Form II 17α-ethynyl-androst-5-ene-3β,7β,17β-triol.

37E. Amorphous 17α-ethynyl-androst-5-ene-3β,7β,17β-triol.

38E. The amorphous 17α-ethynyl-androst-5-ene-3β,7β,17β-triol of embodiment 37E wherein the amorphous 17α-ethynyl-androst-5-ene-3β,7β,17β-triol is substantially free of crystalline 17α-ethynyl-androst-5-ene-3β,7β,17β-triol or contains less than about 10% w/w of crystalline 17α-ethynyl-androst-5-ene-3β,7β,17β-triol.

Figure 17:
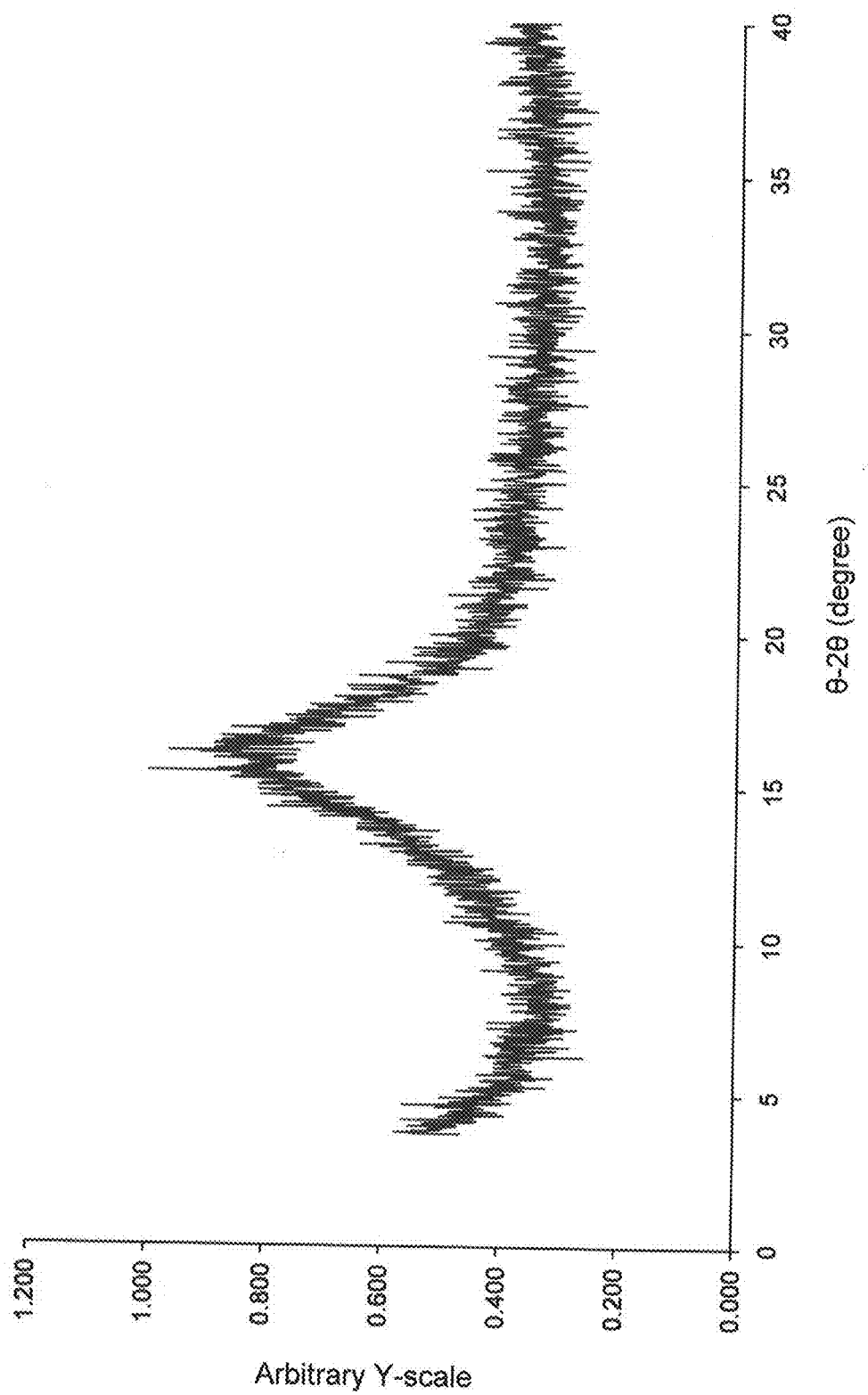
FIG. 17 is a low resolution XRPD pattern of a sample containing amorphous 17α-ethynyl-androst-5-ene-3β,7β,17β-triol essentially free of crystalline 17α-ethynyl-androst-5-ene-3β,7β,17β-triol.

39E. The amorphous 17α-ethynyl-androst-5-ene-3β,7β,17β-triol of embodiment 40E wherein the wherein the amorphous 17α-ethynyl-androst-5-ene-3β,7β,17β-triol is characterized by or has (1) an X-ray powder diffraction pattern with a broad band at about 16 degree 2 theta or X-ray powder diffraction pattern substantially as shown at FIG. 17; (2) a thermogravimetric analysis thermogram weight loss of between about 11-12% when heated from about 30° C. to about 110° C. or a weight loss of between about 15-17% when heated from about 30° C. to about 200° C., obtained using a temperature ramp of 10° C./min; (3) a modulated DSC thermal analysis thermogram that provide a glass transition temperature of about 44° C. obtained using a temperature ramp of 1° C./min or (4) a combination of the characteristics described at (1) and (2) or (1) and (3).

40E. A method to make crystalline anhydrate Form I 17α-ethynyl-androst-5-ene-3β,7β,17β-triol comprising the step of recovering 17α-ethynyl-androst-5-ene-3β,7β,17β-triol from a mixture of 17α-ethynyl-androst-5-ene-3β,7β,17β-triol, methanol and water.

41E. A method to make crystalline anhydrate Form II 17α-ethynyl-androst-5-ene-3β,7β,17β-triol comprising the step of recovering 17α-ethynyl-androst-5-ene-3β,7β,17β-triol from a mixture of 17α-ethynyl-androst-5-ene-3β,7β,17β-triol and methyl ethyl ketone or ethyl acetate.

42E. A method to make crystalline anhydrate Form III 17α-ethynyl-androst-5-ene-3β,7β,17β-triol comprising the step of recovering 17α-ethynyl-androst-5-ene-3β,7β,17β-triol from a mixture of 17α-ethynyl-androst-5-ene-3β,7β,17β-triol, methanol and chloroform.

43E. A method to make crystalline anhydrate Form IV 17α-ethynyl-androst-5-ene-3β,7β,17β-triol comprising the step of recovering 17α-ethynyl-androst-5-ene-3β,7β,17β-triol from a mixture of 17α-ethynyl-androst-5-ene-3β,7β,17β-triol, ethanol and water.

44E. A formulation comprising one or more excipients and crystalline 17α-ethynyl-androst-5-ene-3β,7β,17β-triol.

45E. The formulation of embodiment 44E wherein the formulation is a solid formulation, optionally tablets, capsules or another unit dosage form suitable for oral administration.

46E. A method of preparing a formulation comprising the step of contacting, mixing and/or blending amorphous or crystalline 17α-ethynyl-androst-5-ene-3β,7β,17β-triol or a mixture thereof with one, two, three, four or more excipients to obtain a mixture and processing the mixture to obtain a formulation, optionally wherein the formulation is a solid formulation or comprises unit dosages suitable for oral administration to humans, optionally tablets, caplets or capsules.

47E. The method of embodiment 46E wherein the crystalline 17α-ethynyl-androst-5-ene-3β,7β,17β-triol is a solvate.

48E. The method of embodiment 47E wherein the crystalline solvate comprises ethanol or methanol and water of hydration.

49E. The method of embodiment 47E wherein the crystalline solvate consists essentially of water of hydration.

50E. The method of embodiment 47E wherein the solvate is Form III or Form IV or a mixture thereof.

51E. The method of embodiment 46E wherein the crystalline 17α-ethynyl-androst-5-ene-3β,7β,17β-triol is an anhydrate.

52E. The method of embodiment 51E wherein the crystalline anhydrate is Form I 17α-ethynyl-androst-5-ene-3β,7β,17β-triol.

53E. The method of embodiment 46E wherein at least one excipient is a surface active agent, optionally sodium lauryl sulfate or Polysorbate-80

54E. The method of embodiment 46E wherein at least one excipient is a liquid vehicle, optionally wherein the formulation is a liquid formulation.

55E. The method of embodiment 54E wherein another excipient is a cyclodextrin.

56E. The method of embodiment 55E wherein the cyclodextrin is sulfobutylether-β-cyclodextrin or hydroxypropyl-β-cyclodextrin.

57E. A method to treat a inflammation condition in a subject comprising administering to the subject or delivering to the subject's tissues an effective amount of crystalline 17α-ethynyl-androst-5-ene-3β,7β,17β-triol, a formulation comprising crystalline 17α-ethynyl-androst-5-ene-3β,7β, 17β-triol and at least one or more excipients or a formulation prepared from crystalline 17α-ethynyl-androst-5-ene-3β,7β, 17β-triol and one, two, three, four or more excipients.

58E. The method of embodiment 57E wherein the crystalline 17α-ethynyl-androst-5-ene-3β,7β,17β-triol is Form I or Form III 17α-ethynyl-androst-5-ene-3β,7β,17β-triol essentially free of amorphous 17α-ethynyl-androst-5-ene-3β,7β,17β-triol.

59E. The method of embodiment 57E wherein the inflammation condition is a metabolic condition.

60E. The method of embodiment 59E wherein the metabolic condition is a hyperglycemic condition.

61E. The method of 60E wherein the metabolic condition is type 1 diabetes, type 2 diabetes or metabolic syndrome.

62E. The method of embodiment 57E wherein the inflammation condition is an autoimmune condition.

63E. The method of embodiment 62E wherein the autoimmune condition is multiple sclerosis, rheumatoid arthritis or ulcerative colitis.

64E. The method of embodiment 57E wherein the inflammation condition is a hyperproliferation condition.

65E. The method of embodiment 64E wherein the hyperproliferation condition is prostate cancer, breast cancer or benign prostatic hyperplasia.

66E. The method of embodiment 57E wherein the inflammation condition is a bowel inflammation condition.

67E. The method of embodiment 66E wherein the bowel inflammation condition is ulcerative colitis, Crohn's disease or inflammatory bowel syndrome.

68E. The method of embodiment 57E wherein the inflammation condition is a lung inflammation condition.

69E. The method of embodiment 68E wherein the lung inflammation condition is asthma, COPD or cystic fibrosis.

70E. The method of embodiment 57E wherein the inflammation condition is a neurodegenerative condition.

71E. The method of embodiment 70E wherein the neurodegenerative condition is Parkinson's disease, Alzheimer's disease or Amyotrophic Lateral Sclerosis.

72E. A method to treat a inflammation condition in a subject comprising administering to the subject or delivering to the subject's tissues an effective amount of amorphous 17α-ethynyl-androst-5-ene-3β,7β,17β-triol, a formulation comprising amorphous 17α-ethynyl-androst-5-ene-3β,7β, 17β-triol and at least one or more excipients or a formulation prepared from amorphous 17α-ethynyl-androst-5-ene-3β, 7β,17β-triol and one, two, three, four or more excipients.

73E. The method of embodiment 72E wherein the amorphous 17α-ethynyl-androst-5-ene-3β,7β,17β-triol is substantially free of crystalline 17α-ethynyl-androst-5-ene-3β, 7β,17β-triol.

74E. The method of embodiment 72E wherein the inflammation condition is a metabolic condition.

75E. The method of embodiment 74E wherein the metabolic condition is a hyperglycemic condition.

76E. The method of embodiment 75E wherein the metabolic condition is type 1 diabetes, type 2 diabetes or metabolic syndrome.

77E. The method of embodiment 72E wherein the inflammation condition is an autoimmune condition.

78E. The method of embodiment 77E wherein the autoimmune condition is Type 1 diabetes, multiple sclerosis, rheumatoid arthritis or ulcerative colitis.

79E. The method of embodiment 72E wherein the inflammation condition is a hyperproliferation condition.

80E. The method of embodiment 79E wherein the hyperproliferation condition is prostate cancer, breast cancer or benign prostatic hyperplasia.

81E. The method of embodiment 72E wherein the inflammation condition is a bowel inflammation condition.

82E. The method of embodiment 81E wherein the bowel inflammation condition is ulcerative colitis, Crohn's disease or inflammatory bowel syndrome.

83E. The method of embodiment 72E wherein the inflammation condition is a lung inflammation condition.

84E. The method of embodiment 83E wherein the lung inflammation condition is asthma, COPD or cystic fibrosis.

85E. The method of embodiment 72E wherein the inflammation condition is a neurodegenerative condition.

86E. The method of embodiment 85E wherein the neurodegenerative condition is Parkinson's disease, Alzheimer's disease or Amyotrophic Lateral Sclerosis.

87E. Use of crystalline or amorphous 17α-ethynyl-androst-5-ene-3β,7β,17β-triol, or use of a composition comprising one or more pharmaceutically acceptable excipients and crystalline or amorphous 17α-ethynyl-androst-5-ene-3β,7β,17β-triol, for the preparation of a medicament.

88E. Use of crystalline 17α-ethynyl-androst-5-ene-3β,7β, 17β-triol, or use of a composition comprising one or more excipients and crystalline 17α-ethynyl-androst-5-ene-3β,7β, 17β-triol, for the preparation of a medicament for the treatment or prophylaxis of an inflammation condition.

89E. A crystalline anhydrate of 17α-ethynyl-androst-5-ene-3β,7β,17β-triol wherein the crystalline anhydrate is characterized by or has an X-ray crystallography space group of $P2_12_12_1$ (#19).

90E. A crystalline anhydrate of 17α-ethynyl-androst-5-ene-3β,7β,17β-triol that is characterized by or has unit cell parameters in angstroms of a=11.740, b=12.273, c=12.339, α=90°, β=90°, γ=90°, Z'/Z=1/4 and unit cell volume of 1777.9 Å$^3$ determined from indexing the XRPD pattern in FIG. 1B.

91E. A crystalline anhydrate of 17α-ethynyl-androst-5-ene-3β,7β,17β-triol wherein the crystalline anhydrate is characterized by or has an X-ray crystallography space group of $P2_12_12$ (#18).

92E. A crystalline anhydrate of 17α-ethynyl-androst-5-ene-3β,7β,17β-triol wherein the crystalline anhydrate is characterized by or has unit cell parameters a=12.273, b=12.339, c=35.220, α=90°, β=90°, γ=90°, Z'/Z=3/12 and unit cell volume of 5333.6 Å$^3$ determined from indexing the XRPD pattern of FIG. 1B and symmetry reduction of the unit cell determined therefrom.

93E. A crystalline solvate 17α-ethynyl-androst-5-ene-3β, 7β,17β-triol wherein the crystalline solvate comprises at least one $C_{1-4}$ alcohol, water or a combination thereof.

94E. The crystalline solvate of embodiment 93E wherein the solvate is a hydrate.

95E. Amorphous 17α-ethynyl-androst-5-ene-3β,7β,17β-triol wherein the amorphous 17α-ethynyl-androst-5-ene-3β, 7β,17β-triol is characterized by an amorphous X-ray halo or an XRPD pattern substantially identical to the XRPD pattern of FIG. 18 optionally characterized by Raman absorptions at 2105 and 1673 cm$^{-1}$ and optionally with one, two or three absorptions selected from the group consisting of 2971, 2938, 2890 and 2859 cm$^{-1}$.

96E. A method to make crystalline 17α-ethynyl-androst-5-ene-3β,7β,17β-triol comprising the step of reducing in volume a solution of 17α-ethynyl-androst-5-ene-3β,7β,17β-triol in methanol-water, methanol-tetrahydrofuran or acetone or removing methanol from a solution of 17α-ethynyl-androst-5-ene-3β,7β,17β-triol in methanol-water by distillation concommitant with addition of water wherein the initial volume of the solution is substantially maintained or removing solvent from a solution of 17α-ethynyl-androst-5-ene-3β,7β,17β-triol in ethanol by evaporation or slurrying 17α-ethynyl-androst-5-ene-3β,7β,17β-triol in isopropanol.

97E. The method of embodiment 95E wherein the crystalline 17α-ethynyl-androst-5-ene-3β,7β,17β-triol is crystalline Form I needles.

98E. The method of embodiment 96E wherein the crystalline 17α-ethynyl-androst-5-ene-3β,7β,17β-triol is crystalline Form I tablets.

99E. The method of embodiment 96E wherein the crystalline 17α-ethynyl-androst-5-ene-3β,7β,17β-triol is crystalline Form I plates or blades.

100E. A method to make Form II 17α-ethynyl-androst-5-ene-3β,7β,17β-triol comprising the step of slurrying 17α-ethynyl-androst-5-ene-3β,7β,17β-triol in methyl ethyl ketone.

101E. A method to make Form III 17α-ethynyl-androst-5-ene-3β,7β,17β-triol comprising the step of precipitating with water a solution of 17α-ethynyl-androst-5-ene-3β,7β,17β-triol in ethanol.

102E. A method to make Form IV 17α-ethynyl-androst-5-ene-3β,7β,17β-triol comprising the step of reducing in volume a solution of 17α-ethynyl-androst-5-ene-3β,7β,17β-triol in methanol-chloroform.

103E. A method to make amorphous 17α-ethynyl-androst-5-ene-3β,7β,17β-triol comprising the step of removing solvent from a solution of 17α-ethynyl-androst-5-ene-3β,7β,17β-triol in t-butanol by lyophilization.

104E. A formulation comprising one or more excipients and crystalline 17α-ethynyl-androst-5-ene-3β,7β,17β-triol.

105E. The formulation of embodiment 104E wherein the formulation is a solid formulation, optionally tablets, capsules or another unit dosage form suitable for oral administration.

106E. A method of preparing a formulation comprising the step of contacting, mixing and/or blending amorphous or crystalline 17α-ethynyl-androst-5-ene-3β,7β,17β-triol with one, two, three, four or more excipients to obtain a mixture and processing the mixture to obtain a formulation, wherein the formulation is a solid formulation, a liquid formulation or comprises unit dosages suitable for oral administration to humans wherein the unit dosages are tablets, caplets or capsules.

107E. The method of embodiment 106E wherein the crystalline 17α-ethynyl-androst-5-ene-3β,7β,17β-triol is a solvate.

108E. The method of embodiment 107E wherein the crystalline solvate is a hydrate.

109E. The method of embodiment 106E wherein the crystalline 17α-ethynyl-androst-5-ene-3β,7β,17β-triol is an anhydrate.

110E. The method of embodiment 109E wherein the crystalline anhydrate is Form I 17α-ethynyl-androst-5-ene-3β,7β,17β-triol.

111E. The method of embodiment 106E wherein at least one of the excipients is a surface active agent.

112E. The method of embodiment 111E wherein said at least one excipient is a lauryl sulfate salt or Polysorbate-80 and wherein the crystalline 17α-ethynyl-androst-5-ene-3β, 7β,17β-triol is Form I 17α-ethynyl-androst-5-ene-3β,7β, 17β-triol.

113E. The method of embodiment 106E wherein one of the excipients is a liquid vehicle and wherein the formulation is a liquid formulation.

114E. The method of embodiment 113E wherein another excipient is a cyclodextrin

115E. The method of embodiment 114E wherein the cyclodextrin is sulfobutylether-β-cyclodextrin or hydroxypropyl-β-cyclodextrin.

116E. A method to treat an inflammation condition in a subject comprising administering to the subject or delivering to the subject's tissues an effective amount of crystalline 17α-ethynyl-androst-5-ene-3β,7β,17β-triol, a formulation comprising crystalline 17α-ethynyl-androst-5-ene-3β,7β, 17β-triol and at least one excipient or a formulation prepared from crystalline 17α-ethynyl-androst-5-ene-3β,7β,17β-triol and one, two, three, four or more excipients.

117E. The method of embodiment 116E wherein the crystalline 17α-ethynyl-androst-5-ene-3β,7β,17β-triol is Form I 17α-ethynyl-androst-5-ene-3β,7β,17β-triol.

118E. The method of embodiment 116E or 117E wherein the inflammation condition is a metabolic condition.

119E The method of embodiment 118E wherein the metabolic condition is type 2 diabetes.

120E. A method to treat a autoimmune condition in a subject comprising administering to the subject or delivering to the subject's tissues an effective amount of crystalline 17α-ethynyl-androst-5-ene-3β,7β,17β-triol, a formulation comprising crystalline 17α-ethynyl-androst-5-ene-3β,7β, 17β-triol and at least one excipient or a formulation prepared from crystalline 17α-ethynyl-androst-5-ene-3β,7β,17β-triol and one, two, three, four or more excipients.

121E. The method of embodiment 120E wherein the crystalline 17α-ethynyl-androst-5-ene-3β,7β,17β-triol is Form I 17α-ethynyl-androst-5-ene-3β,7β,17β-triol.

122E. The method of embodiment 120E or 121E wherein the autoimmune condition is rheumatoid arthritis or ulcerative colitis.

EXAMPLES

Example 1

Bulk Synthesis of 17α-ethynyl-androst-5-ene-3β,7β, 17β-triol

3β,7β-Bis-(trimethylsiloxy)-5-androsten-17-one: A mixture of 14.87 Kg of androst-5-en-17-one-3β,7β-diol, 23.8 Kg HMDS and 0.7 Kg saccharin catalyst in 100 acetonitrile was heated to reflux for 8 hours with stirring under a nitrogen atmosphere. Liberated ammonia was purged under slight vacuum. The reaction volume was then reduced by distillation to collect 30 of distillate (requires about 2 h). The reaction volume was further reduced to ½ of the original reaction volume by distillation under reduced pressure (700 mmHg), which requires about 2 h of heating at 50° C. The resulting uniform thick slurry is cooled to 5° C. (requires about 3 h), with additional acetonitrile added to maintain a minimum mixing volume, and held at that temperature for 1. The precipitated product was collected by filtration and dried at 45-50° C. under vacuum (29 mmHg) to a loss on drying (LOD) of not more than 1% (requires 20 h) to provide 16 Kg (81 yield) of the title compound (95% purity).

17α-Ethynyl-5-androstene-3β,7β,17β-triol: To 11.02 Kg TMS-acetylene in 56.5 L tetrahydrofuran (THF) at −27° C.

under a nitrogen atmosphere was added 8.51 L 10M n-BuLi. The n-butyl lithium was added very slowly to maintain a temperature at −7 to −27° C. (requires about 2 h) and the resulting reaction was stirred 10 min. at approximately 0° C. to produce TMS-lithium-acetylide. To the TMS-lithium-acetylide solution was added a solution of 25.41 Kg of 3β,7β-bis-(trimethylsiloxy)-5-androsten-17-one in 95.3 L THF filtered through a 25 μm filter while allowing the reaction temperature to rise to 20-25° C. After addition was completed, the reaction temperature was increased to 40-45° C. To quench the reactor contents, 31.8 L of methanol was added over a period of about 1 h followed by 3.81 Kg KOH in 18.4 L giving a final reactor temperature of 50° C. Liberated acetylene is purged under slight vacuum. The reactor contents were then concentrated by distillation at 80° C. for 1 h then under vacuum (175 mmHg) at about 70° C. (with an initial temperature of 25° C. to avoid bumping) to ½ of the original pot volume. The residue was cooled to about 10° C. and 35.0 Kg of deionized water was added, followed by 16.4 Kg 12 N HCl while maintaining a pot temperature of about 10° C. and giving a final pH of 1. Additional 26.0 kg deionized water was added and the resulting mixture was stirred at about 5° C. for 1 h. The resulting slurry was filtered and washed with 75:25 mixture of methanol:water (16.9 L methanol, 5.6 L water). The collected solids were dried under vacuum (28 in Hg) at 45° C. for 12 h for a loss on drying of no more than 0.5% to provide 9.6 Kg of the title compound (83% yield).

Example 2

Preparation of a Solid State Form Comprising Crystalline Form I 17α-ethynyl-androst-5-ene-3β,7β,17β-triol A slurry of 2.1 Kg 17α-ethynyl-androst-5-ene-3β,7β,17β-triol in 40.2 Kg methanol, prepared from Example 1, and 4.2 Kg water in a 250 L reactor was heated to reflux with stirring until all solids have dissolved. The reactor was cooled to 55-60° C. and the contents are pumped out into a receiving drum through a 25 micron filter. To the reactor was transferred 2.4 Kg of methanol which was then heated to 55-60° C. The methanol rinse is the transferred to the receiving drum as before. The contents of the receiving drum are then transferred back into the reactor which was fitted for vacuum distillation. The reactor contents were stirred and heated to reflux, maintaining a pot temperature of <=45° C., under vacuum until a volume of distillate is obtained that is equal to 1.1 to 1.5 times the volume of methanol that had been added to the reactor prior to distillation. Deionized water was added during the distillation to maintain the volume necessary for stirring (20-60 Kg of water may be used). A final solution volume in the reactor of 20-25 L was obtained. The solution is cooled to 0-5° C. and was maintained at that temperature for at least 1 h. The reactor slurry was then filtered through a Rosenmund filter dryer. The reactor is rinsed with 10 Kg deionized water. The water rinse is then used to wash the filtered product. The filter cake is dried under vacuum at 50° C. for at least 12 h whereupon a sample is tested for loss on drying. Drying was discontinued when the loss on drying was 0.5% drying to obtain 1.9 Kg of the titled material.

Crystalline Compound 1 (Form I 17α-ethynyl-androst-5-ene-3β,7β,17β-triol (Compound 1) obtained from this procedure is represented by the low resolution XRPD pattern (Pattern A) of FIG. 1. The peak listing for XRPD Pattern A is provided in Table 1A.

TABLE 1A

Peak Listing for XRPD Pattern of Crystalline Form I Low Resolution Pattern A

| °2θ | d space (Å) | Intensity (%) |
|---|---|---|
| 9.65 ± 0.1 | 9.158 | 1.1 |
| 10.41 ± 0.1 | 8.494 | 25.0 |
| 12.68 ± 0.1 | 6.978 | 7.4 |
| 14.32 ± 0.1 | 6.179 | 3.6 |
| 15.12 ± 0.1 | 5.857 | 33.4 |
| 16.20 ± 0.1 | 5.468 | 53.5 |
| 16.72 ± 0.1 | 5.299 | 16.0 |
| 17.85 ± 0.1 | 4.966 | 100 |
| 18.25 ± 0.1 | 4.857 | 2.8 |
| 20.39 ± 0.1 | 4.351 | 1.3 |
| 20.91 ± 0.1 | 4.246 | 6.5 |
| 21.76 ± 0.1 | 4.081 | 1.7 |
| 22.10 ± 0.1 | 4.018 | 1.4 |
| 22.88 ± 0.1 | 3.884 | 1.0 |
| 23.95 ± 0.1 | 3.712 | 1.9 |
| 24.11 ± 0.1 | 3.688 | 2.9 |
| 24.94 ± 0.1 | 3.567 | 1.0 |
| 25.47 ± 0.1 | 3.495 | 1.7 |
| 26.10 ± 0.1 | 3.404 | 0.7 |
| 26.61 ± 0.1 | 3.347 | 2.5 |
| 27.00 ± 0.1 | 3.300 | 2.7 |
| 27.49 ± 0.1 | 3.242 | 3.6 |
| 27.98 ± 0.1 | 3.187 | 1.5 |
| 28.93 ± 0.1 | 3.084 | 7.5 |
| 29.84 ± 0.1 | 2.992 | 1.1 |
| 30.48 ± 0.1 | 2.931 | 1.5 |
| 30.81 ± 0.1 | 2.900 | 1.0 |
| 31.49 ± 0.1 | 2.839 | 2.9 |
| 32.19 ± 0.1 | 2.778 | 0.8 |
| 32.49 ± 0.1 | 2.754 | 1.4 |
| 33.70 ± 0.1 | 2.657 | 1.1 |
| 34.60 ± 0.1 | 2.590 | 0.7 |
| 34.88 ± 0.1 | 2.570 | 0.8 |
| 36.11 ± 0.1 | 2.486 | 0.5 |
| 36.48 ± 0.1 | 2.461 | 0.5 |
| 36.98 ± 0.1 | 2.429 | 0.6 |
| 37.90 ± 0.1 | 2.372 | 1.1 |
| 38.16 ± 0.1 | 2.356 | 1.6 |
| 39.05 ± 0.1 | 2.305 | 0.6 |
| 39.84 ± 0.1 | 2.261 | 3.9 |

Example 3

Micronization of Crystalline Form I 17α-ethynyl-androst-5-ene-3β,7β,17β-triol

Crystalline material from Example 2 was feed by vibrator feeder into the into grinding chamber of a Jet-O-Mizer Model 0101 by Fluid Energy, Air Compressor, with air compressor output at around 120 psi, air pressure at Pusher Nozzle and Grinding Nozzle at approximately 110 psi 4 with a vibrator feed of ~5-10 g/m in. Crystalline 17α-ethynyl-androst-5-ene-3β,7β,17β-triol (Compound 1) having a particle size distribution (volume weighted average) given in Table 2 (Result-Before Micronization) is micronized in this manner to provide crystalline Compound 1 having particle size distribution (volume weighted distribution) given in Table 2 (Result-After Micronization).

TABLE 2

Particle Size Distribution for Micronized Crystalline Form I Compound 1

| Test Name | Result-Before Micronization | Result-After Micronization |
|---|---|---|
| 90% as D(0.90) | 90% is ≤331.57 micron | 90% is ≤7.00 micron |
| 95% as D(0.95) | 95% is ≤409.25 micron | 95% is ≤8.47 micron |

TABLE 2-continued

Particle Size Distribution for Micronized Crystalline Form I Compound 1

| Test Name | Result-Before Micronization | Result-After Micronization |
|---|---|---|
| 50% as D(0.50) | 50% is ≤148.84 micron | 50% is ≤3.33 micron |
| 10% as D(0.1) | 10% is ≤67.45 micron | 10% is ≤1.68 micron |
| 5% as D(0.05) | 5% is ≤49.47 micron | 5% is ≤1.14 micron |

Figure 2:
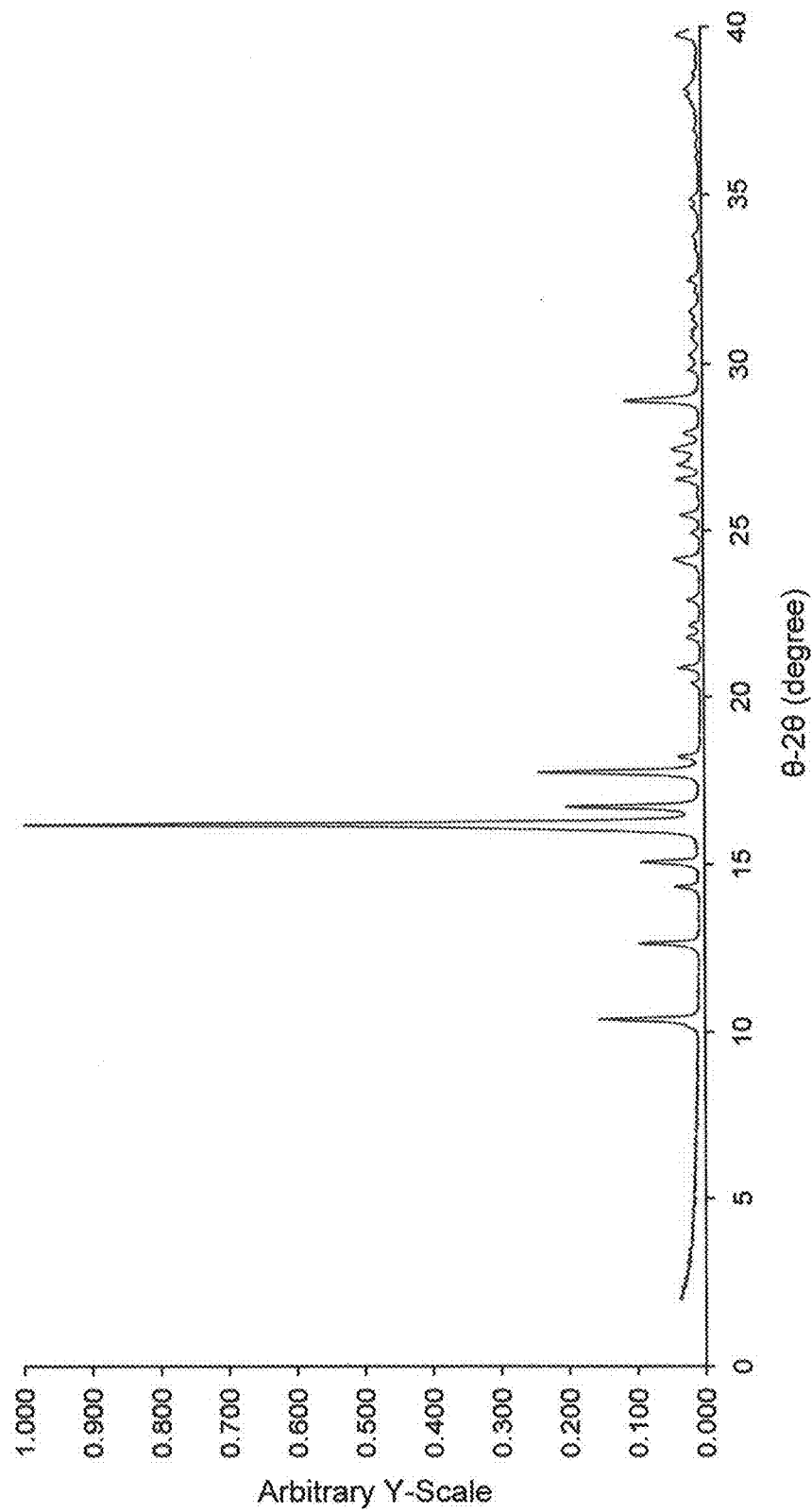
FIG. 2 is a high resolution XRPD pattern of Form I 17α-ethynyl-androst-5-ene-3β,7β,17β-triol after bulk micronization.

Crystalline 17α-ethynyl-androst-5-ene-3β,7β,17β-triol obtained from this procedure is represented by the low resolution XRPD pattern of FIG. 2. The XRPD pattern of FIG. 2 is essentially identical to the XRPD pattern of FIG. 1 (Pattern A). The peak listing for the X-Ray Powder XRPD pattern of FIG. 2 is provided in Table 1B.

TABLE 1B

Peak Listing for XRPD Pattern of Micronized Crystalline Form I High Resolution Pattern A

| °2θ | d space (Å) | Intensity (%) |
|---|---|---|
| 10.38 ± 0.1 | 8.520 ± 0.083 | 15 |
| 12.64 ± 0.1 | 7.004 ± 0.056 | 9 |
| 14.33 ± 0.1 | 6.182 ± 0.043 | 4 |
| 15.08 ± 0.1 | 5.876 ± 0.039 | 9 |
| 16.20 ± 0.1 | 5.472 ± 0.034 | 100 |
| 16.73 ± 0.1 | 5.303 ± 0.032 | 20 |
| 17.75 ± 0.1 | 4.996 ± 0.028 | 24 |
| 18.20 ± 0.1 | 4.873 ± 0.027 | 4 |
| 20.46 ± 0.1 | 4.351 ± 0.021 | 1 |
| 20.89 ± 0.1 | 4.258 ± 0.020 | 3 |
| 21.76 ± 0.1 | 4.084 ± 0.019 | 2 |
| 22.15 ± 0.1 | 4.017 ± 0.018 | 2 |
| 22.95 ± 0.1 | 3.886 ± 0.017 | 2 |
| 24.12 ± 0.1 | 3.690 ± 0.015 | 4 |
| 24.91 ± 0.1 | 3.575 ± 0.014 | 1 |
| 25.49 ± 0.1 | 3.497 ± 0.014 | 3 |
| 26.56 ± 0.1 | 3.358 ± 0.012 | 3 |
| 27.03 ± 0.1 | 3.303 ± 0.012 | 3 |
| 27.46 ± 0.1 | 3.246 ± 0.012 | 4 |
| 27.95 ± 0.1 | 3.195 ± 0.011 | 3 |
| 28.92 ± 0.1 | 3.088 ± 0.010 | 11 |
| 29.82 ± 0.1 | 2.996 ± 0.010 | 2 |

Figure 4:
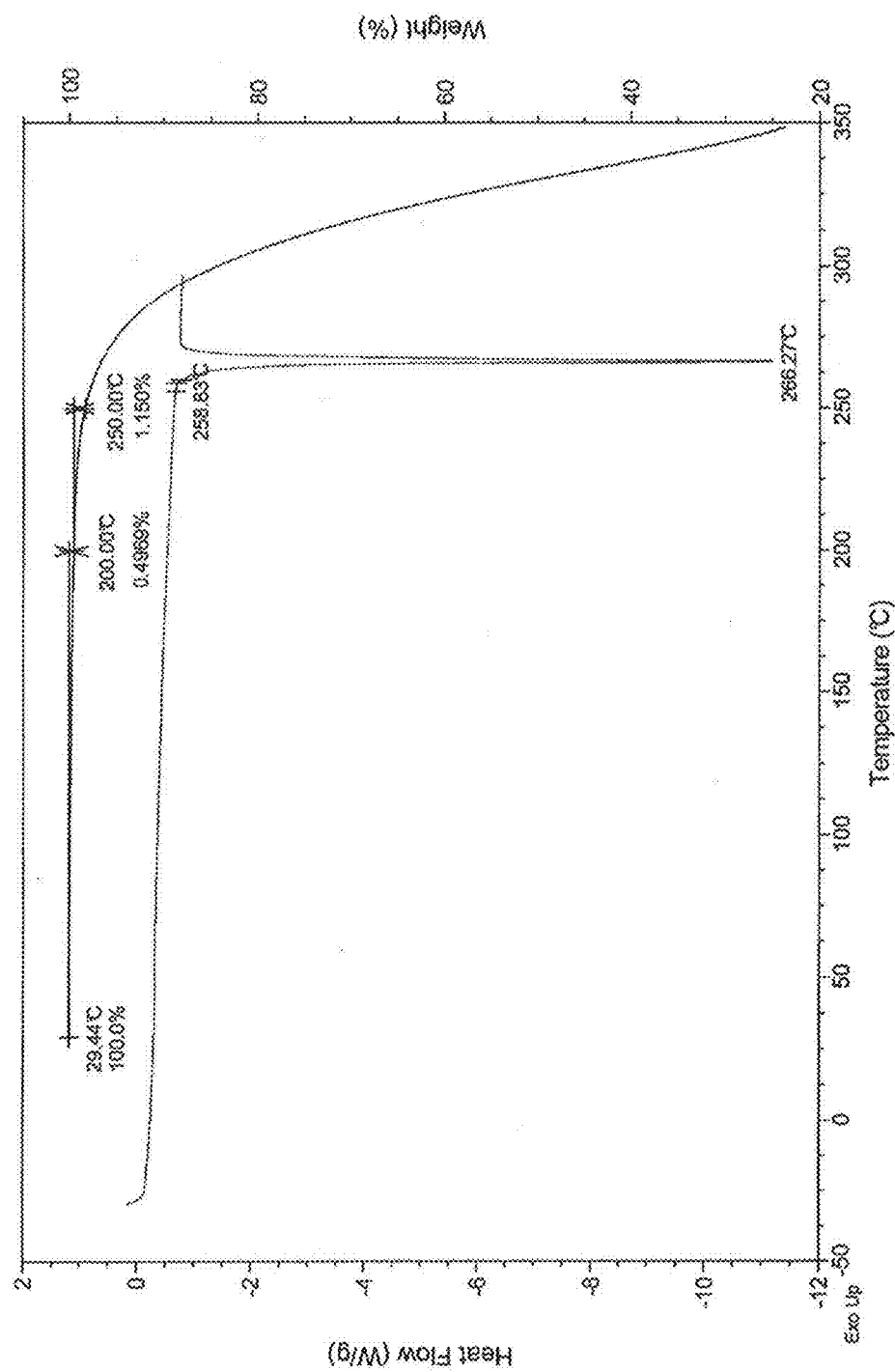
FIG. 4 provides differential scanning calorimetry and thermogravimetric analysis thermograms of a sample containing crystalline Form I 17α-ethynyl-androst-5-ene-3β,7β,17β-triol.

The DSC and TGA thermograms for Form I using a 10° C./min. temperature ramp are presented in FIG. 4. The DSC thermogram show a sharp prominent endotherm at about 266° C., which is otherwise featureless. The TGA thermogram shows about 0.5% weight loss from about 30° C. to about 200° C. and an additional weight loss of about 1.2% from 200° C. to 250° C. with significant weight loss beginning thereafter. TG-IR analysis indicates loss of acetylene is associated with this significant loss in weight. Melting point determination in an open capillary shows an apparent melting point at about 256° C. Using slower san rates (e.g. 2° C./min) in DSC provides multiple endotherms some of even lower temperature. These differences between DSC and open capillary methods may be attributable to varying amounts of decomposition occurring dependent on the conditions and technique used.

The peak listing for Raman absorptions in the Raman spectrum of Form I shown in FIG. 5 is provided in Table 3.

TABLE 3

Peak Listing for Absorptions for Raman Spectrum of Form I

| cm−1 | Intensity | cm−1 | Intensity | cm−1 | Intensity | cm−1 | Intensity |
|---|---|---|---|---|---|---|---|
| 150.4 | 3.83 | 644.0 | 3.38 | 1081.8 | 2.53 | 2105.9 | 14.34 |
| 225.6 | 8.87 | 682.6 | 1.18 | 1099.2 | 1.36 | 2842.5 | 5.57 |
| 246.8 | 3.36 | 711.5 | 0.78 | 1120.4 | 1.49 | 2859.9 | 6.80 |
| 287.3 | 2.22 | | 1.56 | 1132.0 | 2.64 | 2886.9 | 11.19 |
| 300.8 | 2.22 | 9.53 | 2.43 | 1176.3 | 2.68 | 2937.0 | 8.58 |
| 335.5 | 2.74 | 744.3 | 1.18 | 1195.6 | 3.23 | 2946.7 | 7.37 |
| 370.2 | 4.75 | 808.0 | 1.58 | 1214.9 | 2.51 | 2973.7 | 7.17 |
| 399.1 | 1.31 | 833.0 | 1.93 | 1241.9 | 1.22 | 2993.0 | 6.75 |
| 437.7 | 4.14 | 862.0 | 2.13 | 1263.1 | 2.17 | 3037.3 | 1.37 |
| 457.0 | 3.16 | 892.8 | 1.97 | 1297.8 | 2.12 | 3280.3 | 1.72 |
| 470.5 | 5.90 | 914.0 | 3.38 | 1322.9 | 2.58 | 3365.2 | 0.90 |
| 484.0 | 2.04 | 954.5 | 1.18 | 1349.9 | 1.89 | | |
| 507.1 | 2.23 | 975.8 | 0.78 | 1384.6 | 2.03 | | |
| 580.4 | 5.28 | 1004.7 | 1.15 | 1436.7 | 6.38 | | |
| 607.4 | 1.83 | 1022.0 | 2.43 | 1467.5 | 2.94 | | |
| 624.8 | 1.62 | 1052.9 | 1.18 | 1673.9 | 6.07 | | |

Example 4

Alternate Preparations of Solid State Forms Comprising Crystalline Form I 17α-ethynyl-androst-5-ene-3β,7β,17β-triol A suspension of 33.37 g of 17α-ethynyl-androst-5-ene-3β,7β,17β-triol, prepared from Example 2, in 372 mL THF and 56 mL methanol was heated to reflux and then allowed to cool to RT. After filtering through Celite the filtrate was reduced in volume by 50% under reduced pressure and then stirred for 0.5 h at ambient temperature. The collected solids were dried under vacuum at 50° C. for 2 d to give 17.72 g of the title material.

Figure 3:
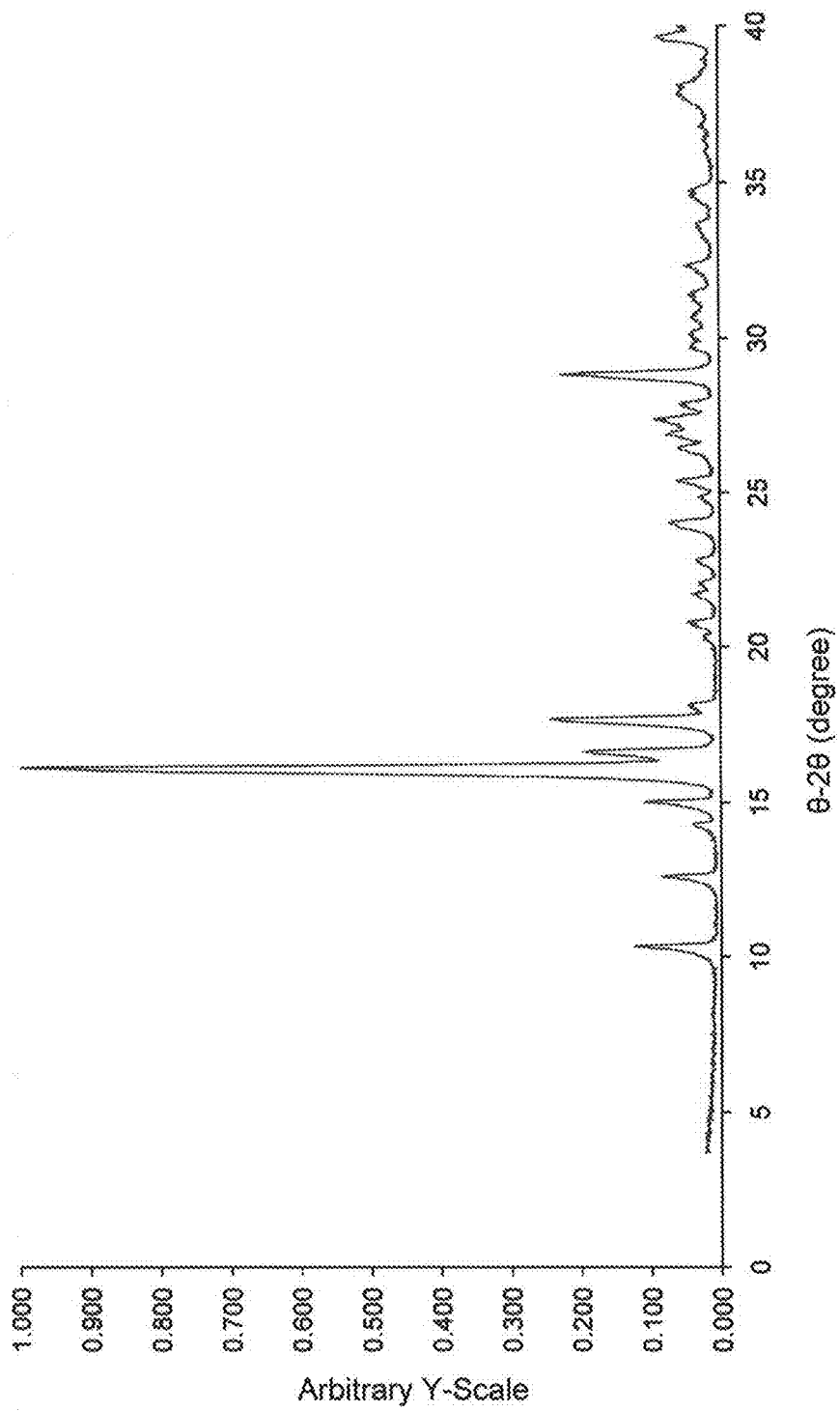
FIG. 3 is a low resolution XRPD of crystalline material from an alternate preparation of Form I 17α-ethynyl-androst-5-ene-3β,7β,17β-triol.

Crystalline 17α-ethynyl-androst-5-ene-3β,7β,17β-triol (Compound 1) obtained from this procedure is of purity 99% and is represented by the low resolution XRPD pattern of FIG. 3, which is substantially identical to the XRPD pattern in FIG. 1 or FIG. 2. The peak listing for the XRPD pattern of FIG. 3 is provided in Table 4.

TABLE 4

Peak Listing for XRPD Pattern of Crystalline Compound 1 Obtained From An Alternate Preparation-Low Resolution

| °2θ | d space (Å) | Intensity (%) |
|---|---|---|
| 10.30 ± 0.1 | 8.584 | 10 |
| 12.54 ± 0.1 | 7.051 | 7 |
| 14.98 ± 0.1 | 5.917 | 8 |
| 16.07 ± 0.1 | 5.510 | 100 |
| 16.58 ± 0.1 | 5.344 | 18 |
| 17.63 ± 0.1 | 5.028 | 23 |
| 18.07 ± 0.1 | 4.906 | 4 |
| 20.73 ± 0.1 | 4.282 | 4 |
| 23.94 ± 0.1 | 3.715 | 6 |
| 25.33 ± 0.1 | 3.513 | 5 |
| 26.39 ± 0.1 | 3.374 | 5 |
| 26.88 ± 0.1 | 3.314 | 6 |
| 27.32 ± 0.1 | 3.262 | 8 |
| 27.80 ± 0.1 | 3.207 | 4 |
| 28.78 ± 0.1 | 3.100 | 21 |
| 32.30 ± 0.1 | 2.769 | 3 |
| 37.82 ± 0.1 | 2.377 | 4 |
| 38.06 ± 0.1 | 2.362 | 4 |
| 39.60 ± 0.1 | 2.274 | 8 |

Other methods to prepare crystalline Compound 1 having XRPD patterns substantially or essentially identical to XRPD Pattern A are given in Table 5. Crystalline material having the XRPD pattern A with the morphology of tablets, blades, plates or needles is referred to as Form I tablets, Form I blades, Form I plates or Form I needles, respectively. Crystalline material prepared from Example 3 has the morphology of tablets. FIG. 6 provides optical microscopic observations of Form I tablets and Form I needles. Form I tablets are expected to have the advantage of favorable flow characteristics (i.e., handling) in manufacturing. Form I needles have expected advantages associated with particles having higher surface to volume ratio.

TABLE 5

Various Other Preparation Methods for Crystalline Compound 1 Having XRPD Pattern A and Their Morphologies

| Solvent System | Technique | Morphology |
|---|---|---|
| Acetone | SC/FE | Plates |
| Dioxane | Slurry | Undefined |
| Dioxane | SC | Plates, Needles |
| Ethanol | VFE | Undefined |
| Ethanol | FE | Tablets |
| Ethanol:heptane (1:6) | CP | Undefined |
| Isopropanol | Slurry | Undefined |
| Methanol | Rotoevaporation | Undefined |
| Tetrahydrofuran | FE | Blades out of glass |
| Tetrahydrofuran | SC/FE | Plates |
| Tetrahydrofuran:Ethanol (1:1) | FE | Blades out of glass |
| Trifluoroethanol | FE | Blades |

Example 5

Preparation of a Crystalline-Amorphous Mixture of 17α-ethynyl-androst-5-ene-3β,7β,17β-triol A ethanolic solution of 17α-ethynyl-androst-5-ene-3β,7β,17β-triol (7.0 g in 263 mL) is sprayed dried using a Yamato spray dryer Model Pulvis GB22 and a FMI lab pump using the following conditions: atomizer air temp of ambient, inlet temperature of 57° C., drying air temperature of 57° C., drying air flow rate of 0.20 m²/min. and a pump setting of 0.5. The particles so obtained are dried under vacuum at 40° C. for 2-3 h to give 4.89 g of the titled material. The solid state form of Compound 1 prepared in this manner is predominately crystalline Form I with about 5-10% amorphous Compound 1.

Example 6. Preparation of a Solid State Form Comprising Crystalline Form II 17α-ethynyl-androst-5-ene-3β,7β,17β-triol Substantially pure Compound 1, preferably 99% or greater purity, as micronized Form I crystals was slurried at ambient temperature in ethyl acetate for 9 days. The filtrate was collected and filtered further through a 0.2 micron filter and the allowed to evaporate at ambient temperature and pressure until crystals are produced. Alternatively, methy ethyl ketone was used as the slurry solvent.

Figure 7:
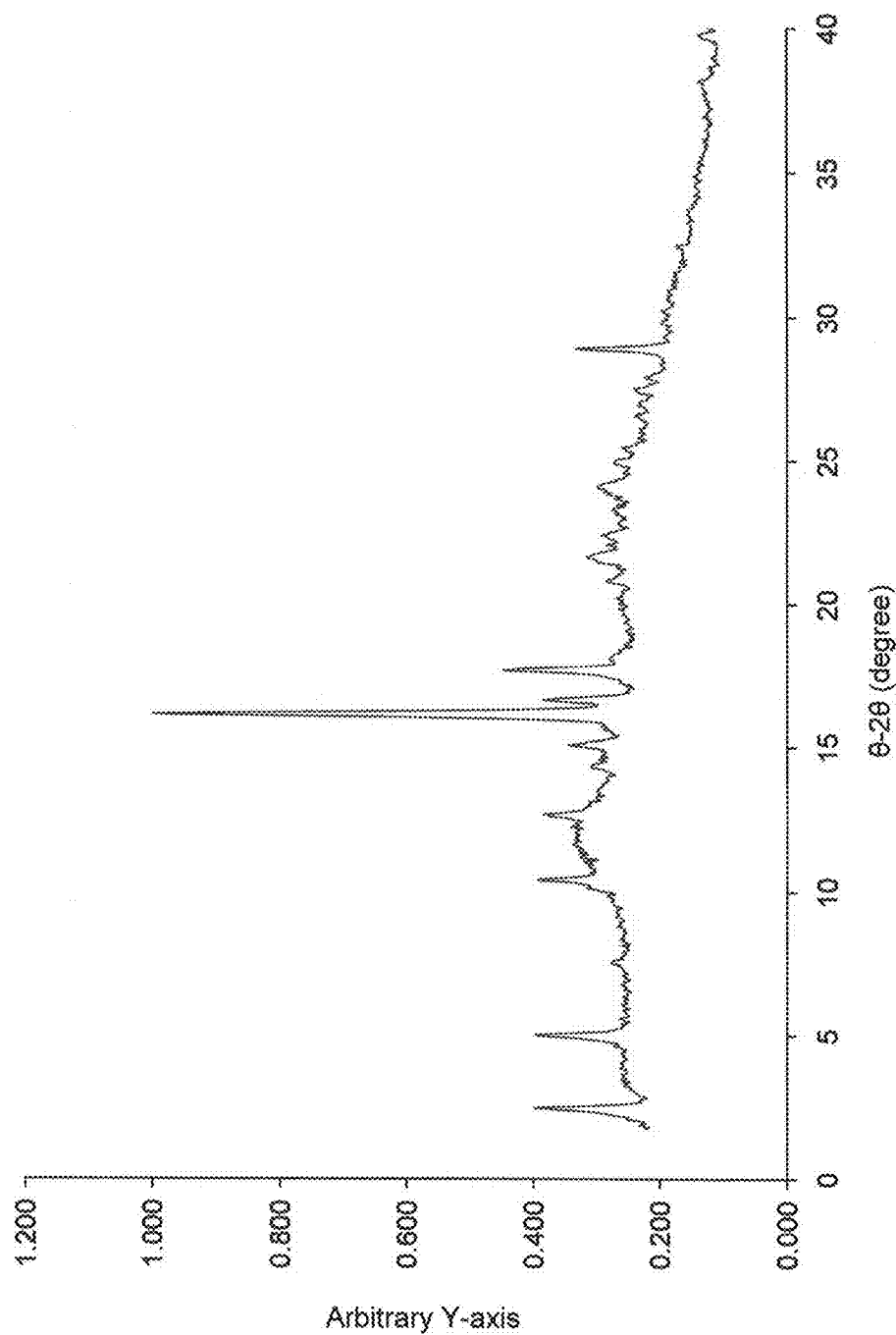
FIG. 7 is a low resolution XRPD pattern of a sample containing crystalline Form II 17α-ethynyl-androst-5-ene-3β,7β,17β-triol.

Crystalline 17α-ethynyl-androst-5-ene-3β,7β,17β-triol obtained from this procedure is represented by the low resolution XRPD pattern (Pattern C) of FIG. 7. The peak listing for the XRPD pattern of FIG. 7 is provided in Table 6.

TABLE 6

Peak Listing for XRPD Pattern C-Low Resolution

| °2θ | Intensity (%) |
|---|---|
| 2.49 ± 0.1 | 10 |
| 5.04 ± 0.1 | 4 |
| 7.56 ± 0.1 | 3 |
| 10.44 ± 0.1 | 4 |
| 12.69 ± 0.1 | 4 |
| 14.43 ± 0.1 | 3 |
| 15.09 ± 0.1 | 3 |
| 16.20 ± 0.1 | 100 |
| 16.68 ± 0.1 | 4 |
| 17.73 ± 0.1 | 4 |
| 20.79 ± 0.1 | 3 |
| 21.72 ± 0.1 | 3 |
| 24.12 ± 0.1 | 3 |
| 28.92 ± 0.1 | 3 |

Pattern C is similar to Pattern A except for the presence of low angle 2-theta peaks at 2.5, 5.0 and 7.6.

Figure 8:
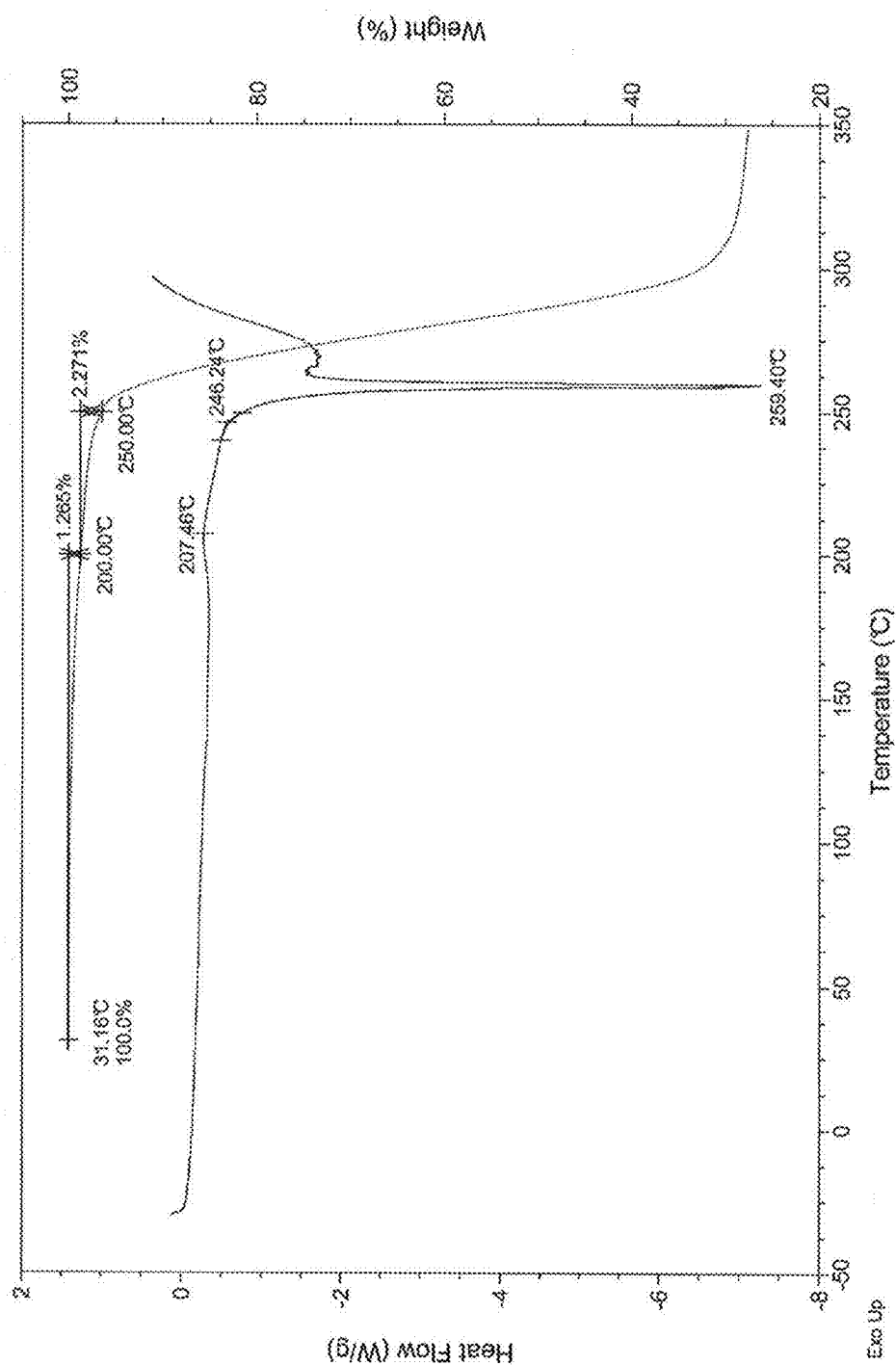
FIG. 8 shows differential scanning calorimetry and thermogravimetric thermograms of a sample containing crystalline Form II 17α-ethynyl-androst-5-ene-3β,7β,17β-triol.

The DSC and TGA thermograms for this crystalline material using a 10° C./min. temperature ramp are presented in FIG. 8. The DSC thermogram shows a broad weak exotherm centered at about 207° C. and a prominent sharp endotherm at about 259° C. (onset at about 246° C.). The TGA thermogram shows about 1.3% weight loss from about 30° C. to about 200° C. and an additional weight loss of about 2.3% from 200° C. to 250° C. with significant weight loss beginning thereafter. TG-IR analysis indicates loss of acetylene is associated with this significant loss in weight.

Example 7

Computational Determination of Form I Unit Cell Parameters

Figure 9:
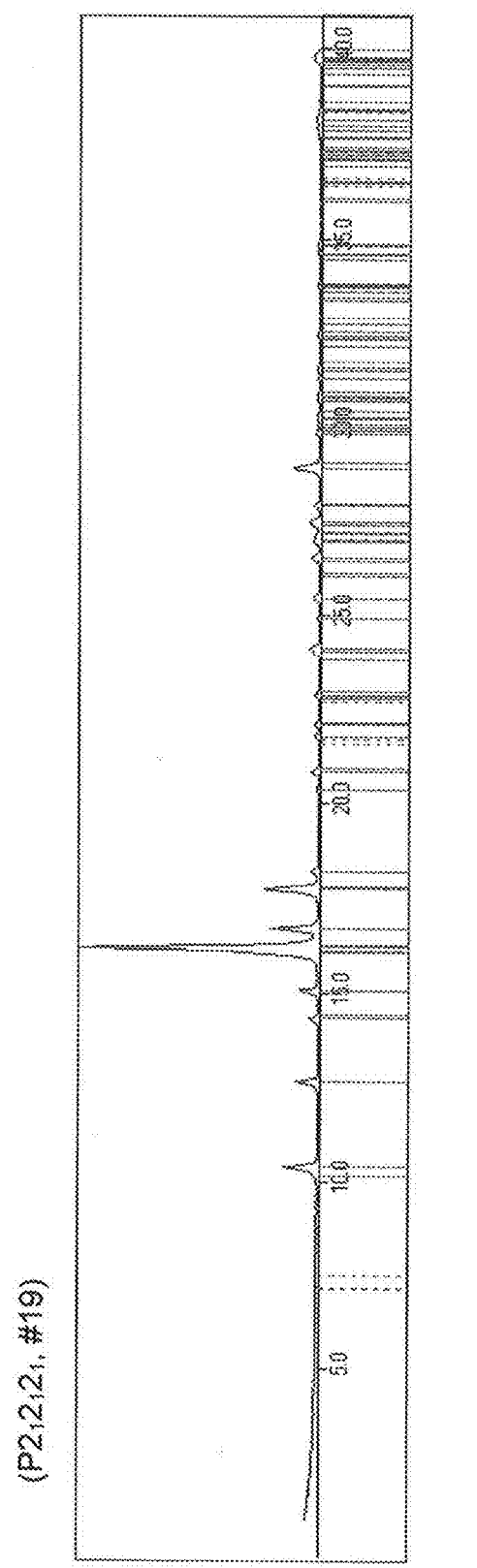
FIG. 9 is a comparison of an experimentally derived XRPD pattern for crystalline Form I 17α-ethynyl-androst-5-ene-3β,7β,17β-triol with allowed reflections from an indexing solution.

The high resolution XRPD pattern of FIG. 1B was indexed was indexed using DASH™ version 3.1. The indexed solution was verified and illustrated using CHECK-CELL™ version 11/01/04. FIG. 9 compares the indexed pattern of Form I with the experimentally derived Pattern A. Agreement between the allowed peak positions (solid lines) and the observed peaks indicates a consistent unit cell dimension. Systematic absences due to constructive interference of otherwise allowed peaks (dotted lines) indicate the assigned extinction symbol is consistent with the observed pattern. The space group [$P2_12_12_1$ (#19)] for Form I consistent with the assigned extinction symbol, unit cell parameters and quantities derived from them are tabulated in Table 8. Successful indexing indicates this crystalline material is comprised primarily of a single crystalline phase.

Figure 10:
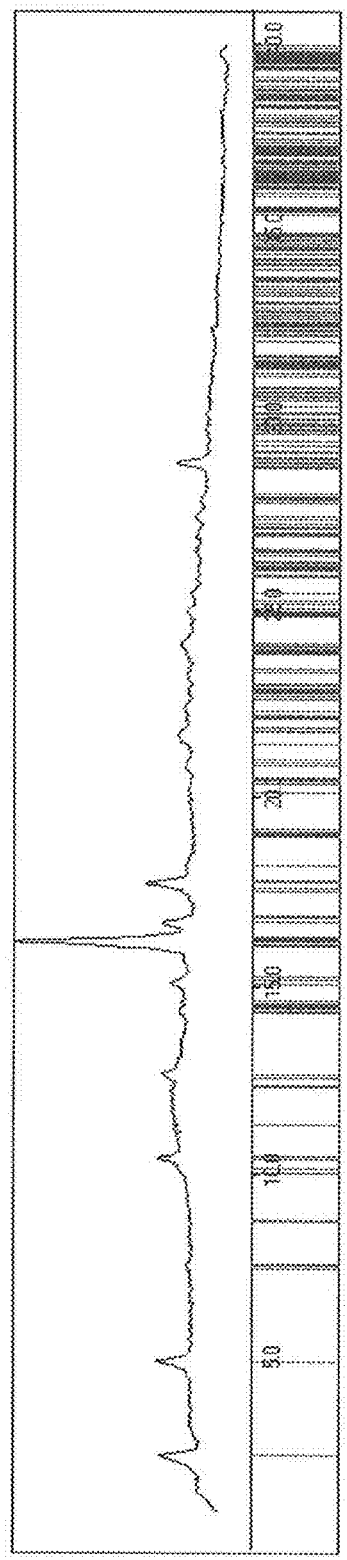
FIG. 10 is a comparison of an experimentally derived XRPD pattern for crystalline Form II 17α-ethynyl-androst-5-ene-3β,7β,17β-triol with allowed reflections from an indexing solution.

The above indexing solution does not account for the low angle 2-theta peak observed for the solid state form obtained from Example 6. These reflections are consistent with reducing the symmetry of the unit cell derived for Form I by reducing the $2_1$ screw of the short axis to a proper 2-fold rotation axis and tripling this axis (i.e., three neighboring crystallographically equivalent unit cells become nonequivalent). The symmetry group ($P2_12_12$, #18) and unit cell parameters obtained after these symmetry operations is provided in Table 8. FIG. 10 compares the indexed pattern of Form II with the experimentally derived Pattern C.

TABLE 8

Indexing Solutions and Derived Quantities

| Form | Form I | Form II |
|---|---|---|
| Family and Space Group | Orthorhombic P2$_1$2$_1$2$_1$ (#19) | Orthorhombic P2$_1$2$_1$2 (#18) |
| Z'/Z | 1/4 | 3/12 |
| a (Å) | 11.740 | 12.273 |
| b (Å) | 12.273 | 12.339 |
| c (Å) | 12.339 | 35.220 |
| α (deg) | 90 | 90 |
| β (deg) | 90 | 90 |
| γ (deg) | 90 | 90 |
| Volume (Å$^3$/cell) | 1777.9 | 5333.6 |
| V/Z (Å$^3$/asym. unit) | 444.5 | |
| Assumed Composition$^a$ | C$_{21}$H$_{30}$O$_3$ | |
| Density (g/cm$^3$)$^a$ | 1.24 | |
| Weight Fraction | N/A | |
| Solvent (%)$^a$ | | |
| XRPD File | 329880 | 331226 |

Example 8

Preparation of a Solid State Form Comprising Crystalline Form III 17α-ethynyl-androst-5-ene-3β, 7β,17β-triol Form III was prepared by crash precipitation of an ethanolic solution of substantially pure Compound 1 at ambient temperature by adding water to the solution to provide a EtOH:water solvent ratio of 1:8.

Figure 11:
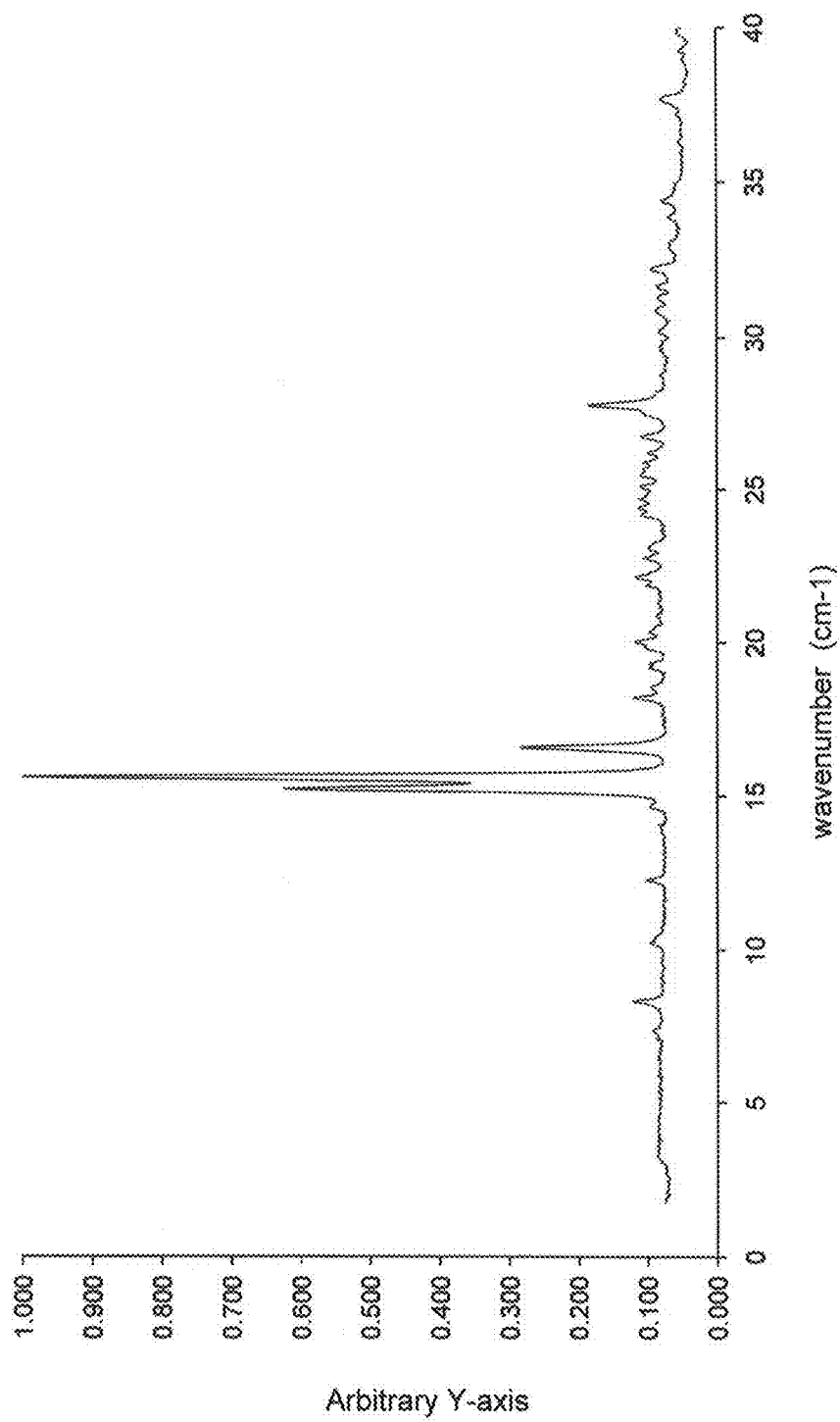
FIG. 11 is a low resolution XRPD of a sample containing crystalline Form III 17α-ethynyl-androst-5-ene-3β,7β,17β-triol.

Crystalline 17α-ethynyl-androst-5-ene-3β,7β,17β-triol obtained from this procedure is represented by the low resolution XRPD pattern (Pattern B) of FIG. 11. The peak listing for the XRPD pattern of FIG. 11 is provided in Table 9.

TABLE 9

Peak Listing for XRPD Pattern B-Low Resolution

| °2θ | d space (Å) | Intensity (%) |
|---|---|---|
| 7.41 ± 0.1 | 11.979 ± 0.164 | 2 |
| 8.34 ± 0.1 | 10.602 ± 0.128 | 7 |
| 10.23 ± 0.1 | 8.622 ± 0.085 | 3 |
| 12.27 ± 0.1 | 7.214 ± 0.059 | 4 |
| 14.67 ± 0.1 | 6.038 ± 0.041 | 3 |
| 15.24 ± 0.1 | 5.814 ± 0.038 | 54 |
| 15.66 ± 0.1 | 5.659 ± 0.036 | 100 |
| 16.59 ± 0.1 | 5.344 ± 0.032 | 32 |
| 18.21 ± 0.1 | 4.872 ± 0.027 | 5 |
| 18.54 ± 0.1 | 4.786 ± 0.026 | 3 |
| 19.32 ± 0.1 | 4.601 ± 0.024 | 3 |
| 20.04 ± 0.1 | 4.431 ± 0.022 | 5 |
| 20.37 ± 0.1 | 4.360 ± 0.021 | 3 |
| 21.87 ± 0.1 | 4.064 ± 0.018 | 3 |
| 22.11 ± 0.1 | 4.021 ± 0.018 | 5 |
| 22.77 ± 0.1 | 3.905 ± 0.017 | 3 |
| 23.10 ± 0.1 | 3.855 ± 0.017 | 3 |
| 24.18 ± 0.1 | 3.681 ± 0.015 | 5 |
| 24.42 ± 0.1 | 3.650 ± 0.015 | 4 |
| 24.69 ± 0.1 | 3.610 ± 0.014 | 5 |
| 25.11 ± 0.1 | 3.551 ± 0.014 | 6 |
| 25.65 ± 0.1 | 3.481 ± 0.013 | 4 |
| 25.86 ± 0.1 | 3.445 ± 0.013 | 4 |
| 26.19 ± 0.1 | 3.403 ± 0.013 | 3 |
| 26.73 ± 0.1 | 3.335 ± 0.012 | 3 |
| 27.75 ± 0.1 | 3.215 ± 0.011 | 11 |

Figure 12:
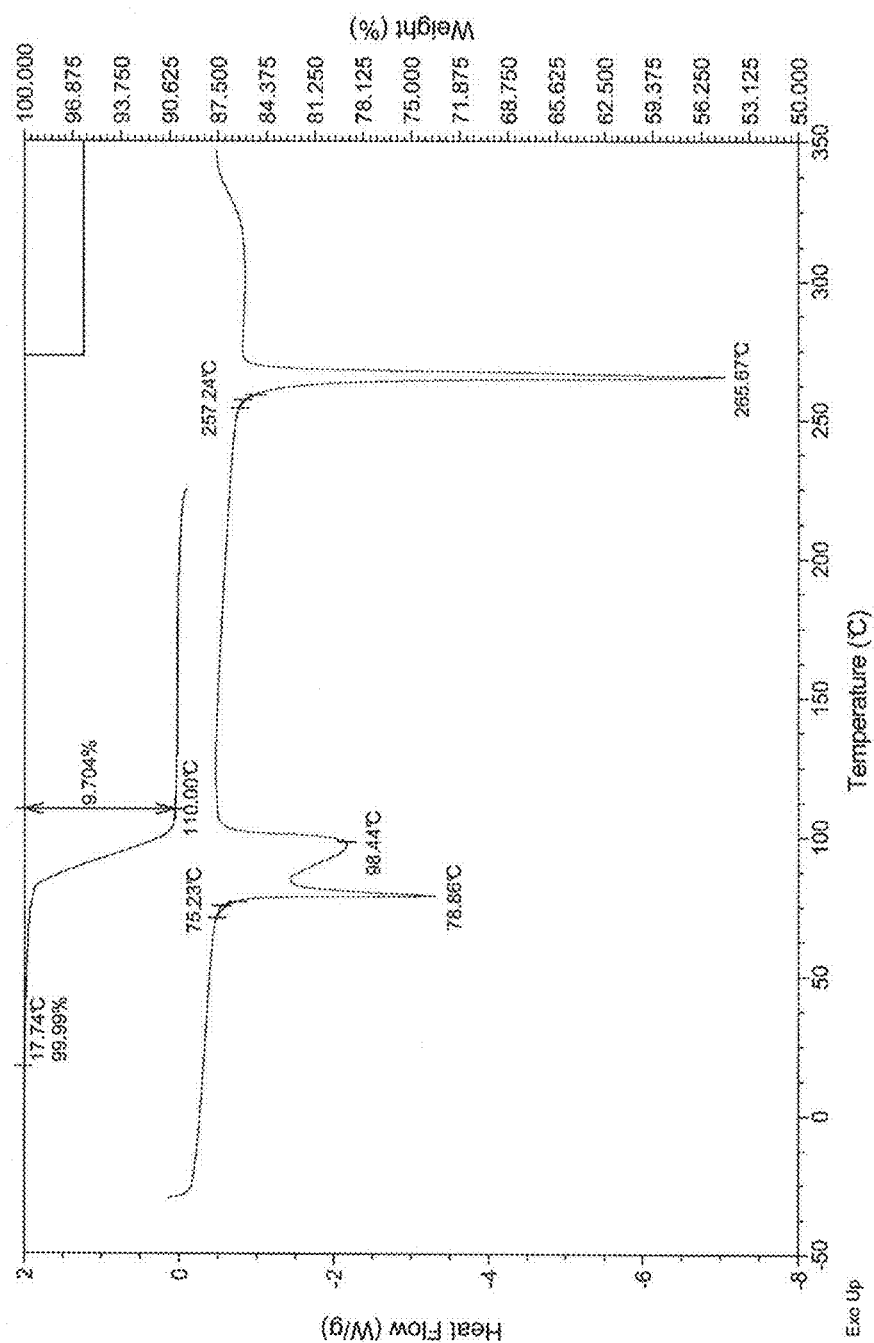
FIG. 12 are differential scanning calorimetry and thermogravimetric analysis thermograms of a sample containing crystalline Form III 17α-ethynyl-androst-5-ene-3β,7β,17β-triol.

The DSC and TGA thermograms for this crystalline material using a 10° C./min. temperature ramp are presented in FIG. 12 The DSC thermogram shows a prominent sharp endotherm at about 266° C. (onset at about 258° C.), an additional endotherm at about 1.7° C. (onset at about −4.16° C.) and a broad endotherm centered at about 105° C. Associated with the lower two DSC endotherms is about 9.6% weight loss in TGA from about 20° C. to about 110° C. TG-IR analysis indicates water loss is associated with this loss in weight. These results are consistent with a pseudopolymorph that is a dihydrate The peak listing for Raman absorptions in the Raman spectrum of FIG. 13 of this crystalline material is shown is given in Table 10.

TABLE 10

Peak Listing for Raman Absorptions for a Solid State Form Comprising Crystalline Form III

| cm-1 | Intensity | cm-1 | Intensity | cm-1 | Intensity | cm-1 | Intensity |
|---|---|---|---|---|---|---|---|
| 146.5 | 2.52 | 744.3 | 0.90 | 1133.9 | 0.89 | 2854.1 | 1.26 |
| 223.6 | 1.94 | 809.9 | 0.43 | 1160.9 | 0.44 | 2892.7 | 1.14 |
| 250.6 | 1.53 | 862.0 | 0.41 | 1182.1 | 0.85 | 2933.2 | 2.41 |
| 293.1 | 0.73 | 875.5 | 0.50 | 1195.6 | 0.64 | 2950.5 | 1.67 |
| 335.5 | 1.12 | 894.7 | 0.87 | 1226.5 | 0.59 | 2966.0 | 1.94 |
| 379.8 | 1.09 | 914.0 | 0.39 | 1251.5 | 0.93 | 2985.2 | 1.36 |
| 401.1 | 0.37 | 952.6 | 0.50 | 1278.5 | 0.57 | 3029.6 | 0.31 |
| 435.8 | 1.54 | 970.0 | 0.66 | 1299.7 | 0.64 | 3272.6 | 0.36 |
| 457.0 | 1.20 | 983.5 | 0.63 | 1319.0 | 0.95 | | |
| 516.8 | 1.10 | 1008.5 | 1.03 | 1344.1 | 0.79 | | |
| 580.4 | 1.19 | 1027.8 | 0.55 | 1380.7 | 0.51 | | |
| 605.5 | 0.51 | 1049.0 | 0.81 | 1436.7 | 1.78 | | |
| 619.0 | 0.45 | 1068.3 | 0.63 | 1469.4 | 0.99 | | |
| 653.7 | 0.48 | 1081.8 | 0.55 | 1666.1 | 1.43 | | |
| 680.7 | 3.55 | 1105.0 | 0.79 | 2107.8 | 2.88 | | |
| 711.5 | 0.54 | 1118.5 | 0.71 | 2832.9 | 0.79 | | |

Example 9

Preparation of a Solid State Form Comprising Crystalline Form IV 17α-ethynyl-androst-5-ene-3β, 7β,17β-triol Form IV was prepared by dissolving about 24 mg substantially pure Compound 1 in about 1 mL 1:1 chloroform: methanol and filtering the solution through a 0.2 micron filter. The solution was then allowed to evaporate under ambient temperature and pressure until solids formed.

Figure 14:
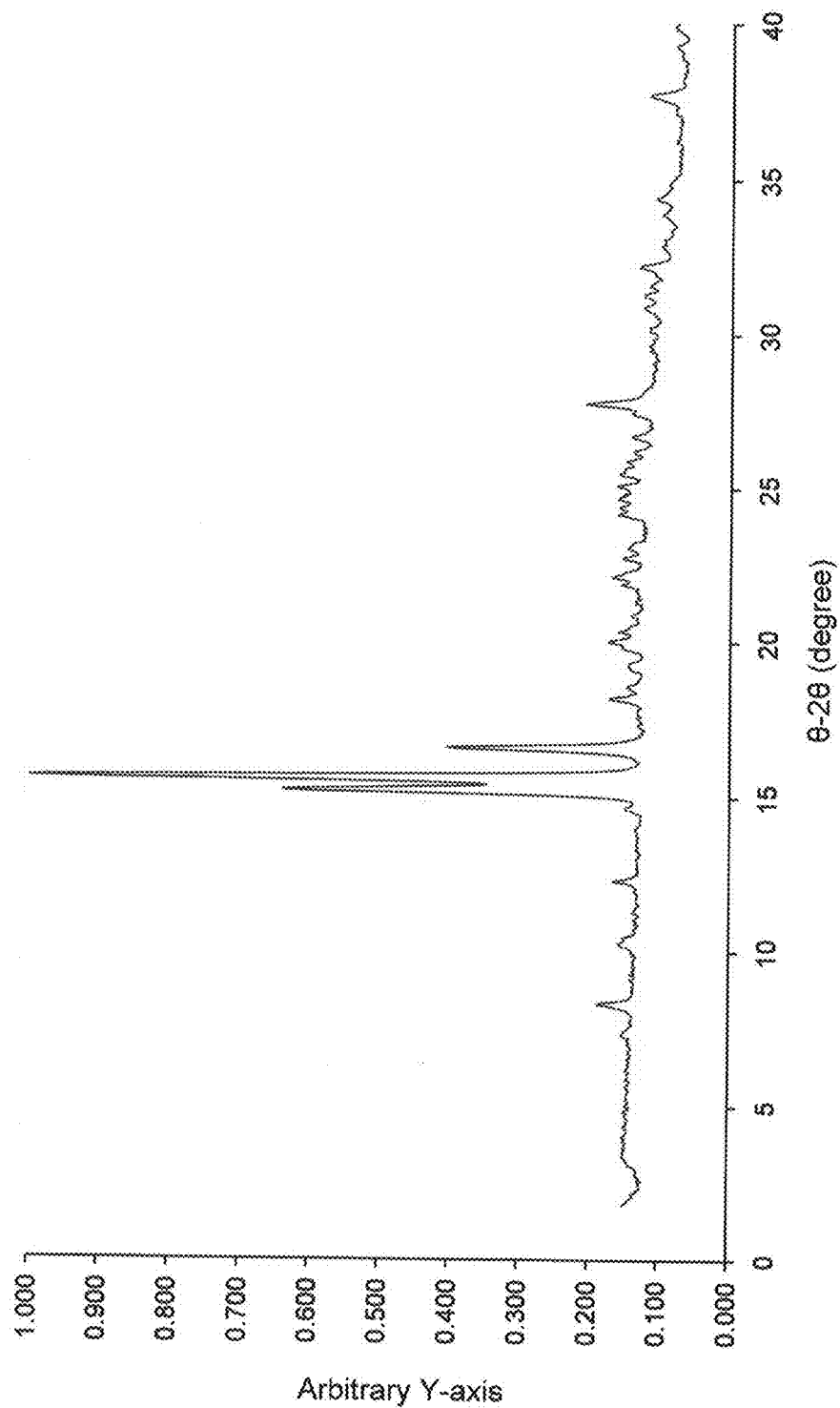
FIG. 14 is a low resolution XRPD pattern of a sample containing crystalline Form IV 17α-ethynyl-androst-5-ene-3β,7β,17β-triol.

Crystalline 17α-ethynyl-androst-5-ene-3β,7β,17β-triol obtained from this procedure is represented by the low resolution XRPD pattern of FIG. 14. The peak listing for the XRPD pattern of FIG. 14 is provided in Table 11.

TABLE 11

Peak Listing for XRPD Pattern of Form IV

| °2θ | Intensity (%) |
|---|---|
| 7.44 ± 0.1 | 2.6 |
| 8.31 ± 0.1 | 3.1 |
| 10.44 ± 0.1 | 2.7 |
| 12.27 ± 0.1 | 2.7 |
| 15.24 ± 0.1 | 67 |
| 15.66 ± 0.1 | 100 |
| 16.20 ± 0.1 | 3.2 |
| 16.62 ± 0.1 | 69 |
| 17.85 ± 0.1 | 2.3 |
| 18.21 ± 0.1 | 2.5 |
| 18.51 ± 0.1 | 2.3 |
| 19.32 ± 0.1 | 2.3 |
| 20.04 ± 0.1 | 2.6 |
| 20.43 ± 0.1 | 2.5 |

TABLE 11-continued

Peak Listing for XRPD Pattern of Form IV

| °2θ | Intensity (%) |
|---|---|
| 22.11 ± 0.1 | 2.5 |
| 22.86 ± 0.1 | 2.2 |
| 23.22 ± 0.1 | 2.2 |
| 24.48 ± 0.1 | 2.3 |
| 24.69 ± 0.1 | 2.6 |
| 25.08 ± 0.1 | 2.6 |
| 25.56 ± 0.1 | 2.3 |
| 25.92 ± 0.1 | 2.3 |
| 26.22 ± 0.1 | 2.2 |
| 26.73 ± 0.1 | 1.9 |
| 27.75 ± 0.1 | 2.5 |
| 30.15 ± 0.1 | 1.7 |
| 31.32 ± 0.1 | 1.8 |
| 32.25 ± 0.1 | 1.8 |
| 34.47 ± 0.1 | 1.6 |
| 37.74 ± 0.1 | 1.6 |

Figure 15:
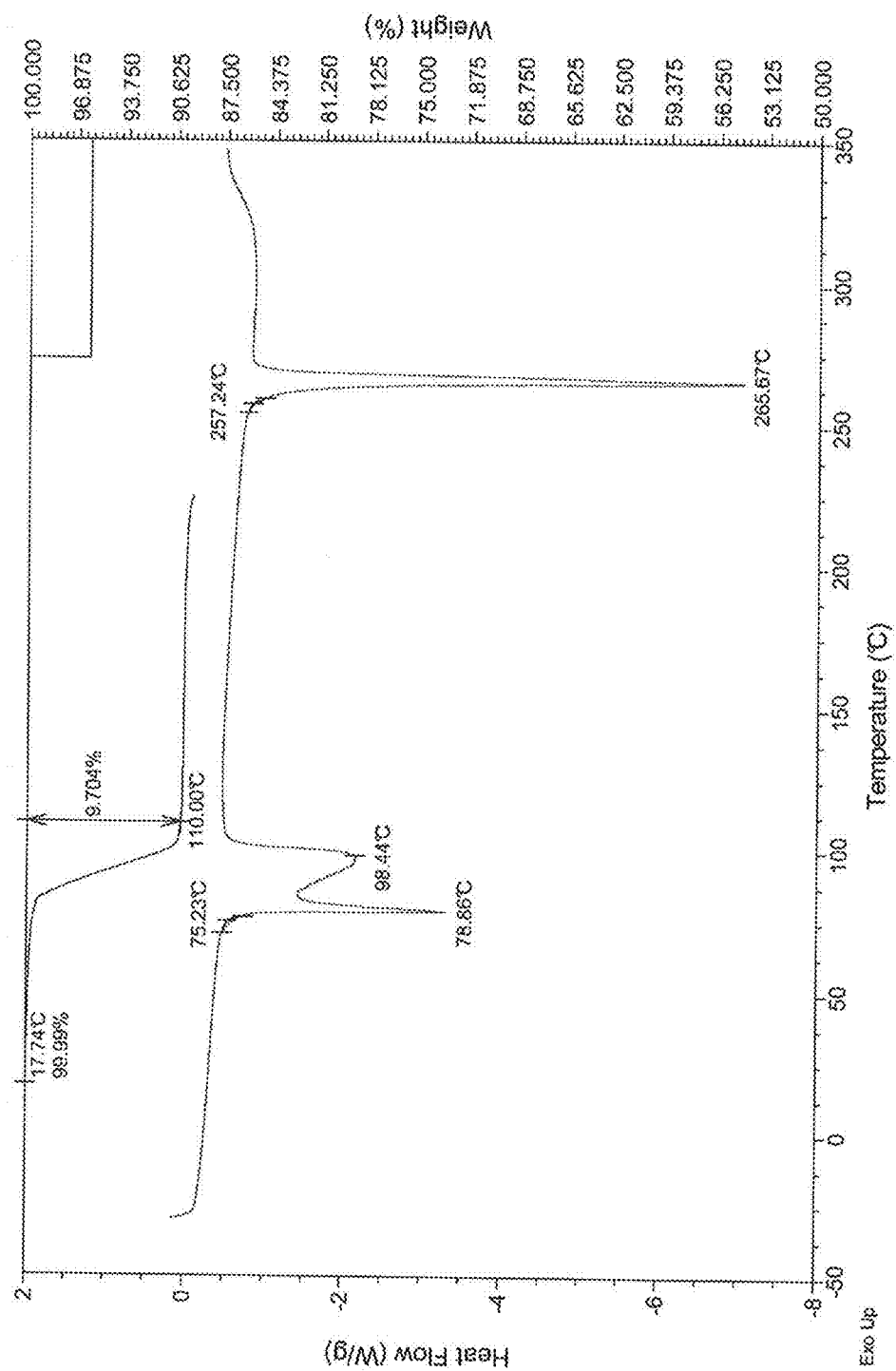
FIG. 15 are differential scanning calorimetry and thermogravimetric analysis thermograms of a sample containing crystalline Form IV 17α-ethynyl-androst-5-ene-3β,7β,17β-triol.

The DSC and TGA thermograms for this crystalline material using a 10° C./min. temperature ramp are presented in FIG. 15. The DSC thermogram shows a prominent sharp endotherm at about 266° C. (onset at about 257° C.), an additional endotherm at about 79° C. (onset at about 75° C.) or 88° C. (onset at about 84° C.) and an overlapping broad endotherm centered at about 98° C. Associated with the lower two DSC endotherms is about 9.7% weight loss in TGA from about 20° C. to about 110° C. These results are consistent with a pseudopolymorph comprising Compound 1 and methanol.

Figure 16B:
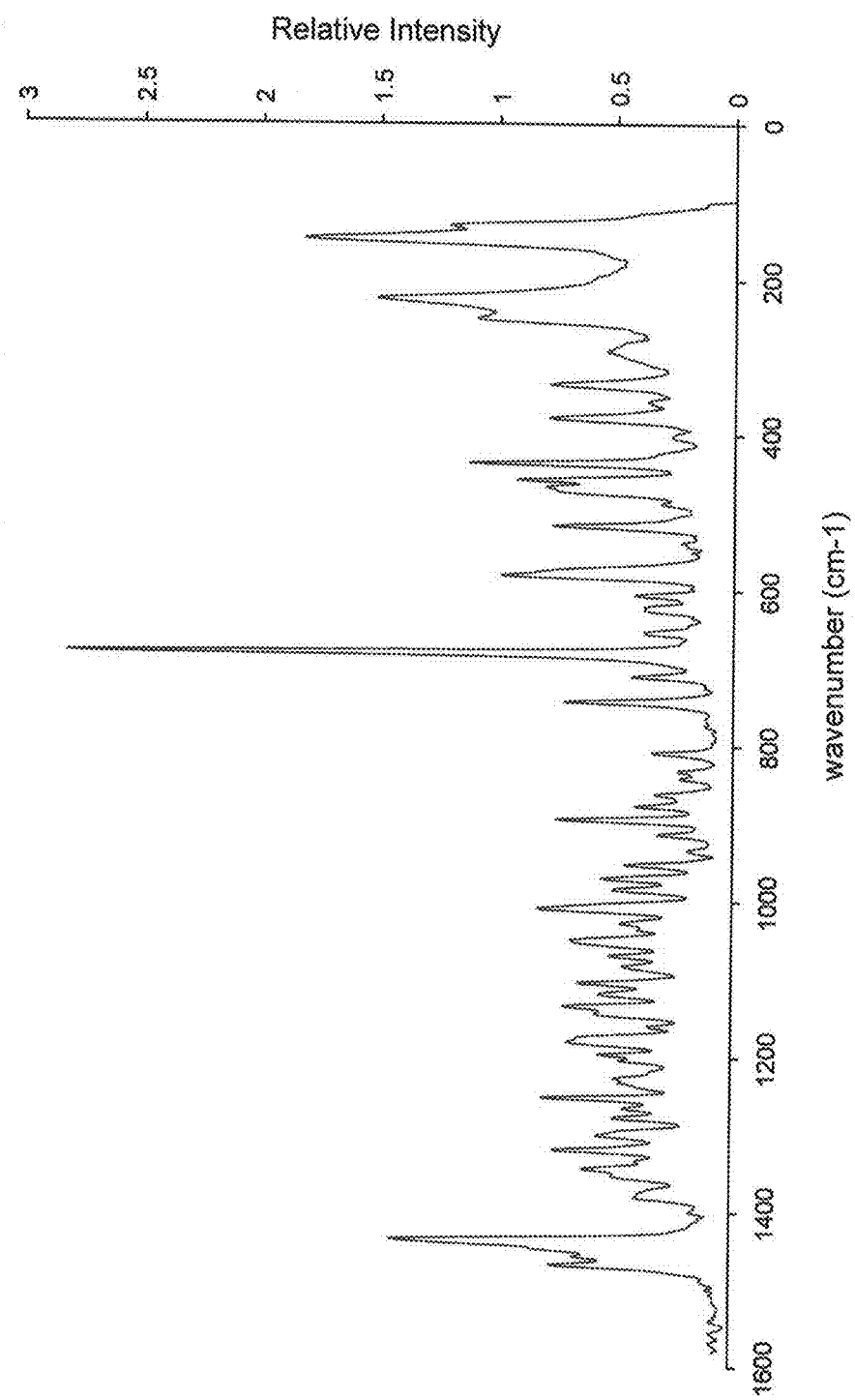
FIG. 16B is a Raman spectrum for a sample containing crystalline Form IV 17α-ethynyl-androst-5-ene-3β,7β,17β-triol.

The peak listing for Raman absorptions in the Raman spectrum of FIG. 16 of this crystalline material is shown is given in Table 12.

TABLE 12

Peak Listing for Raman Absorptions for a Solid State Form Comprising Crystalline Form IV

| cm−1 | Intensity | cm−1 | Intensity | cm−1 | Intensity | cm−1 | Intensity |
|---|---|---|---|---|---|---|---|
| 146.5 | 1.82 | 808.0 | 0.34 | 1195.6 | 0.56 | 2950.5 | 1.72 |
| 223.6 | 1.52 | 877.4 | 0.41 | 1226.5 | 0.49 | 2966.0 | 1.92 |
| 291.1 | 0.54 | 894.7 | 0.75 | 1251.5 | 0.80 | 2985.2 | 1.36 |
| 335.5 | 0.78 | 914.0 | 0.32 | 1276.6 | 0.50 | 3029.6 | 0.33 |
| 377.9 | 0.79 | 952.6 | 0.45 | 1299.7 | 0.57 | 3270.7 | 0.26 |
| 435.8 | 1.12 | 970.0 | 0.55 | 1319.0 | 0.75 | | |
| 457.0 | 0.92 | 983.5 | 0.50 | 1344.1 | 0.63 | | |
| 466.6 | 0.80 | 1008.5 | 0.82 | 1380.7 | 0.40 | | |
| 516.8 | 0.77 | 1027.8 | 0.47 | 1436.7 | 1.43 | | |
| 580.4 | 0.99 | 1049.0 | 0.68 | 1469.4 | 0.76 | | |
| 605.5 | 0.42 | 1068.3 | 0.52 | 1666.1 | 1.10 | | |
| 622.8 | 0.38 | 1081.8 | 0.46 | 2107.8 | 2.81 | | |
| 653.7 | 0.38 | 1105.0 | 0.65 | 2832.9 | 0.85 | | |
| 680.7 | 2.81 | 1118.5 | 0.56 | 2858.0 | 1.41 | | |
| 711.5 | 0.43 | 1133.9 | 0.71 | 2890.7 | 1.28 | | |
| 744.3 | 0.71 | 1180.2 | 0.69 | 2933.2 | 2.39 | | |

Example 10

Preparation of Amorphous 17α-ethynyl-androst-5-ene-3β,7β,17β-triol

Amorphous Compound 1 was prepared by first heating a mixture of 150 mg Compound 1 in 11 mL t-butanol at 45° C. and then filtering the solution to remove residual solids. The solution was then lyophilized to provide the title material. XRPD analysis shows a broad band centered at about 16 2-theta degrees with no distinctive peaks as shown in FIG. 17 consistent for amorphous material.

Figure 18:
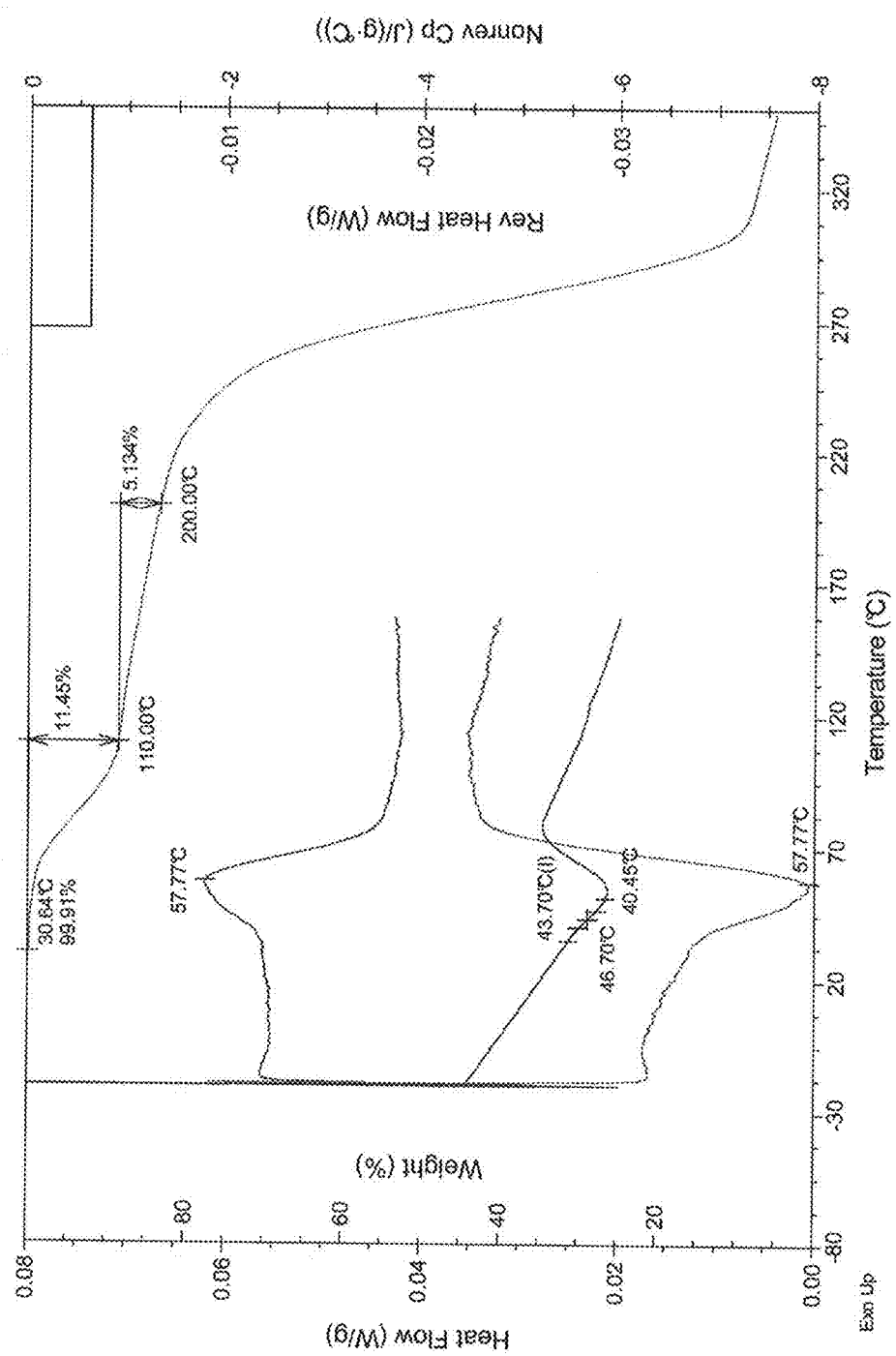
FIG. 18 provides differential scanning calorimetry and thermogravimetric analysis thermograms of a sample containing amorphous 17α-ethynyl-androst-5-ene-3β,7β,17β-triol substantially free of crystalline 17α-ethynyl-androst-5-ene-3β,7β,17β-triol.

The modulated DSC thermogram, using a temperature ramp of 1° C./min., in FIG. 18 shows a reversing heat flow trace (middle DSC trace) that provides a glass transition temperature ($T_g$) of 44° C. when measured at the inflection point of the trace. The upper DSC trace in this Figure shows the non-reversing heat flow and the lower DSC trace is the total heat flow. TGA, using a 10° C./min. temperature ramp, also in FIG. 18, shows a weight loss of about 11.5% from about 30° C. to about 110° C. and an additional weight loss of about 5% between about 110° C. and about 200° C. with significant weight loss thereafter. Brief thermal stress of a sample of amorphous Compound 1 at 40° C. resulted in crystalline material that contains Form I.

The peak listing for Raman absorptions in the Raman spectrum of FIG. 19 of amorphous material is given in Table 13.

TABLE 13

Peak Listing for Raman Absorptions for Amorphous Compound 1

| cm−1 | Intensity |
|---|---|
| 146.5 | 0.52 |
| 225.6 | 0.99 |
| 331.6 | 0.34 |
| 372.1 | 0.50 |
| 435.8 | 0.47 |
| 470.5 | 0.62 |
| 484.0 | 0.32 |
| 512.9 | 0.32 |
| 538.0 | 0.20 |
| 580.4 | 0.67 |
| 607.4 | 0.32 |
| 622.8 | 0.26 |
| 684.5 | 1.08 |
| 711.5 | 0.23 |
| 748.2 | 0.73 |
| 808.0 | 0.18 |
| 833.0 | 0.15 |
| 862.0 | 0.22 |
| 894.7 | 0.38 |
| 914.0 | 0.26 |
| 973.8 | 0.29 |
| 1006.6 | 0.37 |
| 1052.9 | 0.32 |
| 1103.0 | 0.31 |
| 1120.4 | 0.37 |
| 1174.4 | 0.42 |
| 1199.5 | 0.34 |
| 1251.5 | 0.30 |
| 1301.7 | 0.30 |
| 1326.7 | 0.32 |
| 1384.6 | 0.26 |
| 1438.6 | 0.95 |
| 1673.9 | 0.55 |
| 2105.8 | 1.15 |
| 2858.0 | 1.03 |
| 2888.8 | 1.02 |
| 2937.0 | 1.45 |
| 2971.7 | 1.22 |

Example 11

Formulations Comprising or Prepared from a Solid State Form of 17α-ethynyl-androst-5-ene-3β,7β,17β-triol The following are example ingredient lists used in preparation of formulations containing Compound 1 in a solid state form (e.g., Form I) that are suitable for oral dosing.

TABLE 14

Formulation Containing 25 mg Compound 1 in Solid State Form

|  | % w/w | mg/capsule |
|---|---|---|
| Drug Substance | | |
| Compound 1 micronized | 10 | 25 |
| Excipients | | |
| Sodium lauryl sulfate, NF | 20 | 50 |
| Microcrystalline cellulose, NF (Avicel PH 102) | 43.2 | 108 |
| Crospovidone, NF (Polypasdone XL-10) | 26 | 65 |
| Magnesium stearate, NF | 0.8 | 2 |
| Total | 100 | 250 |
| Hard gelatin capsule # 1 | | |

TABLE 15

Formulation Containing 5 mg Compound 1 in Solid State Form

|  | % w/w | mg/capsule |
|---|---|---|
| Drug Substance | | |
| Compound 1 micronized | 3.3 | 5 |
| Excipients | | |
| Sodium lauryl sulfate, NF | 16.7 | 25 |
| Microcrystalline cellulose, NF (Avicel PH 102) | 49.3 | 74 |
| Crospovidone, NF (Polypasdone XL-10) | 30.0 | 45 |
| Magnesium stearate, NF | 0.7 | 1 |
| Total | 100 | 150 |
| Hard gelatin capsule # 2 | | |

The following is an example ingredient list used in preparation of a suspension formulation of Compound 1 in a solid state form (e.g., Form I) suitable for oral or parenteral dosing.

TABLE 16

Suspension Formulation Containing Compound 1 in Solid State Form

|  | w/v or % w/v |
|---|---|
| Drug Substance | |
| Compound 1 micronized | 3 mg/mL |
| Excipients | |
| Polysorbate 80 | 2 |
| Sodium Carboxymethycellulose | 0.1 |
| Sodium Chloride | 0.9 |
| Phenol | 0.05 |
| Deionized water | |

Suspension formulations of at least up to 100 mg/mL may be prepared using the formulation of Table 16. In the formulations above and in the following examples solid state forms of Compound 1 (e.g., amorphous or crystalline Form I) are preferably micronized to a mean volume weighted particle size (Dv, 50) of between about 3 to about 100 microns prior to blending with excipients. In one embodiment, Crystalline Form I is micronized to give a particle size with (Dv, 90) ≤10 μm (particle size that contains 90% (volume weighted) of all the particles). Selection of appropriate particle size is a tradeoff between improved bioavailability for a solid state form of Compound 1 in a given formulation due to improved dissolution rate of solid state Compound 1 and increased manufacturing cost of the formulation as particle size decreases. For example, particle sizes with a mean volume weighted particle size or average diameter of less than about 3 microns typically requires fluid bed micronization [for example, see Julia Z. H, et al. "Fluid bed granulation of a poorly water soluble, low density, micronized drug: comparison with high shear granulation" Int. J. Pharm. Vol. 237, No. 1-2, pp. 1-14 (2002)], which is more costly than jet milling to a larger particle size and is a process more difficult to scale up.

With dosage strengths of less than 5 mg (e.g., 1 mg) pre-blending of micronized Compound 1 with a surface active agent such as sodium lauryl sulfate is sometimes conducted prior to blending with the remaining excipients in order to obtain a uniform distribution of Compound 1 within the formulation.

What is claimed is:

1. Crystalline solvate 17α-ethynylandrost-5-ene-3β,7β,17β-triol.

2. The crystalline solvate of claim 1, wherein the crystalline solvate is crystalline ethanolate 17α-ethynylandrost-5-ene-3β,7β,17β-triol.

3. The crystalline solvate of claim 1 wherein the crystalline solvate is crystalline hydrate 17α-ethynylandrost-5-ene-3β,7β,17β-triol.

4. The crystalline solvate of claim 1, wherein the crystalline solvate is crystalline methanolate 17α-ethynylandrost-5-ene-3β,7β,17β-triol.

5. A pharmaceutical composition comprising the crystalline solvate of claim 1; and one or more pharmaceutically acceptable excipients.

6. The pharmaceutical composition of claim 5, wherein the crystalline solvate is crystalline ethanolate 17α-ethynylandrost-5-ene-3β,7β,17β-triol.

7. The pharmaceutical composition of claim 6, further comprising 1 $CH_3OH$, 0.5 $CH_3OH$, 1 $H_2O$, 0.5 $H_2O$ or 2 $H_2O$ per 17β-ethynylandrost-5-ene-3β,7β,17β-triol.

8. The pharmaceutical composition of claim 5, wherein the crystalline solvate is crystalline hydrate 17αethynylandrost -5-ene -3β,7β,17β-triol.

9. The pharmaceutical composition of claim 5, wherein the crystalline solvate is crystalline methanolate 17α-ethynylandrost 5-ene-3β,7β,17β-triol.

10. The pharmaceutical composition of claim 5, wherein the crystalline solvate is Form III 17αethynylandrost-5-ene-3β,7β,17β-triol.

11. The pharmaceutical composition of claim 5, wherein the crystalline solvate is Form IV 17α-ethynylandrost-5-ene-3β,7β,17β-triol.

12. The pharmaceutical composition of claim 5, wherein the crystalline solvate is Form V 17α-ethynylandrost -5-ene-3β,7β,17β-triol.

13. The pharmaceutical composition of claim 5, wherein the pharmaceutical composition contains less than about 3% by weight of impurities.

14. The pharmaceutical composition of claim 13, wherein the pharmaceutical composition contains less than about 2% by weight of impurities.

15. The pharmaceutical composition of claim 8, wherein the pharmaceutical composition contains less than about 3% by weight of impurities.

16. The pharmaceutical composition of claim 9, wherein the pharmaceutical composition contains less than about 3% by weight of impurities.

17. The pharmaceutical composition of claim 7, wherein the pharmaceutical composition contains less than about 3% by weight of impurities.

18. The pharmaceutical composition of claim 10, wherein the pharmaceutical composition contains less than about 3% by weight of impurities.

19. The pharmaceutical composition of claim 11, wherein the pharmaceutical composition contains less than about 3% by weight of impurities.

20. The pharmaceutical composition of claim 12, wherein the pharmaceutical composition contains less than about 3% by weight of impurities.

* * * * *

UNITED STATES PATENT AND TRADEMARK OFFICE
CERTIFICATE OF CORRECTION

PATENT NO.         : 9,850,271 B2
APPLICATION NO.    : 15/348107
DATED              : December 26, 2017
INVENTOR(S)        : Steven K. White It is certified that error appears in the above-identified patent and that said Letters Patent is hereby corrected as shown below:

In the Specification

In Column 1, Line 52, change "posses" to --possess--.

In Column 3, Line 42, change "(m DSC)," to --(mDSC),--.

In Column 5, Line 59, change "Definitions.As" to --Definitions. As--.

In Column 21, Line 35, change "n" to --In--.

In Column 25, Line 26, change "absorbtion" to --absorption--.

In Column 36, Line 22, after "spectroscopy" insert --.--.

In Column 36, Line 58, after "spectroscopy" insert --.--.

In Column 37, Line 25, after "syndrome" insert --.--.

In Column 42, Line 62, after "80" insert --.--.

In Column 46, Line 8, after "cyclodextrin" insert --.--.

In Column 46, Line 51, change "100" to --100 L--.

In Column 46, Line 55, change "30" to --30 L--.

In Column 46, Line 65, change "(81" to --(81%--.

In Column 48, Line 46, change "feed" to --fed--.

Signed and Sealed this
Fifth Day of March, 2019

Andrei Iancu
*Director of the United States Patent and Trademark Office*

CERTIFICATE OF CORRECTION (continued)
U.S. Pat. No. 9,850,271 B2

In Column 48, Line 51, change "g/m in." to --g/min.--.

In Column 51, Line 61 (Approx.), change "methy" to --methyl--.

In Column 54, Line 8, after "dihydrate" insert --.--.

In Column 57, Line 12 (Approx.), Table 14, change "(Polypasdone" to --(Polyplasdone--.

In Column 57, Line 30 (Approx.), Table 15, change "(Polypasdone" to --(Polyplasdone--.

In the Claims

In Column 58, Line 40, Claim 7, change "17β-" to --17α- --.

In Column 58, Line 43, Claim 8, change "17αethynylandrost -5-ene -3β," to --17α-ethynylandrost-5-ene-3β,--.

In Column 58, Lines 45-46, Claim 9, change "17α-ethynylandrost 5-ene-" to --17α-ethynylandrost-5-ene- --.

In Column 58, Line 48, Claim 10, change "17αethynylandrost-5-ene-" to --17α-ethynylandrost-5-ene- --.